(12) United States Patent
Rice et al.

(10) Patent No.: US 11,332,728 B2
(45) Date of Patent: May 17, 2022

(54) YEAST STRAINS FOR THE EXPRESSION AND SECRETION OF HETEROLOGOUS PROTEINS AT HIGH TEMPERATURES

(71) Applicant: Lallemand Hungary Liquidity Management LLC, Budapest (HU)

(72) Inventors: Charles F. Rice, Hopkinton, NH (US); Ryan Skinner, South Royalton, VT (US); Trisha Barrett, Bradford, VT (US); Aaron Argyros, Etna, NH (US)

(73) Assignee: Lallemand Hungary Liquidity Management LLC, Budapest (HU)

( * ) Notice: Subject to any disclaimer, the term of this patent is extended or adjusted under 35 U.S.C. 154(b) by 216 days.

(21) Appl. No.: 15/757,325

(22) PCT Filed: Aug. 29, 2016

(86) PCT No.: PCT/IB2016/055162
§ 371 (c)(1),
(2) Date: Mar. 2, 2018

(87) PCT Pub. No.: WO2017/037614
PCT Pub. Date: Mar. 9, 2017

(65) Prior Publication Data
US 2018/0265853 A1    Sep. 20, 2018

Related U.S. Application Data

(60) Provisional application No. 62/214,412, filed on Sep. 4, 2015, provisional application No. 62/299,897, filed on Feb. 25, 2016.

(51) Int. Cl.
| | | |
|---|---|---|
| *C12N 15/81* | (2006.01) | |
| *C07K 14/39* | (2006.01) | |
| *C12N 9/30* | (2006.01) | |

(52) U.S. Cl.
CPC .............. *C12N 9/242* (2013.01); *C07K 14/39* (2013.01); *C12N 15/81* (2013.01); *C12Y 302/01001* (2013.01)

(58) Field of Classification Search
None
See application file for complete search history.

(56) References Cited

U.S. PATENT DOCUMENTS

| | | | | |
|---|---|---|---|---|
| 9,223,559 | B2 | 12/2015 | Ito | |
| 10,294,484 | B2 * | 5/2019 | Brevnova | C12N 9/2405 |
| 2009/0325240 | A1 * | 12/2009 | Daniell | C12N 9/2437 |
| | | | | 435/101 |
| 2011/0277179 | A1 * | 11/2011 | Puzio | C07K 14/415 |
| | | | | 800/278 |
| 2013/0323822 | A1 * | 12/2013 | Brevnova | C12Y 302/01004 |
| | | | | 435/254.21 |

FOREIGN PATENT DOCUMENTS

| | | |
|---|---|---|
| WO | 2008/080093 A2 | 7/2008 |
| WO | 2009/137574 A2 | 11/2009 |
| WO | 2011/153516 A2 | 12/2011 |
| WO | 2012/138942 A1 | 10/2012 |
| WO | 2013/128648 A1 | 9/2013 |
| WO | 2013/128948 A1 | 9/2013 |
| WO | 2016/127083 A1 | 8/2016 |

OTHER PUBLICATIONS

Meinhardt et al. Rheostats and Toggle Switches for Modulating Protein Function. Dec. 30, 2013. PLOS One. vol. 8, Issue 12, e83502, pp. 1-11. (Year: 2013).*
Miller et al. Computational predictors fail to identify amino acid substitution effects at rheostat positions. Jan. 30, 2017. Scientific Reports. vol. 7, No. 41329, pp. 1-13. (Year: 2017).*
Sequence Alignment of SEQ ID No. 1 with SEQ ID No. 1863 of USPGPUB 20090325240. Search conducted on Dec. 11, 2021 , 2 pages. (Year: 2021).*
Sequence Alignment of SEQ ID No. 1 with SEQ ID No. 6082 of USPGPUB 20110277179. Search conducted on Dec. 11, 2021 , 2 pages. (Year: 2021).*
Sequence Alignment of SEQ ID No. 1 with SEQ ID No. 445 of USPGPUB 20130323822. Search conducted on Dec. 11, 2021, 2 pages. (Year: 2021).*
Sequence Alignment of SEQ ID No. 1 with SEQ ID No. 445 of USPAT 10294484. Search conducted on Dec. 11, 2021, 3 pages. (Year: 2021).*
Gasser et al., "Protein folding and conformational stress in microbial cells producing recombinant proteins: a host comparative overview," *Microbial Cell Factories* 7:11, 2008.
Hostinová et al., "Cloning and expression of a gene for an alpha-glucosidase from *Saccharomycopsis fibuligera* homologous to family GH31 of yeast glucoamylases," *App. Microbial Biotechnol* 69c:51-56, 2005.
Idiris et al., "Engineering of protein secretion in yeast: strategies and impact on protein production," *App Microbiol Biotechnol* 86:403-417, 2010.
Kwast et al., "Genomic Analyses of Anaerobically Induced Genes in *Saccharomyces cerevisiae*: Functional Roles of Rox1 and Other Factors in Mediating the Anoxic Response," *Journal of Bacteriology* 184(1):250-265, 2002.
Latorre-Garcia et al., "Overexpression of the glucoamylase-encoding STA1 gene of *Saccharomyces cerevisiae* var. *diastaticus* in laboratory and industrial strains of *Saccharomyces*," *World J Microbiol Biotechnol* 24:2957-2963, 2008.
Martinez et al., "Pharmaceutical protein production by yeast: towards production of human blood proteins by microbial fermentation," *Current Opinion in Biotechnology* 23:965-971, 2012.

(Continued)

*Primary Examiner* — Channing S Mahatan
(74) *Attorney, Agent, or Firm* — Seed IP Law Group LLP

(57) ABSTRACT

The present disclosure relates to recombinant yeast strains capable of maintaining their robustness at high temperature as well as recombinant proteins expressed therefrom. The present disclosure also provides methods for using the recombinant yeast strain for making a fermentation product. The present disclosure further process a process for making recombinant yeast strains capable of maintaining their robustness at high temperature.

16 Claims, 11 Drawing Sheets
Specification includes a Sequence Listing.

(56) References Cited

OTHER PUBLICATIONS

Mattanovich et al., "Stress in recombinant protein producing yeasts," *Journal of Biotechnology* 113:121-135, 2004.

Sagt et al., "Introduction of an N-Glycosylation Site Increases Secretion of Heterologous Proteins in Yeasts," *Applied and Environmental Microbiology* 66(11):4940-4944, 2000.

Tai et al., "Two-dimensional Transcriptome Analysis in Chemostat Cultures," *The Journal of Biological Chemistry* 280(1):437-447, 2005.

Ter Linde et al., "Genome-Wide Transcriptional Analysis of Aerobic and Anaerobic Chemostat Cultures of *Saccharomyces cerevisiae*," *Journal of Bacteriology* 181(24):7409-7413, 1999.

\* cited by examiner

… (1)

SEQUENCE LISTING

```
<160> NUMBER OF SEQ ID NOS: 57

<210> SEQ ID NO 1
<211> LENGTH: 515
<212> TYPE: PRT
<213> ORGANISM: Saccharomycopsis fibuligera

<400> SEQUENCE: 1

Met Ile Arg Leu Thr Val Phe Leu Thr Ala Val Phe Ala Ala Val Ala
1               5                   10                  15

Ser Cys Val Pro Val Glu Leu Asp Lys Arg Asn Thr Gly His Phe Gln
            20                  25                  30

Ala Tyr Ser Gly Tyr Thr Val Ala Arg Ser Asn Phe Thr Gln Trp Ile
        35                  40                  45

His Glu Gln Pro Ala Val Ser Trp Tyr Tyr Leu Leu Gln Asn Ile Asp
    50                  55                  60

Tyr Pro Glu Gly Gln Phe Lys Ser Ala Lys Pro Gly Val Val Val Ala
65                  70                  75                  80

Ser Pro Ser Thr Ser Glu Pro Asp Tyr Phe Tyr Gln Trp Thr Arg Asp
                85                  90                  95

Thr Ala Ile Thr Phe Leu Ser Leu Ile Ala Glu Val Glu Asp His Ser
            100                 105                 110

Phe Ser Asn Thr Thr Leu Ala Lys Val Val Glu Tyr Tyr Ile Ser Asn
        115                 120                 125

Thr Tyr Thr Leu Gln Arg Val Ser Asn Pro Ser Gly Asn Phe Asp Ser
    130                 135                 140

Pro Asn His Asp Gly Leu Gly Glu Pro Lys Phe Asn Val Asp Asp Thr
```

```
                145                 150                 155                 160
Ala Tyr Thr Ala Ser Trp Gly Arg Pro Gln Asn Asp Gly Pro Ala Leu
                165                 170                 175

Arg Ala Tyr Ala Ile Ser Arg Tyr Leu Asn Ala Val Ala Lys His Asn
            180                 185                 190

Asn Gly Lys Leu Leu Leu Ala Gly Gln Asn Gly Ile Pro Tyr Ser Ser
        195                 200                 205

Ala Ser Asp Ile Tyr Trp Lys Ile Ile Lys Pro Asp Leu Gln His Val
    210                 215                 220

Ser Thr His Trp Ser Thr Ser Gly Phe Asp Leu Trp Glu Glu Asn Gln
225                 230                 235                 240

Gly Thr His Phe Phe Thr Ala Leu Val Gln Leu Lys Ala Leu Ser Tyr
                245                 250                 255

Gly Ile Pro Leu Ser Lys Thr Tyr Asn Asp Pro Gly Phe Thr Ser Trp
                260                 265                 270

Leu Glu Lys Gln Lys Asp Ala Leu Asn Ser Tyr Ile Asn Ser Ser Gly
            275                 280                 285

Phe Val Asn Ser Gly Lys Lys His Ile Val Glu Ser Pro Gln Leu Ser
        290                 295                 300

Ser Arg Gly Gly Leu Asp Ser Ala Thr Tyr Ile Ala Ala Leu Ile Thr
305                 310                 315                 320

His Asp Ile Gly Asp Asp Thr Tyr Thr Pro Phe Asn Val Asp Asn
                325                 330                 335

Ser Tyr Val Leu Asn Ser Leu Tyr Tyr Leu Val Asp Asn Lys Asn
                340                 345                 350

Arg Tyr Lys Ile Asn Gly Asn Tyr Lys Ala Gly Ala Ala Val Gly Arg
            355                 360                 365

Tyr Pro Glu Asp Val Tyr Asn Gly Val Gly Thr Ser Glu Gly Asn Pro
        370                 375                 380

Trp Gln Leu Ala Thr Ala Tyr Ala Gly Gln Thr Phe Tyr Thr Leu Ala
385                 390                 395                 400

Tyr Asn Ser Leu Lys Asn Lys Asn Leu Val Ile Glu Lys Leu Asn
                405                 410                 415

Tyr Asp Leu Tyr Asn Ser Phe Ile Ala Asp Leu Ser Lys Ile Asp Ser
            420                 425                 430

Ser Tyr Ala Ser Lys Asp Ser Leu Thr Leu Thr Tyr Gly Ser Asp Asn
        435                 440                 445

Tyr Lys Asn Val Ile Lys Ser Leu Leu Gln Phe Gly Asp Ser Phe Leu
    450                 455                 460

Lys Val Leu Leu Asp His Ile Asp Asp Asn Gly Gln Leu Thr Glu Glu
465                 470                 475                 480

Ile Asn Arg Tyr Thr Gly Phe Gln Ala Gly Ala Val Ser Leu Thr Trp
                485                 490                 495

Ser Ser Gly Ser Leu Leu Ser Ala Asn Arg Ala Arg Asn Lys Leu Ile
            500                 505                 510

Glu Leu Leu
        515

<210> SEQ ID NO 2
<211> LENGTH: 515
<212> TYPE: PRT
<213> ORGANISM: Artificial Sequence
<220> FEATURE:
<223> OTHER INFORMATION: Mutated versions of SEQ ID NO: 9
<220> FEATURE:
```

```
<221> NAME/KEY: VARIANT
<222> LOCATION: (8)..(8)
<223> OTHER INFORMATION: Any amino acid except L, preferably S
<220> FEATURE:
<221> NAME/KEY: VARIANT
<222> LOCATION: (11)..(11)
<223> OTHER INFORMATION: Any amino acid except F, preferably I
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: VARIANT
<222> LOCATION: (36)..(36)
<223> OTHER INFORMATION: Any amino acid except G, preferably N, S, T, Y,
      K, P, W
<220> FEATURE:
<221> NAME/KEY: VARIANT
<222> LOCATION: (40)..(40)
<223> OTHER INFORMATION: Any amino acid except A, preferably N, S, T, Y,
      K, P, W
<220> FEATURE:
<221> NAME/KEY: VARIANT
<222> LOCATION: (101)..(101)
<223> OTHER INFORMATION: Any amino acid except F, preferably L
<220> FEATURE:
<221> NAME/KEY: VARIANT
<222> LOCATION: (277)..(277)
<223> OTHER INFORMATION: Any amino acid except K, preferably E
<220> FEATURE:
<221> NAME/KEY: VARIANT
<222> LOCATION: (487)..(487)
<223> OTHER INFORMATION: Any amino acid except F, preferably I

<400> SEQUENCE: 2

Met Ile Arg Leu Thr Val Phe Xaa Thr Ala Val Xaa Ala Ala Val Ala
1               5                   10                  15

Ser Cys Val Pro Val Glu Leu Asp Lys Arg Asn Thr Gly His Phe Gln
            20                  25                  30

Ala Tyr Ser Xaa Tyr Thr Val Xaa Arg Ser Asn Phe Thr Gln Trp Ile
        35                  40                  45

His Glu Gln Pro Ala Val Ser Trp Tyr Tyr Leu Leu Gln Asn Ile Asp
    50                  55                  60

Tyr Pro Glu Gly Gln Phe Lys Ser Ala Lys Pro Gly Val Val Val Ala
65                  70                  75                  80

Ser Pro Ser Thr Ser Glu Pro Asp Tyr Phe Tyr Gln Trp Thr Arg Asp
                85                  90                  95

Thr Ala Ile Thr Xaa Leu Ser Leu Ile Ala Glu Val Glu Asp His Ser
            100                 105                 110

Phe Ser Asn Thr Thr Leu Ala Lys Val Val Glu Tyr Tyr Ile Ser Asn
        115                 120                 125

Thr Tyr Thr Leu Gln Arg Val Ser Asn Pro Ser Gly Asn Phe Asp Ser
130                 135                 140

Pro Asn His Asp Gly Leu Gly Glu Pro Lys Phe Asn Val Asp Asp Thr
145                 150                 155                 160

Ala Tyr Thr Ala Ser Trp Gly Arg Pro Gln Asn Asp Gly Pro Ala Leu
                165                 170                 175

Arg Ala Tyr Ala Ile Ser Arg Tyr Leu Asn Ala Val Ala Lys His Asn
            180                 185                 190

Asn Gly Lys Leu Leu Leu Ala Gly Gln Asn Gly Ile Pro Tyr Ser Ser
        195                 200                 205

Ala Ser Asp Ile Tyr Trp Lys Ile Ile Lys Pro Asp Leu Gln His Val
    210                 215                 220

Ser Thr His Trp Ser Thr Ser Gly Phe Asp Leu Trp Glu Glu Asn Gln
```

```
            225                 230                 235                 240

Gly Thr His Phe Phe Thr Ala Leu Val Gln Leu Lys Ala Leu Ser Tyr
                        245                 250                 255

Gly Ile Pro Leu Ser Lys Thr Tyr Asn Asp Pro Gly Phe Thr Ser Trp
                        260                 265                 270

Leu Glu Lys Gln Xaa Asp Ala Leu Asn Ser Tyr Ile Asn Ser Ser Gly
                        275                 280                 285

Phe Val Asn Ser Gly Lys Lys His Ile Val Glu Ser Pro Gln Leu Ser
                    290                 295                 300

Ser Arg Gly Gly Leu Asp Ser Ala Thr Tyr Ile Ala Ala Leu Ile Thr
        305                 310                 315                 320

His Asp Ile Gly Asp Asp Thr Tyr Thr Pro Phe Asn Val Asp Asn
                        325                 330                 335

Ser Tyr Val Leu Asn Ser Leu Tyr Leu Leu Val Asp Asn Lys Asn
                        340                 345                 350

Arg Tyr Lys Ile Asn Gly Asn Tyr Lys Ala Gly Ala Val Gly Arg
                        355                 360                 365

Tyr Pro Glu Asp Val Tyr Asn Gly Val Gly Thr Ser Glu Gly Asn Pro
                        370                 375                 380

Trp Gln Leu Ala Thr Ala Tyr Ala Gly Gln Thr Phe Tyr Thr Leu Ala
        385                 390                 395                 400

Tyr Asn Ser Leu Lys Asn Lys Asn Leu Val Ile Glu Lys Leu Asn
                        405                 410                 415

Tyr Asp Leu Tyr Asn Ser Phe Ile Ala Asp Leu Ser Lys Ile Asp Ser
                        420                 425                 430

Ser Tyr Ala Ser Lys Asp Ser Leu Thr Leu Thr Tyr Gly Ser Asp Asn
                        435                 440                 445

Tyr Lys Asn Val Ile Lys Ser Leu Leu Gln Phe Gly Asp Ser Phe Leu
                    450                 455                 460

Lys Val Leu Leu Asp His Ile Asp Asp Asn Gly Gln Leu Thr Glu Glu
        465                 470                 475                 480

Ile Asn Arg Tyr Thr Gly Xaa Gln Ala Gly Ala Val Ser Leu Thr Trp
                        485                 490                 495

Ser Ser Gly Ser Leu Leu Ser Ala Asn Arg Ala Arg Asn Lys Leu Ile
                    500                 505                 510

Glu Leu Leu
                515

<210> SEQ ID NO 3
<211> LENGTH: 515
<212> TYPE: PRT
<213> ORGANISM: Artificial Sequence
<220> FEATURE:
<223> OTHER INFORMATION: MP738

<400> SEQUENCE: 3

Met Ile Arg Leu Thr Val Phe Ser Thr Ala Val Ile Ala Ala Val Ala
        1                   5                   10                  15

Ser Cys Val Pro Val Glu Leu Asp Lys Arg Asn Thr Gly His Phe Gln
                        20                  25                  30

Ala Tyr Ser Asn Tyr Thr Val Ala Arg Ser Asn Phe Thr Gln Trp Ile
                        35                  40                  45

His Glu Gln Pro Ala Val Ser Trp Tyr Leu Leu Gln Asn Ile Asp
                    50                  55                  60

Tyr Pro Glu Gly Gln Phe Lys Ser Ala Lys Pro Gly Val Val Val Ala
```

-continued

```
                65                  70                  75                  80
Ser Pro Ser Thr Ser Glu Pro Asp Tyr Phe Tyr Gln Trp Thr Arg Asp
                        85                  90                  95

Thr Ala Ile Thr Leu Leu Ser Leu Ile Ala Glu Val Glu Asp His Ser
                        100                 105                 110

Phe Ser Asn Thr Thr Leu Ala Lys Val Val Glu Tyr Tyr Ile Ser Asn
                        115                 120                 125

Thr Tyr Thr Leu Gln Arg Val Ser Asn Pro Ser Gly Asn Phe Asp Ser
            130                 135                 140

Pro Asn His Asp Gly Leu Gly Glu Pro Lys Phe Asn Val Asp Asp Thr
145                 150                 155                 160

Ala Tyr Thr Ala Ser Trp Gly Arg Pro Gln Asn Asp Gly Pro Ala Leu
                        165                 170                 175

Arg Ala Tyr Ala Ile Ser Arg Tyr Leu Asn Ala Val Ala Lys His Asn
                        180                 185                 190

Asn Gly Lys Leu Leu Leu Ala Gly Gln Asn Gly Ile Pro Tyr Ser Ser
            195                 200                 205

Ala Ser Asp Ile Tyr Trp Lys Ile Lys Pro Asp Leu Gln His Val
            210                 215                 220

Ser Thr His Trp Ser Thr Ser Gly Phe Asp Leu Trp Glu Glu Asn Gln
225                 230                 235                 240

Gly Thr His Phe Phe Thr Ala Leu Val Gln Leu Lys Ala Leu Ser Tyr
                        245                 250                 255

Gly Ile Pro Leu Ser Lys Thr Tyr Asn Asp Pro Gly Phe Thr Ser Trp
                260                 265                 270

Leu Glu Lys Gln Glu Asp Ala Leu Asn Ser Tyr Ile Asn Ser Ser Gly
            275                 280                 285

Phe Val Asn Ser Gly Lys Lys His Ile Val Glu Ser Pro Gln Leu Ser
                290                 295                 300

Ser Arg Gly Gly Leu Asp Ser Ala Thr Tyr Ile Ala Ala Leu Ile Thr
305                 310                 315                 320

His Asp Ile Gly Asp Asp Asp Thr Tyr Thr Pro Phe Asn Val Asp Asn
                        325                 330                 335

Ser Tyr Val Leu Asn Ser Leu Tyr Tyr Leu Val Asp Asn Lys Asn
                340                 345                 350

Arg Tyr Lys Ile Asn Gly Asn Tyr Lys Ala Gly Ala Ala Val Gly Arg
            355                 360                 365

Tyr Pro Glu Asp Val Tyr Asn Gly Val Gly Thr Ser Glu Gly Asn Pro
370                 375                 380

Trp Gln Leu Ala Thr Ala Tyr Ala Gly Gln Thr Phe Tyr Thr Leu Ala
385                 390                 395                 400

Tyr Asn Ser Leu Lys Asn Lys Asn Leu Val Ile Glu Lys Leu Asn
                        405                 410                 415

Tyr Asp Leu Tyr Asn Ser Phe Ile Ala Asp Leu Ser Lys Ile Asp Ser
                420                 425                 430

Ser Tyr Ala Ser Lys Asp Ser Leu Thr Leu Thr Tyr Gly Ser Asp Asn
            435                 440                 445

Tyr Lys Asn Val Ile Lys Ser Leu Leu Gln Phe Gly Asp Ser Phe Leu
450                 455                 460

Lys Val Leu Leu Asp His Ile Asp Asp Asn Gly Gln Leu Thr Glu Glu
465                 470                 475                 480

Ile Asn Arg Tyr Thr Gly Ile Gln Ala Gly Ala Val Ser Leu Thr Trp
                        485                 490                 495
```

```
Ser Ser Gly Ser Leu Leu Ser Ala Asn Arg Ala Arg Asn Lys Leu Ile
            500                 505                 510

Glu Leu Leu
        515

<210> SEQ ID NO 4
<211> LENGTH: 515
<212> TYPE: PRT
<213> ORGANISM: Artificial Sequence
<220> FEATURE:
<223> OTHER INFORMATION: MP743

<400> SEQUENCE: 4

Met Ile Arg Leu Thr Val Phe Leu Thr Ala Val Phe Ala Ala Val Ala
1               5                   10                  15

Ser Cys Val Pro Val Glu Leu Asp Lys Arg Asn Thr Gly His Phe Gln
            20                  25                  30

Ala Tyr Ser Gly Tyr Thr Val Asn Arg Ser Asn Phe Thr Gln Trp Ile
        35                  40                  45

His Glu Gln Pro Ala Val Ser Trp Tyr Tyr Leu Leu Gln Asn Ile Asp
    50                  55                  60

Tyr Pro Glu Gly Gln Phe Lys Ser Ala Lys Pro Gly Val Val Val Ala
65                  70                  75                  80

Ser Pro Ser Thr Ser Glu Pro Asp Tyr Phe Tyr Gln Trp Thr Arg Asp
                85                  90                  95

Thr Ala Ile Thr Phe Leu Ser Leu Ile Ala Glu Val Glu Asp His Ser
            100                 105                 110

Phe Ser Asn Thr Thr Leu Ala Lys Val Val Glu Tyr Tyr Ile Ser Asn
        115                 120                 125

Thr Tyr Thr Leu Gln Arg Val Ser Asn Pro Ser Gly Asn Phe Asp Ser
    130                 135                 140

Pro Asn His Asp Gly Leu Gly Glu Pro Lys Phe Asn Val Asp Asp Thr
145                 150                 155                 160

Ala Tyr Thr Ala Ser Trp Gly Arg Pro Gln Asn Asp Gly Pro Ala Leu
                165                 170                 175

Arg Ala Tyr Ala Ile Ser Arg Tyr Leu Asn Ala Val Ala Lys His Asn
            180                 185                 190

Asn Gly Lys Leu Leu Leu Ala Gly Gln Asn Gly Ile Pro Tyr Ser Ser
        195                 200                 205

Ala Ser Asp Ile Tyr Trp Lys Ile Ile Lys Pro Asp Leu Gln His Val
    210                 215                 220

Ser Thr His Trp Ser Thr Ser Gly Phe Asp Leu Trp Glu Glu Asn Gln
225                 230                 235                 240

Gly Thr His Phe Phe Thr Ala Leu Val Gln Leu Lys Ala Leu Ser Tyr
                245                 250                 255

Gly Ile Pro Leu Ser Lys Thr Tyr Asn Asp Pro Gly Phe Thr Ser Trp
            260                 265                 270

Leu Glu Lys Gln Lys Asp Ala Leu Asn Ser Tyr Ile Asn Ser Ser Gly
        275                 280                 285

Phe Val Asn Ser Gly Lys Lys His Ile Val Glu Ser Pro Gln Leu Ser
    290                 295                 300

Ser Arg Gly Gly Leu Asp Ser Ala Thr Tyr Ile Ala Ala Leu Ile Thr
305                 310                 315                 320

His Asp Ile Gly Asp Asp Asp Thr Tyr Thr Pro Phe Asn Val Asp Asn
                325                 330                 335
```

```
Ser Tyr Val Leu Asn Ser Leu Tyr Tyr Leu Val Asp Asn Lys Asn
                340                 345                 350
Arg Tyr Lys Ile Asn Gly Asn Tyr Lys Ala Gly Ala Val Gly Arg
            355                 360                 365
Tyr Pro Glu Asp Val Tyr Asn Gly Val Gly Thr Ser Glu Gly Asn Pro
    370                 375                 380
Trp Gln Leu Ala Thr Ala Tyr Ala Gly Gln Thr Phe Tyr Thr Leu Ala
385                 390                 395                 400
Tyr Asn Ser Leu Lys Asn Lys Asn Leu Val Ile Glu Lys Leu Asn
                405                 410                 415
Tyr Asp Leu Tyr Asn Ser Phe Ile Ala Asp Leu Ser Lys Ile Asp Ser
                420                 425                 430
Ser Tyr Ala Ser Lys Asp Ser Leu Thr Leu Thr Tyr Gly Ser Asp Asn
            435                 440                 445
Tyr Lys Asn Val Ile Lys Ser Leu Leu Gln Phe Gly Asp Ser Phe Leu
    450                 455                 460
Lys Val Leu Leu Asp His Ile Asp Asp Asn Gly Gln Leu Thr Glu Glu
465                 470                 475                 480
Ile Asn Arg Tyr Thr Gly Phe Gln Ala Gly Ala Val Ser Leu Thr Trp
                485                 490                 495
Ser Ser Gly Ser Leu Leu Ser Ala Asn Arg Ala Arg Asn Lys Leu Ile
            500                 505                 510
Glu Leu Leu
        515

<210> SEQ ID NO 5
<211> LENGTH: 1548
<212> TYPE: DNA
<213> ORGANISM: Artificial Sequence
<220> FEATURE:
<223> OTHER INFORMATION: Codon-optimized sequence for expressing SEQ ID
      NO: 1 in S. cerevisiae

<400> SEQUENCE: 5
atgatcagat tgaccgtttt cttgaccgct gttttgctg ctgttgcttc ttgtgttcca      60
gttgaattgg ataagagaaa caccggtcat tccaagctt attctggtta taccgttgct     120
agatctaact tcacccaatg gattcatgaa caaccagctg tttcttggta ctacttgttg     180
caaaacatcg attacccaga aggtcaattc aaatctgcta accaggtgt tgttgttgct     240 tctccatcta catctgaacc agattacttc taccaatgga ctagagatac cgctattacc     300
ttcttgtcct tgattgctga agttgaagat cattctttct ccaacactac cttggctaag     360
gttgtcgaat attacatttc caacacctac accttgcaaa gagtttctaa tccatccggt     420
aacttcgatt ctccaaatca tgatggtttg ggtgaaccta agttcaacgt tgatgatact     480
gcttatacag cttcttgggg tagaccacaa aatgatggtc cagctttgag agcttacgct     540
atttctagat acttgaacgc tgttgctaag cacaacaacg gtaaattatt attggccggt     600
caaaacggta ttccttattc ttctgcttcc gatatctact ggaagattat taagccagac     660
ttgcaacatg tttctactca ttggtctacc tctggttttg atttgtggga agaaaatcaa     720
ggtactcatt tcttcaccgc tttggttcaa ttgaaggctt gtcttacgg tattccattg     780 tctaagacct acaatgatcc aggtttcact tcttggttgg aaaaacaaaa ggatgccttg     840
aactcctaca ttaactcttc cggtttcgtt aactctggta aaaagcacat cgttgaatct     900
ccacaattgt catctagagg tggtttggat tctgctactt atattgctgc cttgatcacc     960
```

```
catgatatcg gtgatgatga tacttacacc ccattcaatg ttgataactc ctacgttttg    1020
aactccttgt attacctatt ggtcgacaac aagaacagat acaagatcaa cggtaactac    1080
aaagctggtg ctgctgttgg tagatatcct gaagatgttt acaacggtgt tggtacttct    1140
gaaggtaatc catggcaatt ggctactgct tatgctggtc aaacttttta caccttggcc    1200
tacaattcct tgaagaacaa gaagaacttg gtcatcgaaa agttgaacta cgacttgtac    1260
aactccttca ttgctgattt gtccaagatt gattcttcct acgcttctaa ggattctttg    1320
actttgacct acggttccga taactacaag aacgttatca agtccttgtt gcaattcggt    1380
gactcattct tgaaggtttt gttggatcac atcgatgaca acggtcaatt gactgaagaa    1440
atcaacagat acaccggttt tcaagctggt gcagtttctt tgacttggtc atctggttct    1500
ttgttgtctg ctaatagagc cagaaacaag ttgatcgaat tattgtga               1548
```

<210> SEQ ID NO 6
<211> LENGTH: 652
<212> TYPE: PRT
<213> ORGANISM: Bacillus amyloliquefaciens

<400> SEQUENCE: 6

```
Met Leu Leu Gln Ala Phe Leu Phe Leu Leu Ala Gly Phe Ala Ala Lys
1               5                   10                  15

Ile Ser Ala Gly Pro Ala Ala Asn Ala Glu Thr Ala Asn Lys Ser
            20                  25                  30

Asn Lys Val Thr Ala Ser Ser Val Lys Asn Gly Thr Ile Leu His Ala
        35                  40                  45

Trp Asn Trp Ser Phe Asn Thr Leu Thr Gln Asn Met Lys Asp Ile Arg
    50                  55                  60

Asp Ala Gly Tyr Ala Ala Ile Gln Thr Ser Pro Ile Asn Gln Val Lys
65                  70                  75                  80

Glu Gly Asn Gln Gly Asp Lys Ser Met Arg Asn Trp Tyr Trp Leu Tyr
                85                  90                  95

Gln Pro Thr Ser Tyr Gln Ile Gly Asn Arg Tyr Leu Gly Thr Glu Gln
            100                 105                 110

Glu Phe Lys Asp Met Cys Ala Ala Ala Glu Lys Tyr Gly Val Lys Val
        115                 120                 125

Ile Val Asp Ala Val Ile Asn His Thr Thr Ser Asp Tyr Gly Ala Ile
    130                 135                 140

Ser Asp Glu Ile Lys Arg Ile Pro Asn Trp Thr His Gly Asn Thr Gln
145                 150                 155                 160

Ile Lys Asn Trp Ser Asp Arg Trp Asp Val Thr Gln Asn Ser Leu Leu
                165                 170                 175

Gly Leu Tyr Asp Trp Asn Thr Gln Asn Thr Glu Val Gln Val Tyr Leu
            180                 185                 190

Lys Arg Phe Leu Glu Arg Ala Leu Asn Asp Gly Ala Asp Gly Phe Arg
        195                 200                 205

Tyr Asp Ala Ala Lys His Ile Glu Leu Pro Asp Asp Gly Asn Tyr Gly
    210                 215                 220

Ser Gln Phe Trp Pro Asn Ile Thr Asn Thr Ser Ala Glu Phe Gln Tyr
225                 230                 235                 240

Gly Glu Ile Leu Gln Asp Ser Ala Ser Arg Asp Thr Ala Tyr Ala Asn
                245                 250                 255

Tyr Met Asn Val Thr Ala Ser Asn Tyr Gly His Ser Ile Arg Ser Ala
            260                 265                 270
```

```
Leu Lys Asn Arg Asn Leu Ser Val Ser Asn Ile Ser His Tyr Ala Ser
            275                 280                 285

Asp Val Ser Ala Asp Lys Leu Val Thr Trp Val Glu Ser His Asp Thr
        290                 295                 300

Tyr Ala Asn Asp Asp Glu Glu Ser Thr Trp Met Ser Asp Asp Asp Ile
305                 310                 315                 320

Arg Leu Gly Trp Ala Val Ile Gly Ser Arg Ser Gly Ser Thr Pro Leu
                325                 330                 335

Phe Phe Ser Arg Pro Glu Gly Gly Asn Gly Val Arg Phe Pro Gly
                340                 345                 350

Lys Ser Gln Ile Gly Asp Arg Gly Ser Ala Leu Phe Lys Asp Gln Ala
                355                 360                 365

Ile Thr Ala Val Asn Thr Phe His Asn Val Met Ala Gly Gln Pro Glu
        370                 375                 380

Glu Leu Ser Asn Pro Asn Gly Asn Asn Gln Val Phe Met Asn Gln Arg
385                 390                 395                 400

Gly Ser Lys Gly Val Val Leu Ala Asn Ala Gly Ser Ser Val Thr
                405                 410                 415

Ile Asn Thr Ser Ala Lys Leu Pro Asp Gly Arg Tyr Asp Asn Arg Ala
                420                 425                 430

Gly Ala Gly Ser Phe Gln Val Ala Asn Gly Lys Leu Thr Gly Thr Ile
                435                 440                 445

Asn Ala Arg Ser Ala Ala Val Leu Tyr Pro Asp Asp Ile Gly Asn Ala
        450                 455                 460

Pro His Val Phe Leu Glu Asn Tyr Gln Thr Gly Ala Val His Ser Phe
465                 470                 475                 480

Asn Asp Gln Leu Thr Val Thr Leu Arg Ala Asn Ala Lys Thr Thr Lys
                485                 490                 495

Ala Val Tyr Gln Ile Asn Asn Gly Gln Gln Thr Ala Phe Lys Asp Gly
                500                 505                 510

Asp Arg Leu Thr Ile Gly Lys Gly Asp Pro Ile Gly Thr Thr Tyr Asn
            515                 520                 525

Ile Lys Leu Thr Gly Thr Asn Gly Glu Gly Ala Ala Arg Thr Gln Glu
        530                 535                 540

Tyr Thr Phe Val Lys Lys Asp Pro Ser Gln Thr Asn Ile Ile Gly Tyr
545                 550                 555                 560

Gln Asn Pro Asp His Trp Gly Gln Val Asn Ala Tyr Ile Tyr Lys His
                565                 570                 575

Asp Gly Gly Arg Ala Ile Glu Leu Thr Gly Ser Trp Pro Gly Lys Ala
                580                 585                 590

Met Thr Lys Asn Ala Asn Gly Met Tyr Thr Leu Thr Leu Pro Glu Asn
            595                 600                 605

Thr Asp Thr Ala Asn Ala Lys Val Ile Phe Asn Asn Gly Ser Ala Gln
        610                 615                 620

Val Pro Gly Gln Asn Gln Pro Gly Phe Asp Tyr Val Gln Asn Gly Leu
625                 630                 635                 640

Tyr Asn Asn Ser Gly Leu Asn Gly Tyr Leu Pro His
                645                 650

<210> SEQ ID NO 7
<211> LENGTH: 652
<212> TYPE: PRT
<213> ORGANISM: Artificial Sequence
<220> FEATURE:
```

<223> OTHER INFORMATION: MP775

<400> SEQUENCE: 7

```
Met Leu Leu Gln Ala Phe Leu Phe Leu Leu Ala Gly Phe Ala Ala Lys
1               5                   10                  15

Ile Ser Ala Gly Pro Ala Ala Asn Ala Glu Thr Ala Asn Lys Ser
            20                  25                  30

Asn Asn Val Thr Ala Ser Ser Val Lys Asn Gly Thr Ile Leu His Ala
            35                  40                  45

Trp Asn Trp Ser Phe Asn Thr Leu Thr Gln Asn Met Lys Asp Ile Arg
    50                  55                  60

Asp Ala Gly Tyr Ala Ala Ile Gln Thr Ser Pro Ile Asn Gln Val Lys
65                  70                  75                  80

Glu Gly Asn Gln Gly Asp Lys Ser Met Arg Asn Trp Tyr Trp Leu Tyr
                85                  90                  95

Gln Pro Thr Ser Tyr Gln Ile Gly Asn Arg Tyr Leu Gly Thr Glu Gln
            100                 105                 110

Glu Phe Lys Asp Met Cys Ala Ala Ala Glu Lys Tyr Gly Val Lys Val
        115                 120                 125

Ile Val Asp Ala Val Ile Asn His Thr Thr Ser Asp Tyr Gly Ala Ile
130                 135                 140

Ser Asp Glu Ile Lys Arg Ile Pro Asn Trp Thr His Gly Asn Thr Gln
145                 150                 155                 160

Ile Lys Asn Trp Ser Asp Arg Trp Asp Val Thr Gln Asn Ser Leu Leu
                165                 170                 175

Gly Leu Tyr Asp Trp Asn Thr Gln Asn Thr Glu Val Gln Val Tyr Leu
            180                 185                 190

Lys Arg Phe Leu Glu Arg Ala Leu Asn Asp Gly Ala Asp Gly Phe Arg
        195                 200                 205

Tyr Asp Ala Ala Lys His Ile Glu Leu Pro Asp Asp Gly Asn Tyr Gly
210                 215                 220

Ser Gln Phe Trp Pro Asn Ile Thr Asn Thr Ser Ala Glu Phe Gln Tyr
225                 230                 235                 240

Gly Glu Ile Leu Gln Asp Ser Ala Ser Arg Asp Thr Ala Tyr Ala Asn
                245                 250                 255

Tyr Met Asn Val Thr Ala Ser Asn Tyr Gly His Ser Ile Arg Ser Ala
            260                 265                 270

Leu Lys Asn Arg Asn Leu Ser Val Ser Asn Ile Ser His Tyr Ala Ser
        275                 280                 285

Asp Val Ser Ala Asp Lys Leu Val Thr Trp Val Glu Ser His Asp Thr
290                 295                 300

Tyr Ala Asn Asp Asp Glu Glu Ser Thr Trp Met Ser Asp Asp Asp Ile
305                 310                 315                 320

Arg Leu Gly Trp Ala Val Ile Gly Ser Arg Ser Gly Ser Thr Pro Leu
                325                 330                 335

Phe Phe Ser Arg Pro Glu Gly Gly Gly Asn Gly Val Arg Phe Pro Gly
            340                 345                 350

Lys Ser Gln Ile Gly Asp Arg Gly Ser Ala Leu Phe Lys Asp Gln Ala
        355                 360                 365

Ile Thr Ala Val Asn Thr Phe His Asn Val Met Ala Gly Gln Pro Glu
370                 375                 380

Glu Leu Ser Asn Pro Asn Gly Asn Asn Gln Val Phe Met Asn Gln Arg
385                 390                 395                 400
```

```
Gly Ser Lys Gly Val Leu Ala Asn Ala Gly Ser Ser Val Thr
            405                 410                 415

Ile Asn Thr Ser Ala Lys Leu Pro Asp Gly Arg Tyr Asp Asn Arg Ala
        420                 425                 430

Gly Ala Gly Ser Phe Gln Val Ala Asn Gly Lys Leu Thr Gly Thr Ile
            435                 440                 445

Asn Ala Arg Ser Ala Ala Val Leu Tyr Pro Asp Asp Ile Gly Asn Ala
        450                 455                 460

Pro His Val Phe Leu Glu Asn Tyr Gln Thr Gly Ala Val His Ser Phe
465                 470                 475                 480

Asn Asp Gln Leu Thr Val Thr Leu Arg Ala Asn Ala Lys Thr Thr Lys
                485                 490                 495

Ala Val Tyr Gln Ile Asn Asn Gly Gln Gln Thr Ala Phe Lys Asp Gly
            500                 505                 510

Asp Arg Leu Thr Ile Gly Lys Gly Asp Pro Ile Gly Thr Thr Tyr Asn
        515                 520                 525

Ile Lys Leu Thr Gly Thr Asn Gly Glu Gly Ala Ala Arg Thr Gln Glu
    530                 535                 540

Tyr Thr Phe Val Lys Lys Asp Pro Ser Gln Thr Asn Ile Ile Gly Tyr
545                 550                 555                 560

Gln Asn Pro Asp His Trp Gly Gln Val Asn Ala Tyr Ile Tyr Lys His
                565                 570                 575

Asp Gly Gly Arg Ala Ile Glu Leu Thr Gly Ser Trp Pro Gly Lys Ala
            580                 585                 590

Met Thr Lys Asn Ala Asn Gly Met Tyr Thr Leu Thr Leu Pro Glu Asn
        595                 600                 605

Thr Asp Thr Ala Asn Ala Lys Val Ile Phe Asn Asn Gly Ser Ala Gln
    610                 615                 620

Val Pro Gly Gln Asn Gln Pro Gly Phe Asp Tyr Val Gln Asn Gly Leu
625                 630                 635                 640

Tyr Asn Asn Ser Gly Leu Asn Gly Tyr Leu Pro His
                645                 650

<210> SEQ ID NO 8
<211> LENGTH: 499
<212> TYPE: DNA
<213> ORGANISM: Artificial Sequence
<220> FEATURE:
<223> OTHER INFORMATION: tef2p

<400> SEQUENCE: 8
gggcgccata accaaggtat ctatagaccg ccaatcagca aactacctcc gtacattcct      60
gttgcaccca cacatttata cacccagacc gcgacaaatt acccataagg ttgtttgtga     120
cggcgtcgta caagagaacg tgggaacttt ttaggctcac caaaaaagaa aggaaaaata     180
cgagttgctg acagaagcct caagaaaaaa aaaattcttc ttcgactatg ctggagccag     240
agatgatcga gccggtagtt aactatatat agctaaattg gttccatcac cttcttttct     300
ggtgtcgctc cttctagtgc tatttctggc ttttcctatt ttttttttc cattttcttt      360 tctctctttc taatatataa attctcttgc attttctatt tttctctcta tctattctac     420
ttgtttattc ccttcaaggt tttttttaag gactacttgt ttttagaata tacggtcaac     480
gaactataat taactaaac                                                  499

<210> SEQ ID NO 9
<211> LENGTH: 750
```

```
<212> TYPE: DNA
<213> ORGANISM: Artificial Sequence
<220> FEATURE:
<223> OTHER INFORMATION: tdh1p

<400> SEQUENCE: 9
agaaacgaat gtatatgctc atttacactc tatatcacca tatggaggat aagttgggct      60
gagcttctga tccaatttat tctatccatt agttgctgat atgtcccacc agccaacact     120
tgatagtatc tactcgccat tcacttccag cagcgccagt agggttgttg agcttagtaa     180
aaatgtgcgc accacaagcc tacatgactc cacgtcacat gaaaccacac cgtggggcct     240
tgttacgcta ggaataggat atgcgacgaa gacgcttctg cttagtaacc acaccacatt     300
ttcaaggggt cgatctgctt gcttccttta ctgtcacgag cggcccataa tcgcgctttt     360
tttttaaaat gcgcgagaca gcaaacagga agctcgggtt tcaaccttcg gagtggtcgc     420
agatctggag actggatcct tacaatacag taaggcaagc caccatctgc ttcttaggtg     480
catgcgacgg tatccacgtg cagaacaaca tagtctgaag aaggggggga ggagcatgtt     540
cattctctgt agcactaaga gcttggtgat aatgaccaaa actggagtct cgaaatcata     600
taaatagaca atatattttc acacaatgtg atttgtagta cagttctact ctctctcttg     660
cataaataag aaattcatca agaacttggt ttgatatttc accaacacac acaaaaaaca     720
gtacttcact aaatttacac acaaaacaaa                                      750

<210> SEQ ID NO 10
<211> LENGTH: 750
<212> TYPE: DNA
<213> ORGANISM: Artificial Sequence
<220> FEATURE:
<223> OTHER INFORMATION: pau5p

<400> SEQUENCE: 10
atacgaatca gatactgttc ggtacacgat atctaattaa aatgattcaa aactttgtaa      60
caggtaaagt tttcactaga accaatcaat ccaagtgaat taggggaaac catagttgtt     120
gatttgtaga aacctcacat tgtacattgt tggtttgttg ggcatatcag aacgagagat     180
tttccaacat tcaatataca ctaaacccta tgacgagtcc cacagatggc gtaaggtttt     240
tatgatttca gcagggtacg acgactagta ccatattaac atttttttagt gtttctaatt     300
tgggaaaagg tccgtgtttt ttctcctagc aaccgtttag tgccaagggt taggcaattg     360
aacgaggcca agacaatatt ggctttgctt ctattacttg gctaacattg tgtctgcagg     420
tcgaaaggca cctttactgt aaggaacatt cttgcgctct aaacatacga agatatgggg     480
aatatgaagc gtgtttctta tacgaagtgc agcatcgttc aaggaaaata catccccata     540
gtaataatgg ctaagtggcc aggaattaga atatgtgaga tatgagtgca aaatgagtga     600
ccagtaatag cctgtttggg atgtaattgc tcaaaaaatt tatataaata cagcggtttg     660
atcagctttg tttgagacat ttctctgttc ttttccttcc agttaagctt atatctccac     720
taagcaacaa cccaaaaaac aacaaataca                                      750

<210> SEQ ID NO 11
<211> LENGTH: 750
<212> TYPE: DNA
<213> ORGANISM: Artificial Sequence
<220> FEATURE:
<223> OTHER INFORMATION: anb1p

<400> SEQUENCE: 11
```

```
gttgcctggc catccacgct atatatacac gcctggcgga tctgctcgag gattgcctac    60
gcgtgggctt gatccaccaa ccaacgctcg ccaaatgaac tggcgctttg gtcttctgcc   120
atcgtccgta aaccccggcc aaagagaccg gaaagatcgg tgaaaacatc ttgatcttgc   180
tcccgggaat tttagattca ggtaggaaat tgattacatc aatactgtta ccctgaatca   240
tattcgacga tgtcgtctca cacggaaata taattcattt cttggttttc caaaaaaatt   300
ttcatttttt ttcactttt tgtttcgtcc tcctttttt ttttttgttt tattttttgt   360
cctgtgttca cctttttttt tttcagttta catctttctg cattcttttc tgtgtttttt   420
tttttttttc gttttccat tgttcgttcg ttgcctgttt tttcgcccta ttgttctcga   480
gcctaaaaat tttttccttt cctgctttcc tttcttcgtt caaagtttcc tattccattg   540
ttctctttgg taaactcatt gttgtcggaa ctcagatata ttcaggtcaa tttactgtac   600
ttcaattgac tttttttcttg aaatttcaac ttgcctttc aacttgttct tctttttaa   660 tcttattcta cactttagtt cccttacctt gttcctaatt attgtctagc aaaaagaaaa   720
catacaccta tttcattcac acactaaaac                                    750

<210> SEQ ID NO 12
<211> LENGTH: 750
<212> TYPE: DNA
<213> ORGANISM: Artificial Sequence
<220> FEATURE:
<223> OTHER INFORMATION: hor7p

<400> SEQUENCE: 12
acctccatga aatttttttt tttcttcga ttagcacgca cacacatcac atagactgcg    60
tcataaaaat acactacgga aaaaccataa agagcaaagc gatacctact tggaaggaaa   120
aggagcacgc ttgtaagggg gatgggggct aagaagtcat tcactttctt ttcccttcgc   180
ggtccggacc cgggaccccct cctctccccg cacaatttct tcctttcata tcttcctttt   240
attcctatcc cgttgaagca accgcactat gactaaatgg tgctggacat ctccatggct   300
gtgacttgtg tgtatctcac agtggtaacg gcaccgtggc tcggaaacgg ttccttcgtg   360
acaattctag aacaggggct acagtctcga taatagaata ataagcgcat ttttgttagc   420
gccgccgcgg cgcccgtttc ccaatagggga ggcgcagttt atcggcggag ctttacttct   480
tcctatttgg gtaagcccct ttctgttttc ggccagtggt tgctgcaggc tgcgccggag   540
aacatagtga taagggatgt aactttcgat gagagaatta gcaagcggaa aaaaaactat   600
ggctagctgg gagttgtttt tcaatcatat aaaaggaga aattgttgct cactatgtga   660
cagtttctgg gacgtcttaa cttttattgc agaggactat caaatcatac agatattgtc   720
aaaaaaaaaa aaaagactca ataataaaaa                                    750

<210> SEQ ID NO 13
<211> LENGTH: 749
<212> TYPE: DNA
<213> ORGANISM: Artificial Sequence
<220> FEATURE:
<223> OTHER INFORMATION: adh1p

<400> SEQUENCE: 13
cgattttttt ctaaaccgtg gaatatttcg gatatccttt tgttgtttcc gggtgtacaa    60
tatggacttc ctcttttctg gcaaccaaac ccatacatcg ggattcctat aataccttcg   120
ttggtctccc taacatgtag gtggcggagg ggagatatac aatagaacag ataccagaca   180
agacataatg ggctaaacaa gactacacca attacactgc ctcattgatg gtggtacata   240
```

```
acgaactaat actgtagccc tagacttgat agccatcatc atatcgaagt ttcactaccc    300
tttttccatt tgccatctat tgaagtaata ataggcgcat gcaacttctt ttcttttttt    360
ttcttttctc tctcccccgt tgttgtctca ccatatccgc aatgacaaaa aaatgatgga    420
agacactaaa ggaaaaaatt aacgacaaag acagcaccaa cagatgtcgt tgttccagag    480
ctgatgaggg gtatctcgaa gcacacgaaa cttttccctt ccttcattca cgcacactac    540
tctctaatga gcaacggtat acggccttcc ttccagttac ttgaatttga aataaaaaaa    600
gtttgctgtc ttgctatcaa gtataaatag acctgcaatt attaatcttt tgtttcctcg    660
tcattgttct cgttcccttt cttccttgtt tcttttctg cacaatattt caagctatac    720
caagcataca atcaactatc tcatataca                                      749
```

<210> SEQ ID NO 14
<211> LENGTH: 750
<212> TYPE: DNA
<213> ORGANISM: Artificial Sequence
<220> FEATURE:
<223> OTHER INFORMATION: tdh2p

<400> SEQUENCE: 14

```
tggaaagtac caacatcggt tgaaacagtt tttcatttac atatggttta ttggtttttc     60
cagtgaatga ttatttgtcg ttacccttc gtaaagttc aaacacgttt ttaagtattg     120
tttagttgct ctttcgacat atatgattat ccctgcgcgg ctaaagttaa ggatgcaaaa    180
aacataagac aactgaagtt aatttacgtc aattaagttt tccagggtaa tgatgttttg    240
ggcttccact aattcaataa gtatgtcatg aaatacgttg tgaagagcat ccagaaataa    300
tgaaaagaaa caacgaaact gggtcggcct gttgtttctt ttctttacca cgtgatctgc    360
gccatttaca ggaagtcgcg cgttttgcgc agttgttgca acgcagctac ggctaacaaa    420
gcctagtgga actcgactga tgtgttaggg cctaaaactg gtggtgacag ctgaagtgaa    480
ctattcaatc caatcatgtc atggctgtca caaagacctt gcggaccgca cgtacgaaca    540
catacgtatg ctaatatgtg ttttgatagt acccagtgat cgcagacctg caatttttt     600 gtaggtttgg aagaatatat aaaggttgca ctcattcaag atagttttt tcttgtgtgt    660 ctattcacat tattttttt ttgattaaat gttaaaaaa ccagaacctt agtttcaaat    720
taaattcatc acacaaacaa acaaaacaaa                                      750
```

<210> SEQ ID NO 15
<211> LENGTH: 750
<212> TYPE: DNA
<213> ORGANISM: Artificial Sequence
<220> FEATURE:
<223> OTHER INFORMATION: tdh3p

<400> SEQUENCE: 15

```
ggccaaggca aaagattcc ttgattacgt aagggagtta gaatcatttt gaataaaaaa      60
cacgcttttt cagttcgagt ttatcattat caatactgcc atttcaaaga atacgtaaat    120
aattaatagt agtgattttc ctaactttat ttagtcaaaa aattagcctt ttaattctgc    180
tgtaacccgt acatgcccaa ataggggggc gggttacaca gaatatataa catcataggt    240
gtctgggtga acagtttatt cctggcatcc actaaatata atggagcccg ttttttaagc    300
tggcatccag aaaaaaaaag aatcccagca ccaaatatt gttttcttca ccaaccatca    360
gttcataggt ccattctctt agcgcaacta cagagaacag gggcacaaac aggcaaaaaa    420
```

| cgggcacaac | ctcaatggag | tgatgcaacc | tgcctggagt | aaatgatgac | acaaggcaat | 480 |
| tgacccacgc | atgtatctat | ctcattttct | tacaccttct | attaccttct | gctctctctg | 540 |
| atttggaaaa | agctgaaaaa | aaaggttgaa | accagttccc | tgaaattatt | ccctacttg  | 600 |
| actaataagt | atataaagac | ggtaggtatt | gattgtaatt | ctgtaaatct | atttcttaaa | 660 |
| cttcttaaat | tctacttta  | gagttagtct | ttttttagt  | tttaaaacac | caagaactta | 720 |
| gtttcgaata | aacacacata | aacaaacaaa |            |            |            | 750 |

<210> SEQ ID NO 16
<211> LENGTH: 750
<212> TYPE: DNA
<213> ORGANISM: Artificial Sequence
<220> FEATURE:
<223> OTHER INFORMATION: gpd1p

<400> SEQUENCE: 16

| aaggaaaata | tatactcttt | cccaggcaag | gtgacagcgg | tccccgtctc | ctccacaaag | 60  |
| gcctctcctg | gggtttgagc | aagtctaagt | ttacgtagca | taaaaattct | cggattgcgt | 120 |
| caaataataa | aaaagtaac  | tccacttcta | cttctacatc | ggaaaaacat | tccattcaca | 180 |
| tatcgtcttt | ggcctatctt | gttttgtcct | tggtagatca | ggtcagtaca | aacgcaacac | 240 |
| gaaagaacaa | aaaagaaga  | aaaacagaag | gccaagacag | ggtcaatgag | actgttgtcc | 300 |
| tcctactgtc | cctatgtctc | tggccgatca | cgcgccattg | tccctcagaa | acaaatcaaa | 360 |
| cacccacacc | ccgggcaccc | aaagtcccca | cccacaccac | caatacgtaa | acggggcgcc | 420 |
| ccctgcaggc | cctcctgcgc | gcggcctccc | gccttgcttc | tctcccctcc | cttttctttt | 480 |
| tccagttttc | cctattttgt | ccctttttcc | gcacaacaag | tatcagaatg | ggttcatcaa | 540 |
| atctatccaa | cctaattcgc | acgtagactg | gcttggtatt | ggcagtttcg | cagttatata | 600 |
| tatactacca | tgagtgaaac | tgttacgtta | ccttaaattc | tttctcccttt| taattttctt | 660 |
| ttatcttact | ctcctacata | agacatcaag | aaacaattgt | atattgtaca | ccccccccc  | 720 |
| tccacaaaca | caaatattga | taatataaag |            |            |            | 750 |

<210> SEQ ID NO 17
<211> LENGTH: 750
<212> TYPE: DNA
<213> ORGANISM: Artificial Sequence
<220> FEATURE:
<223> OTHER INFORMATION: cdc19p

<400> SEQUENCE: 17

| tttttccggc | agaaagattt | tcgctacccg | aaagtttttc | cggcaagcta | aatggaaaaa | 60  |
| ggaaagatta | ttgaaagaga | aagaaagaaa | aaaaaaatgt | acacccagac | atcgggcttc | 120 |
| cacaatttcg | gctctattgt | tttccatctc | tcgcaacggc | gggattcctc | tatggcgtgt | 180 |
| gatgtctgta | tctgttactt | aatccagaaa | ctggcacttg | acccaactct | gccacgtggg | 240 |
| tcgttttgct | atcgacagat | tgggagatgt | tcatagtaga | gttcagcatg | atagctacgt | 300 |
| aaatgtgttc | cgcaccgtca | caaagtgttt | tctactgttc | tttcttcttt | cgttcattca | 360 |
| gttaagttga | gtgagtgctt | tgttcaatgg | atcttagcta | aaatgcatat | ttttctctct | 420 |
| ggtaaatgaa | tgcttgtgat | gtcttccaag | tgatttcctt | tccttcccat | atgatgctag | 480 |
| gtacctttag | tgtcttcctg | aaaaaaaagg | ctcgccatca | aaacgatatt | cgttggcttt | 540 |
| tttttctgaa | ttataaatac | tctttagtaa | cttttccattt| tcaagaacct | cttttttcca | 600 |
| gttatatcat | ggtccccttt | caaagttatt | ctctactctt | tttcatattc | attctttttc | 660 |

```
atcctttggt tttttattct taacttgttt attattctct cttgtttcta tttacaagac    720
accaatcaaa acaaataaaa catcatcaca                                     750
```

<210> SEQ ID NO 18
<211> LENGTH: 750
<212> TYPE: DNA
<213> ORGANISM: Artificial Sequence
<220> FEATURE:
<223> OTHER INFORMATION: eno2p

<400> SEQUENCE: 18

```
aagatgttgg ttaccaagaa gatgccgccc tggaattaat tcagaagctg attgaataca     60
ttagcaacgc gtccagcatt tttcggaagt gtctcataaa ctttactcaa gagttaagta    120
ctgaaaaatt cgactttat gatagttcaa gtgtcgacgc tgcgggtata gaaagggttc    180
tttactctat agtgcctcct cgctcagcat ctgcttcttc ccaaagatga acgcggcgtt    240
atgtcactaa cgacgtgcac cattttttgcg gaaagtggaa tcccgttcca aaactggcat    300
ccactaattg atacatctac acaccgcacg ccttttttct gaagcccact ttcgtggact    360
ttgccatatg caaaattcat gaagtgtgat accaagtcag catacacctc actagggtag    420
tttctttggt tgtattgatc atttggttca tcgtggttca ttaattttttt ttctccattg    480 ctttctggct tgatcttac tatcatttgg attttttgtcg aaggttgtag aattgtatgt    540
gacaagtggc accaagcata tataaaaaaa aaagcattat cttcctacca gagttaattg    600
ttaaaaacgt atttatagca aacgcaattg taattaattc ttattttgta tctttttcttc    660 ccttgtctca atctttttatt tttattttat ttttctttttc ttagtttctt tcataacacc    720
aagcaactaa tactataaca tacaataata                                     750
```

<210> SEQ ID NO 19
<211> LENGTH: 750
<212> TYPE: DNA
<213> ORGANISM: Artificial Sequence
<220> FEATURE:
<223> OTHER INFORMATION: pdc1p

<400> SEQUENCE: 19

```
aagcaaggca gaaactaact tcttcttcat gtaataaaca cacccccgcgt ttatttacct     60 atctttaaac ttcaacacct tatatcataa ctaatatttc ttgagataag cacactgcac    120
ccataccttc cttaaaaacg tagcttccag ttttttggtgg ttccggcttc cttcccgatt    180
ccgcccgcta aacgcatatt tttgttgcct ggtggcattt gcaaaatgca taacctatgc    240
atttaaaaga ttatgtatgc tcttctgact tttcgtgtga tgaggctcgt ggaaaaaatg    300
aataatttat gaatttgaga acaatttttgt gttgttacgg tatttttacta tggaataatc    360 aatcaattga ggattttatg caaatatcgt ttgaatatttt ttccgacccct ttgggtactt    420 ttcttcataa ttgcataata ttgtccgctg ccccttttttc tgttagacgg tgtcttgatc    480
tacttgctat cgttcaacac caccttattt tctaactatt tttttttttag ctcatttgaa    540 tcagcttatg gtgatggcac atttttttgcat aaacctagct gtcctcgttg aacataggaa    600
aaaaaaatat ataaacaagg ctctttcact ctccttgcaa tcagatttgg gtttgttccc    660
tttattttca tatttcttgt catattcctt tctcaattat tattttctac tcataacctc    720
acgcaaaata acacagtcaa atcaatcaaa                                     750
```

<210> SEQ ID NO 20

<211> LENGTH: 750
<212> TYPE: DNA
<213> ORGANISM: Artificial Sequence
<220> FEATURE:
<223> OTHER INFORMATION: hxt3p

<400> SEQUENCE: 20

```
gccttcatct tctcgagata acacctggag gaggagcaat gaaatgaaag gaaaaaaaaa    60
aatactttct ttttcttgaa aaagaaaaa aattgtaaga tgagctattc gcggaacatt    120
ctagctcgtt tgcatcttct tgcatttggt tggttttcaa tacttgggta atattaacgg   180
atacctacta ttatcccta gtaggctctt ttcacggaga aattcgggag tgcttttttt   240
ccgtgcgcat tttcttagct atattcttcc agcttcgcct gctgcccggt catcgttcct   300
gtcacgtagt ttttccggat tcgtccggct catataatac cgcaataaac acggaatatc   360
tcgttccgcg gattcggtta aactctcggt cgcggattat cacagagaaa gcttcgtgga   420
gaattttttcc agattttccg ctttccccga tgttggtatt tccggaggtc attatactga   480
ccgccattat aatgactgta caacgacctt ctggagaaag aaacaactca ataacgatgt   540
gggacattgg aggcccactc aaaaaatctg gggactatat ccccagagaa tttctccaga   600
agagaagaaa gtcaaagttt ttttcacttg ggggttgcat ataaatacag gcgctgtttt   660
atcttcagca tgaatattcc ataagtttac ttaatagctt ttcataaata atagaatcac   720
aaacaaaatt tacatctgag ttaaacaatc                                     750
```

<210> SEQ ID NO 21
<211> LENGTH: 450
<212> TYPE: DNA
<213> ORGANISM: Artificial Sequence
<220> FEATURE:
<223> OTHER INFORMATION: tpi1

<400> SEQUENCE: 21

```
ctacttattc ccttcgagat tatatctagg aacccatcag gttggtggaa gattacccgt    60
tctaagactt ttcagcttcc tctattgatg ttacacctgg acacccctttt tctggcatcc   120
agttttttaat cttcagtggc atgtgagatt ctccgaaatt aattaaagca atcacacaat   180
tctctcggat accacctcgg ttgaaactga caggtggttt gttacgcatg ctaatgcaaa   240
ggagcctata tacctttggc tcggctgctg taacagggaa tataaaggc agcataattt   300
aggagtttag tgaacttgca acatttacta ttttcccttc ttacgtaaat attttttcttt   360
ttaattctaa atcaatcttt ttcaattttt tgtttgtatt cttttcttgc ttaaatctat   420
aactacaaaa aacacataca taaactaaaa                                     450
```

<210> SEQ ID NO 22
<211> LENGTH: 30
<212> TYPE: DNA
<213> ORGANISM: Artificial Sequence
<220> FEATURE:
<223> OTHER INFORMATION: Primer sequence X28001

<400> SEQUENCE: 22

```
ctgactcgtt ggtgggtcc acaccataga                                      30
```

<210> SEQ ID NO 23
<211> LENGTH: 24
<212> TYPE: DNA
<213> ORGANISM: Artificial Sequence
<220> FEATURE:
<223> OTHER INFORMATION: Primer sequence X27580

-continued

<400> SEQUENCE: 23
tagctatgaa atttttaact cttc                                    24

<210> SEQ ID NO 24
<211> LENGTH: 35
<212> TYPE: DNA
<213> ORGANISM: Artificial Sequence
<220> FEATURE:
<223> OTHER INFORMATION: Primer sequence X27581

<400> SEQUENCE: 24
agcacgcagc acgctgtatt tacgtattta atttt                        35

<210> SEQ ID NO 25
<211> LENGTH: 60
<212> TYPE: DNA
<213> ORGANISM: Artificial Sequence
<220> FEATURE:
<223> OTHER INFORMATION: Primer sequence X27582

<400> SEQUENCE: 25
agccagcttt ttgaagagtt aaaaatttca tagctagggc gccataacca aggtatctat    60

<210> SEQ ID NO 26
<211> LENGTH: 60
<212> TYPE: DNA
<213> ORGANISM: Artificial Sequence
<220> FEATURE:
<223> OTHER INFORMATION: Primer sequence X28015

<400> SEQUENCE: 26
aacagcggtc aagaaaacgg tcaatctgat catgtttagt taattatagt tcgttgaccg    60

<210> SEQ ID NO 27
<211> LENGTH: 60
<212> TYPE: DNA
<213> ORGANISM: Artificial Sequence
<220> FEATURE:
<223> OTHER INFORMATION: Primer sequence X20072

<400> SEQUENCE: 27
aatatacggt caacgaacta taattaacta aacatgatca gattgaccgt tttcttgacc    60

<210> SEQ ID NO 28
<211> LENGTH: 60
<212> TYPE: DNA
<213> ORGANISM: Artificial Sequence
<220> FEATURE:
<223> OTHER INFORMATION: Primer sequence X20071

<400> SEQUENCE: 28
agactttcat aaaaagtttg ggtgcgtaac acgctatcac aataattcga tcaacttgtt    60

<210> SEQ ID NO 29
<211> LENGTH: 60
<212> TYPE: DNA
<213> ORGANISM: Artificial Sequence
<220> FEATURE:
<223> OTHER INFORMATION: Primer sequence X31384

<400> SEQUENCE: 29
gctaatagag ccagaaacaa gttgatcgaa ttattgtgat agcgtgttac gcacccaaac    60

<210> SEQ ID NO 30

```
<211> LENGTH: 60
<212> TYPE: DNA
<213> ORGANISM: Artificial Sequence
<220> FEATURE:
<223> OTHER INFORMATION: Primer sequence X31385

<400> SEQUENCE: 30
aattaaatac gtaaatacag cgtgctgcgt gctatgagga agaaatccaa atcctaatga      60

<210> SEQ ID NO 31
<211> LENGTH: 60
<212> TYPE: DNA
<213> ORGANISM: Artificial Sequence
<220> FEATURE:
<223> OTHER INFORMATION: Primer sequence X26468

<400> SEQUENCE: 31
aattaaatac gtaaatacag cgtgctgcgt gctatgagga agaaatccaa atcctaatga      60

<210> SEQ ID NO 32
<211> LENGTH: 60
<212> TYPE: DNA
<213> ORGANISM: Artificial Sequence
<220> FEATURE:
<223> OTHER INFORMATION: Primer sequence X27405

<400> SEQUENCE: 32 ccagctttttt gaagagttaa aaatttcata gctaagaaac gaatgtatat gctcatttac     60

<210> SEQ ID NO 33
<211> LENGTH: 60
<212> TYPE: DNA
<213> ORGANISM: Artificial Sequence
<220> FEATURE:
<223> OTHER INFORMATION: Primer sequence X28699

<400> SEQUENCE: 33
aaacagcggt caagaaaacg gtcaatctga tcattttgtt ttgtgtgtaa atttagtgaa      60

<210> SEQ ID NO 34
<211> LENGTH: 60
<212> TYPE: DNA
<213> ORGANISM: Artificial Sequence
<220> FEATURE:
<223> OTHER INFORMATION: Primer sequence X24018

<400> SEQUENCE: 34
acagtacttc actaaattta cacacaaaac aaaatgatca gattgaccgt tttcttgacc     60

<210> SEQ ID NO 35
<211> LENGTH: 59
<212> TYPE: DNA
<213> ORGANISM: Artificial Sequence
<220> FEATURE:
<223> OTHER INFORMATION: Primer sequence X27282

<400> SEQUENCE: 35
gaaaaaaaaa gtggtagatt gggctacgta aattcgatca caataattcg atcaacttg      59

<210> SEQ ID NO 36
<211> LENGTH: 56
<212> TYPE: DNA
<213> ORGANISM: Artificial Sequence
<220> FEATURE:
<223> OTHER INFORMATION: Primer sequence X27283

<400> SEQUENCE: 36
```
gagccagaaa caagttgatc gaattattgt gatcgaattt acgtagccca atctac            56

```
<210> SEQ ID NO 37
<211> LENGTH: 60
<212> TYPE: DNA
<213> ORGANISM: Artificial Sequence
<220> FEATURE:
<223> OTHER INFORMATION: Primer sequence X25154

<400> SEQUENCE: 37
```
tatataaaat taaatacgta aatacagcgt gctgcgtgct caaatgacgt caaaagaagt        60

```
<210> SEQ ID NO 38
<211> LENGTH: 60
<212> TYPE: DNA
<213> ORGANISM: Artificial Sequence
<220> FEATURE:
<223> OTHER INFORMATION: Primer sequence X28017

<400> SEQUENCE: 38
```
gcttgaaggt cattaggatt tggatttctt cctcataaat tagtgtgtgt gcattatata        60

```
<210> SEQ ID NO 39
<211> LENGTH: 25
<212> TYPE: DNA
<213> ORGANISM: Artificial Sequence
<220> FEATURE:
<223> OTHER INFORMATION: Primer sequence X24678

<400> SEQUENCE: 39
```
tcctgttgaa gtagcattta atcat                                             25

```
<210> SEQ ID NO 40
<211> LENGTH: 60
<212> TYPE: DNA
<213> ORGANISM: Artificial Sequence
<220> FEATURE:
<223> OTHER INFORMATION: Primer sequence X20066

<400> SEQUENCE: 40
```
caaaaattat gattaaatgc tacttcaaca ggattacaat aattcgatca acttgtttct        60

```
<210> SEQ ID NO 41
<211> LENGTH: 59
<212> TYPE: DNA
<213> ORGANISM: Artificial Sequence
<220> FEATURE:
<223> OTHER INFORMATION: Primer sequence X19705

<400> SEQUENCE: 41
```
aaaacaaaaa gttttttttaa ttttaatcaa aaaatgatca gattgaccgt tttcttgac       59

```
<210> SEQ ID NO 42
<211> LENGTH: 60
<212> TYPE: DNA
<213> ORGANISM: Artificial Sequence
<220> FEATURE:
<223> OTHER INFORMATION: Primer sequence X27998

<400> SEQUENCE: 42
```
caaaaacagc ggtcaagaaa acggtcaatc tgatcatttt ttgattaaaa ttaaaaaaac        60

```
<210> SEQ ID NO 43
<211> LENGTH: 60
<212> TYPE: DNA
```

```
<213> ORGANISM: Artificial Sequence
<220> FEATURE:
<223> OTHER INFORMATION: Primer sequence X25201

<400> SEQUENCE: 43
aattaaatac gtaaatacag cgtgctgcgt gctccagaaa ggcaacgcaa aattttttt     60

<210> SEQ ID NO 44
<211> LENGTH: 59
<212> TYPE: DNA
<213> ORGANISM: Artificial Sequence
<220> FEATURE:
<223> OTHER INFORMATION: Primer sequence X27379

<400> SEQUENCE: 44
gagccagctt tttgaagagt taaaaatttc atagctaata cgaatcagat actgttcgg      59

<210> SEQ ID NO 45
<211> LENGTH: 60
<212> TYPE: DNA
<213> ORGANISM: Artificial Sequence
<220> FEATURE:
<223> OTHER INFORMATION: Primer sequence X28186

<400> SEQUENCE: 45
caaaaacagc ggtcgagaaa acggtcaatc tgatcattgt atttgttgtt ttttgggttg     60

<210> SEQ ID NO 46
<211> LENGTH: 24
<212> TYPE: DNA
<213> ORGANISM: Artificial Sequence
<220> FEATURE:
<223> OTHER INFORMATION: Primer sequence X25892

<400> SEQUENCE: 46
atgatcagat tgaccgtttt ctcg                                            24

<210> SEQ ID NO 47
<211> LENGTH: 60
<212> TYPE: DNA
<213> ORGANISM: Artificial Sequence
<220> FEATURE:
<223> OTHER INFORMATION: Primer sequence X27996

<400> SEQUENCE: 47
aacaaaaagg tagaccaatg tagcgctctt actttatcac aataattcga tcaacttgtt    60

<210> SEQ ID NO 48
<211> LENGTH: 60
<212> TYPE: DNA
<213> ORGANISM: Artificial Sequence
<220> FEATURE:
<223> OTHER INFORMATION: Primer sequence X27458

<400> SEQUENCE: 48
ctaatagagc cagaaacaag ttgatcgaat tattgtgata aagtaagagc gctacattgg    60

<210> SEQ ID NO 49
<211> LENGTH: 60
<212> TYPE: DNA
<213> ORGANISM: Artificial Sequence
<220> FEATURE:
<223> OTHER INFORMATION: Primer sequence X27812

<400> SEQUENCE: 49
cataggctca tataatactt cttttgacgt catttgaagt gagttctatt cacgcaatcg    60
```

<210> SEQ ID NO 50
<211> LENGTH: 60
<212> TYPE: DNA
<213> ORGANISM: Artificial Sequence
<220> FEATURE:
<223> OTHER INFORMATION: Primer sequence X27811

<400> SEQUENCE: 50
tcttctttga tactaccgat tgcgtgaata gaactcactt caaatgacgt caaagaagt        60

<210> SEQ ID NO 51
<211> LENGTH: 60
<212> TYPE: DNA
<213> ORGANISM: Artificial Sequence
<220> FEATURE:
<223> OTHER INFORMATION: Primer sequence X27995

<400> SEQUENCE: 51
gctaatagag ccagaaacaa gttgatcgaa ttattgtgat cgaatttacg tagcccaatc        60

<210> SEQ ID NO 52
<211> LENGTH: 60
<212> TYPE: DNA
<213> ORGANISM: Artificial Sequence
<220> FEATURE:
<223> OTHER INFORMATION: Primer sequence X28187

<400> SEQUENCE: 52
gcaaaaacag cggtcgagaa aacggtcaat ctgatcattt tgttttgtgt gtaaatttag        60

<210> SEQ ID NO 53
<211> LENGTH: 60
<212> TYPE: DNA
<213> ORGANISM: Artificial Sequence
<220> FEATURE:
<223> OTHER INFORMATION: Primer sequence X28152

<400> SEQUENCE: 53
tatataaaat taaatacgta aatacagcgt gctgcgtgct agaaacgaat gtatatgctc        60

<210> SEQ ID NO 54
<211> LENGTH: 500
<212> TYPE: DNA
<213> ORGANISM: Artificial Sequence
<220> FEATURE:
<223> OTHER INFORMATION: adh3t

<400> SEQUENCE: 54
tagcgtgtta cgcacccaaa cttttttatga aagtctttgt ttataatgat gaggtttata        60
aatatatagt ggagcaaaga ttaatcacta aatcaagaag cagtaccagt attttttta       120 tatcaagtag tgataatgga aatagcccaa atttggcttc cgtcggcaca tagcacgttt       180
gagagacatt atcaccatca agcatcgagc cgcccaaacc taactgtata agttttttca       240 cgttttgat ttttccttgc acacttcgat attactctca cgataaaagg gccgaagaga       300
atatttttct tgaacatcca gaattttaat tcggagaaat ttcacaagcc gccgatttaa       360
gggtcctgtg ttcttaataa tcagcctctc tcaaagcagg taagaggcag tcttctttt       420 aacaatagga gacattcgaa ctaaaacatc agccccaaaa atgcgcttga aggtcattag       480
gatttggatt tcttcctcat                                                   500

<210> SEQ ID NO 55

<211> LENGTH: 500
<212> TYPE: DNA
<213> ORGANISM: Artificial Sequence
<220> FEATURE:
<223> OTHER INFORMATION: idp1t

<400> SEQUENCE: 55

| tcgaatttac | gtagcccaat | ctaccacttt | tttttttcatt | ttttaaagtg | ttatacttag | 60 |
| ttatgctcta | ggataatgaa | ctactttttt | ttttttttac | tgttatcata | aatatatata | 120 |
| ccttattgat | gtttgcaacc | gtcggttaat | tccttatcaa | ggttcccccaa | gttcggatca | 180 |
| ttaccatcaa | tttccaacat | cttcatgagt | tcttcttctt | cattaccgtg | ttttaggggg | 240 |
| ctgttcgcac | ttctaatagg | gctatcacca | agctgttcta | attcgtccaa | aagttcagta | 300 |
| acacgatctt | tatgcttcag | ttcgtcataa | tctttcaatt | cataaatatt | tacaatttcg | 360 |
| tctacgatat | taaattgcct | cttgtaggtg | cctatctttt | ccttatgctc | ttcattttca | 420 |
| ccgttttctt | gaaaccaaac | accgaactca | ctacgcattt | ctttcatagg | ctcatataat | 480 |
| acttcttttg | acgtcatttg | | | | | 500 |

<210> SEQ ID NO 56
<211> LENGTH: 500
<212> TYPE: DNA
<213> ORGANISM: Artificial Sequence
<220> FEATURE:
<223> OTHER INFORMATION: dit1t

<400> SEQUENCE: 56

| taaagtaaga | gcgctacatt | ggtctacctt | tttgttcttt | tacttaaaca | ttagttagtt | 60 |
| cgttttcttt | ttctcatttt | tttatgtttc | ccctcaaaag | ttctgatttt | ataatatttt | 120 |
| atttcacaca | attccaatta | acagaggggg | aatagattct | ttagcttaga | aaattagtga | 180 |
| tcaatatata | tttgcctttc | ttttcatctt | ttcagtgata | ttaatggttt | cgagacactg | 240 |
| caatggccct | agttgtctaa | gaggatagat | gttactgtca | aagatgatat | tttgaatttc | 300 |
| aattgacgta | attaatgata | ctattaataa | tacagagcgt | atatgaagta | ttgcaaataa | 360 |
| catgcacagt | tcttttggga | tgagaatgag | aatgagaggc | gaaggcgggc | gttcagaaaa | 420 |
| gcgttgcgga | gtaacaagtg | attaaatagc | acccaaataa | tcttctttga | actaccgat | 480 |
| tgcgtgaata | gaactcactt | | | | | 500 |

<210> SEQ ID NO 57
<211> LENGTH: 500
<212> TYPE: DNA
<213> ORGANISM: Artificial Sequence
<220> FEATURE:
<223> OTHER INFORMATION: pma1t

<400> SEQUENCE: 57

| tcctgttgaa | gtagcattta | atcataattt | ttgtcacatt | ttaatcaact | tgattttttct | 60 |
| ggtttaattt | ttctaatttt | aattttaatt | tttttatcaa | tgggaactga | tacactaaaa | 120 |
| agaattagga | gccaacaaga | ataagccgct | tatttcctac | tagagtttgc | ttaaaatttc | 180 |
| atctcgaatt | gtcattctaa | tatttttatcc | acacacacac | cttaaaattt | ttagattaaa | 240 |
| tggcatcaac | tcttagcttc | acacacacac | acacaccgaa | gctggttgtt | tatttgatt | 300 |
| tgatataatt | ggtttctctg | gatggtactt | tttcttcctt | ggttatttcc | tattttaaaa | 360 |
| tatgaaacgc | acacaagtca | taattattct | aatagagcac | aattcacaac | acgcacattt | 420 |

```
caactttaat attttttttag aaacactta tttagtctaa ttcttaattt ttaatatata    480
taatgcacac acactaattt                                                 500
```

YEAST STRAINS FOR THE EXPRESSION AND SECRETION OF HETEROLOGOUS PROTEINS AT HIGH TEMPERATURES

CROSS-REFERENCE TO RELATED APPLICATIONS AND DOCUMENTS

This application claims priority from U.S. provisional patent application Ser. No. 62/214,412 filed on Sep. 4, 2015 and 62/299,897 filed on Feb. 25, 2016, both of which are included herewith in their entirety. This application is filed concurrently with a sequence listing in an electronic format. The content of such sequence listing is herewith incorporated in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 580127_401 USPC_SEQUENCE_LISTING.txt. The text file is 55.7 KB, was created on Mar. 1, 2018, and is being submitted electronically via EFS-Web.

TECHNOLOGICAL FIELD

This disclosure relates to the use of recombinant yeasts maintaining high temperature robustness for the expression and secretion of heterologous proteins. The disclosure also relates to the use of such recombinant yeasts and/or the heterologous proteins they express for the hydrolysis of a substrate (such as, for example, a lignocellulosic biomass).

BACKGROUND

*Saccharomyces cerevisiae* is the primary biocatalyst used in the commercial production of fuel ethanol. This organism is proficient in fermenting glucose to ethanol, often to concentrations greater than 20% w/v. However, native *S. cerevisiae* lacks the endogenous ability to hydrolyze polysaccharides and therefore requires the exogenous addition of enzymes (such as, for example α-amylase and glucoamylase when corn is used) to convert complex sugars to glucose. The use of genetically modified *S. cerevisiae* capable of expressing a functional glucoamylase (such as, for example, those described in WO2011153516) is intended to reduce the overall enzyme costs.

However, the overexpression of heterologous proteins in *S. cerevisiae* can cause several stress reactions which can have dramatic effects on overall fermentation performance of the organism. Coupled with the already high stresses of a fermentation process (i.e., high ethanol, temperature, osmotic, pH stress), any metabolic upset can cause detrimental physiological limitations to the host (Gassser et al., 2008; Mattanovich et al., 2004). Any decrease in general fermentation robustness of the yeast can cause detrimental process upsets such as stuck fermentations, depressed kinetics which can lead to contamination, decreased ethanol titers, or high residual sugars which cause many downstream process issues. Being that yeast is a facultative anaerobe, the metabolic state can also influence protein expression, as timing expression of the heterologous protein during fermentation could impact proper function and influence transcriptional/translational stress.

Many improvements have been made in the secretion of recombinant proteins whether targeting the optimization of the fermentation process, metabolic engineering of the host secretion pathway, or protein engineering of the heterologous protein to fit into the native yeast process (Idiris et al., 2010; Martinez et al., 2012). Directed engineering of glycosylation sites in the N-terminal region of heterologous proteins has been shown to improve secretion by preventing exposed hydrophobic residues of the polypeptide from aggregating in the ER (Sagt et al., 2000). Despite all of these advances in improved secretion, there remain technical challenges to restore or maintain cell stress tolerance, especially during high gravity fermentation of fuel ethanol.

It would be highly desirable to be provided with a recombinant yeast strain capable of mitigating the impact of recombinant protein production and secretion on growth rate, especially high temperature growth rate. It would also be highly desirable to be provided with process for making and using such recombinant yeast strains.

BRIEF SUMMARY

The present disclosure relates to an heterologous nucleic acid molecule capable of restoring or increasing the high temperature robustness of recombinant yeast host cells expressing an heterologous protein. The heterologous nucleic acid molecule can include the use of one or more anaerobic-regulated promoter to express the heterologous protein and/or modifications to amino acid sequence and/or glycosylation pattern of the heterologous protein.

In a first aspect, the present disclosure relates to a recombinant yeast host cell comprising an heterologous nucleic acid molecule having a first promoter operatively linked to a first nucleic acid molecule coding for a first heterologous protein. In such recombinant yeast host cell, the first promoter can be selected based on its ability to increase (e.g., being capable of increasing) the expression of the first heterologous protein when the recombinant yeast host cell is in at least partial anaerobic conditions when compared to the level of expression of the first heterologous protein obtained when the recombinant yeast host cell placed in aerobic conditions. Alternatively or complementarily, in the recombinant yeast host cell, the first heterologous protein can comprise at least one amino acid substitution (when compared to a corresponding first native heterologous protein) which restores, maintains or increases the robustness of the recombinant yeast host cell at a high temperature. In an embodiment, the heterologous nucleic acid molecule further comprises a second promoter capable of increasing the expression of the first heterologous protein when the recombinant yeast host cell is in at least partial anaerobic conditions and wherein the second promoter is operatively linked to the first nucleic acid molecule. In such embodiment, the first promoter and/or the second promoter can be selected from the group consisting of tdh1p, pau5p, hor7p, adh1p, tdh2p, tdh3p, gpd1p, cdc19p, eno2p, pdc1p, hxt3p and tpi1p. In still another embodiment, the first heterologous protein, when compared to a corresponding first native heterologous protein, comprises a first amino acid substitution which introduces a (putative) glycosylation site. In some embodiment, the first amino acid substitution can be located in the N-terminal region of the first heterologous protein. In still another embodiment, the first amino acid substitution can introduce an asparagine residue in the first heterologous protein as the (putative) glycosylation site. In yet another embodiment, the first heterologous protein is a lytic enzyme, such as, for example, a saccharolytic enzyme (a glucoamylase or an α-amylase for example). In the embodiment in which the first heterologous protein is a glucoamylase, the corresponding first native protein can have the amino acid sequence of SEQ ID NO: 1. In such embodiment, the first heterologous protein can have the amino acid sequence of SEQ ID NO: 2, SEQ ID NO: 3 or SEQ ID NO: 4. In still another embodiment, the first heterologous protein does not have the amino acid sequence of M6423. In the embodiment in which the first heterologous protein is an α-amylase, the corresponding first native protein can have the amino acid sequence of SEQ ID NO: 6. In such embodiment, the first heterologous protein can have the amino acid sequence of SEQ ID NO: 7. In yet another embodiment, the recombinant yeast host cell (which can be *Saccharomyces cerevisiae*) comprises at least two anaerobic-regulated promoters (pau5p and tdh1p) and encodes for an heterologous protein having the amino acid sequence of SEQ ID NO: 4. In some embodiments, the recombinant yeast host cell can be from the genus *Saccharomyces* (e.g., for example, from the species *Saccharomyces cerevisiae*). In other embodiment, the recombinant yeast host cell can be from the genus *Kluyveromyces, Arxula, Debaryomyces, Candida, Pichia, Phaffia, Schizosaccharomyces, Hansenula, Kloeckera, Schwanniomyces* or *Yarrowia*.

According to a second aspect, the present disclosure provides an isolated glucoamylase having the amino acid sequence of SEQ ID NO: 2, SEQ ID NO: 3 or SEQ ID: 4 or a functional fragment thereof. In an embodiment, the isolated glucoamylase does not have the amino acid sequence of M6423.

According to a third aspect, the present disclosure provides an isolated α-amylase having the amino acid sequence of SEQ ID NO: 7 or a functional fragment thereof.

According to a fourth aspect, the present disclosure provides a recombinant nucleic acid molecule comprising a first promoter as defined herein and a first nucleic acid molecule as defined herein.

According to a fifth aspect, the present disclosure provides a process for hydrolyzing a lignocellulosic biomass. Broadly the process comprises combining the lignocellulosic biomass with (i) a recombinant yeast host cell defined herein or (ii) the isolated glucoamylase defined herein and/or the isolated α-amylase defined herein under conditions so as to allow the cleavage of the substrate by the first heterologous protein expressed by the recombinant yeast host cell, the isolated glucoamylase and/or the isolated α-amylase. In an embodiment, the process further comprises, when the lignocellulosic biomass is combined with the recombinant yeast host cell, (b) culturing the recombinant yeast host cell under conditions so as to allow the generation of a fermentation product by the recombinant yeast host cell. Alternatively, in another embodiment, the process can further comprise, when the lignocellulosic is combined in the absence of the recombinant yeast of cell, combining the substrate with a yeast cell (e.g., a non-genetically modified yeast cell) and (b) culturing the yeast cell under the conditions so as to allow the generation of a fermentation product by the yeast cell. In an embodiment, the fermentation product is ethanol. In yet another embodiment, the lignocellulosic biomass comprises starch (which can be provided, for example, in a gelatinized form or in a raw form). When starch is provided in a gelatinized form, the first heterologous protein and/or the isolated glucoamylase can have the amino acid sequence of SEQ ID NO: 3. When starch is provided in a raw form, the first heterologous protein and/or the glucoamylase can have the amino acid sequence of SEQ ID NO: 4. In an embodiment, the first heterologous protein and/or the α-amylase has the amino acid sequence of SEQ ID NO: 7.

According to a sixth aspect, the present disclosure provides a process for increasing temperature robustness of a first recombinant yeast host cell. Broadly, the process comprises (a) providing a first recombinant yeast host cell and (b) introducing at least one modification to the first heterologous nucleic acid molecule to obtain a second recombinant host cell comprising a second heterologous nucleic acid molecule. The first recombinant yeast host cell of step (a) comprises a first heterologous nucleic acid molecule having a first nucleic acid molecule coding for a first heterologous protein; exhibits reduced growth at a high temperature when compared to a corresponding first yeast host cell lacking the first heterologous nucleic acid molecule; and secretes a higher amount of the first heterologous protein than the corresponding first yeast host cell. In the process, step (b) comprises modifying the first nucleic acid molecule coding for the first heterologous protein to obtain a second nucleic acid molecule coding for a second heterologous protein, wherein the amino acid sequence of the second heterologous protein has at least one amino acid substitution when compared to the amino acid sequence of the first heterologous protein and the at least one amino acid substitution introduces a (putative) glycosylation site in the second modified heterologous protein; and/or operatively linking the first nucleic acid molecule coding for the first heterologous protein or the second nucleic acid molecule coding for the second heterologous protein with a first promoter capable of increasing the expression of the first heterologous protein or the second heterologous protein when the first recombinant yeast host cell is placed in at least partial anaerobic conditions. In an embodiment, the at least one amino acid substitution is located in the N-terminal region of the first or second heterologous protein. In another embodiment, the at least one amino acid residue of the first heterologous protein is replaced by an asparagine residue in the second heterologous protein. In yet another embodiment, the process further comprises modifying the second recombinant yeast host cell by: i) generating a first generation of mutant recombinant yeast host cells by introducing at least one nucleic acid modification in the second heterologous nucleic acid molecule of each of the plurality of mutated recombinant yeast host cells to generate a plurality of mutated heterologous nucleic acid molecules encoding for a corresponding plurality of mutated heterologous proteins; ii) selecting, from the first generation, at least two mutant recombinant yeast host cells wherein each of the two mutant recombinant yeast host cells express mutated heterologous proteins each having at least one different amino acid modification with respect to the second heterologous protein and having the biological activity of the second heterologous protein; iii) generating a third recombinant yeast host cell comprising a third heterologous nucleic acid molecule encoding a third heterologous protein, wherein the third heterologous protein has the at least two of the amino acid modifications encoded by the mutated heterologous nucleic acid molecules of the at least two selected mutant recombinant yeast host cells; and iv) repeating step i) and ii) with the third recombinant yeast host cell to generate a second generation of mutant recombinant yeast host cells, v) selecting from the second generation at least two further mutant recombinant yeast host cells and vi) generating a fourth recombinant yeast host cell comprising a fourth heterologous nucleic acid molecule encoding a fourth heterologous protein, wherein the fourth heterologous nucleic acid molecule comprises the amino acid modifications encoded by the further mutated heterologous nucleic acid molecules of the at least two further selected mutant recombinant yeast host cells.

BRIEF DESCRIPTION OF THE DRAWINGS

Having thus generally described the nature of the invention, reference will now be made to the accompanying drawings, showing by way of illustration, a preferred embodiment thereof, and in which.

TABLE A

Figure 4A:
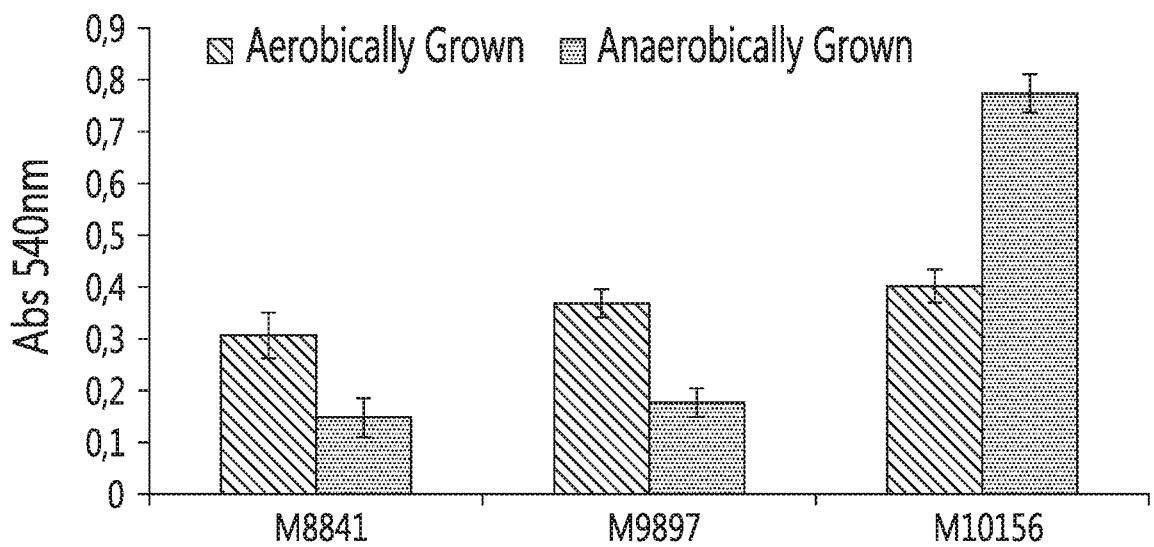
FIGS. 4A and B compare the glucoamylase protein production (A) and growth curves (B), under anaerobic conditions, of different transgenic S. cerevisiae expressing wild-type (SEQ ID NO: 1) or a mutated (SEQ ID NO: 3) S. fibuligera glucoamylase gene under the control of different combinations of promoters. (A) Results are provided as secreted gel starch-degrading activity (as measured by absorbance at 540 nm (Abs540 nm)) of genetically engineered strains either grown aerobically or anaerobically. (B) Results are shown as optical density (measure at 600 nm (OD)) in function of S. cerevisiae strain used (M10156=open circles; M9897=grey circles; M8841=black circles). The amino acid mutations (when using the numbering and the amino acid sequence of the wild-type S. fibuligera glucoamylase gene (SEQ ID NO: 1)) identified in each of the mutants as well as the promoter used of the strains presented in this figure are as follows.

Amino acid mutations and promoters of the strains presented in FIGS. 4.

| Strain | Amino acid mutation in glucoamylase (when compared to SEQ ID NO: 1) | Promoters used |
| --- | --- | --- |
| M8841 | None | tef2p and hxt7p |
| M9897 | A40N | tef2p and hxt7 |
| M10156 | A40N | tdh1p and pau5p |

FIGS. 5A to 5E illustrate the various genetic maps of some of the strains presents in the Examples. (A) Genetic map depicting the fcy1 locus of S. cerevisiae strain M4251 containing a single fcy1 site for integration of single error-prone PCR products. (B) Map depicting the two copy glu011-CO cassette regulated by the TEF2p/ADH3t. (C) Map depicting the two copy glu011-CO cassette regulated by the TDH1p/IDP1t. (D) Map depicting the glu0111-CO cassette, regulated by the TEF2p/ADH3t and HXT7p/PMA1t sequences, integrated at the FCY1 locus found in the M8841 strain. (E) Map depicting the engineered MP743 cassette, regulated by the PAU5p/DIT1t and TDH1p/IDP1t sequences, integrated at the FCY1 locus found in the M10156 stain.

Figure 6:
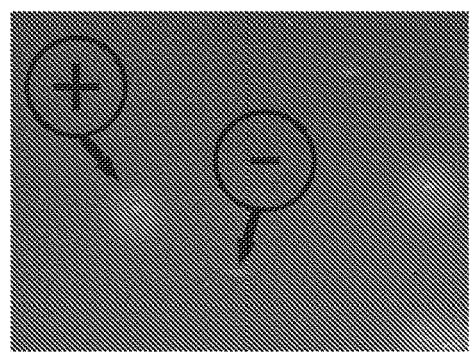

FIG. 6 illustrates a representative picture of the YPD-SFC-starch selection plates stained with iodine vapor to indicate clearing zones around functional mutants (+) and null mutants (−).

Figure 7:
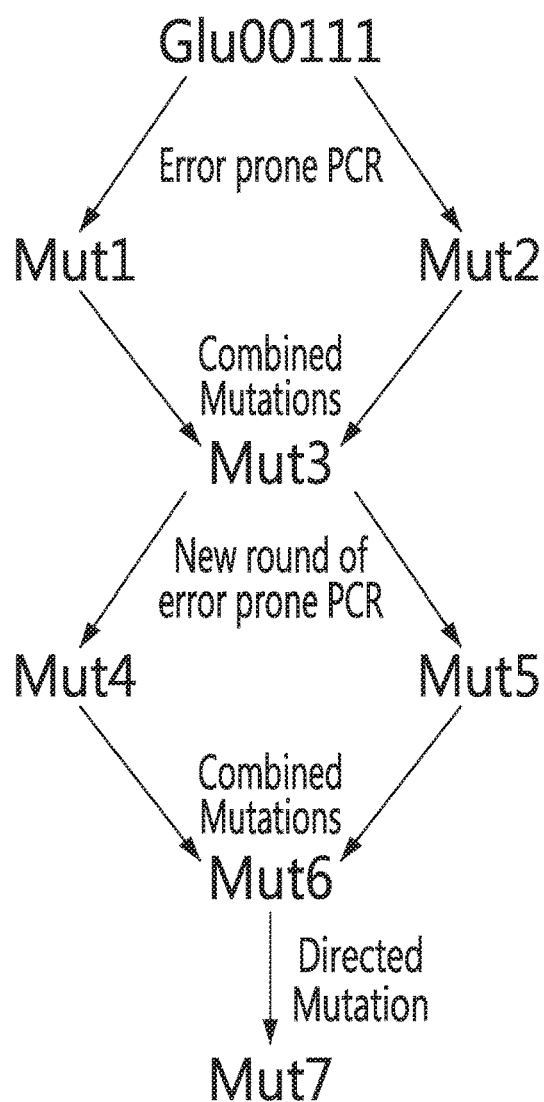

FIG. 7 provides a flow chart depicting the iterative combinatorial mutation process presented in Example II. The amino acid mutations (when using the numbering and the amino acid sequence of the wild-type S. fibuligera glucoamylase gene (SEQ ID NO: 1)) identified in each of the mutants presented in this figure are as follows:

TABLE B

Amino acid mutations of the mutant glucoamylases presented in FIG. 7.

| Mutation | Amino acid substitution |
| --- | --- |
| Mut1 | L8S |
| Mut2 | F101L, K277E |
| Mut3 | L8S, F101L, K277E |
| Mut4 | L8S, F101L, K277E, F487I |
| Mut5 | L8S, F12I, F101L, K277E |
| Mut6 | L8S, F12I, F101L, K277E, F487I |
| Mut7 | L8S, G36N, F12I, F101L, K277E, F487I |

Figure 8:
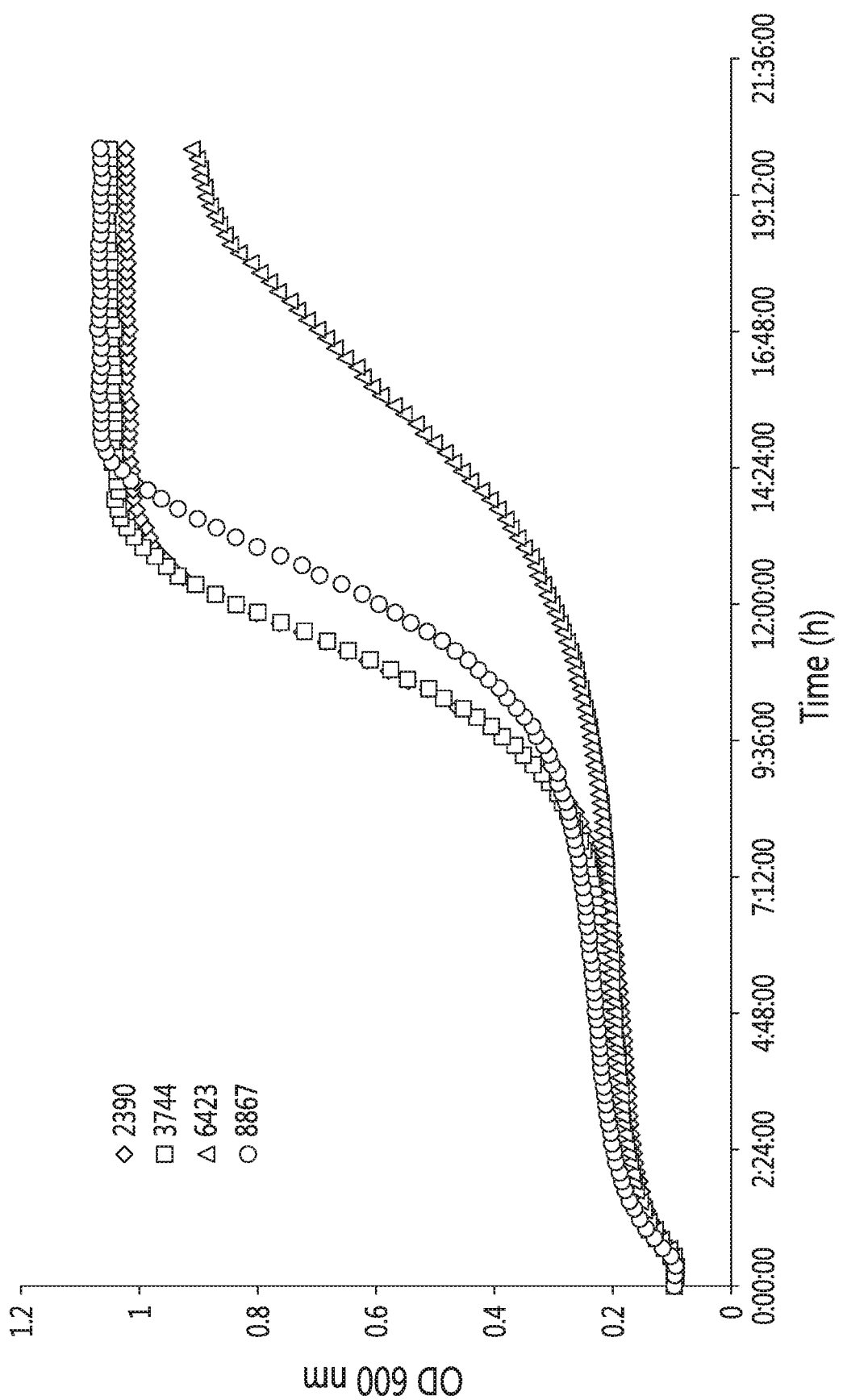

FIG. 8 compares the growth curve (as measured on YPD media at 38° C.) of different strains of S. cerevisiae genetically-engineered to express a glucoamylase gene (M3744 □; M6423 ▲; M8867 ○) with the growth curve of a wild-type S. cerevisiae (M2390 ◊). Growth rates were determined at 38° C. on YPD. Results are shown as the optical density at 600 nm (OD(600 nm)) in function of time of incubation (hours). The amino acid mutations (when using the numbering and the amino acid sequence of the wild-type S. fibuligera glucoamylase gene (SEQ ID NO: 1)) identified in each of the mutants presented in this figure are as follows:

TABLE C

Amino acid mutations of the mutant glucoamylases presented in FIG. 8.

| Strain | Amino acid substitution(s) |
| --- | --- |
| M2390 | Not determined - wild-type S. cerevisiae |
| M3744 | None (SEQ ID NO: 1) |
| M6423 | L8S; F101L; K277E |
| M8867 | L8S; F12I; G36N; F101L; K277E; F487I |

Figure 9A:
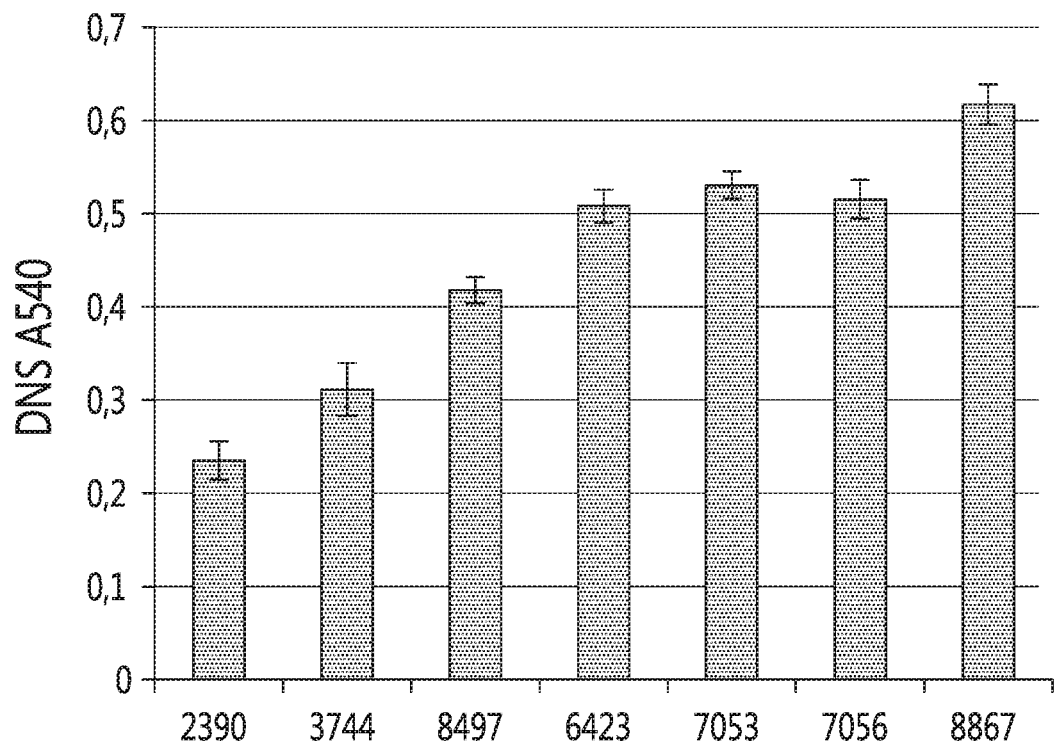

FIGS. 9A and B compare the secreted starch-degrading activity of wild-type or transgenic S. cerevisiae expressing S. fibuligera glucoamylase gene (MP9) or a mutated S. fibuligera glucoamylase gene. Results are shown as the amylase activity (measured as the absorbance at 540 nm (DNSA540) in function of the yeast strains cultured with gelatinized starch (A) or raw starch (B). Two copies of the wild-type of mutant glucoamylase gene are included in each strain. The amino acid mutations (when using the numbering and the amino acid sequence of the wild-type S. fibuligera glucoamylase gene (SEQ ID NO: 1)) identified in each of the mutants presented in this figure are as follows:

TABLE D

Figure 9B:
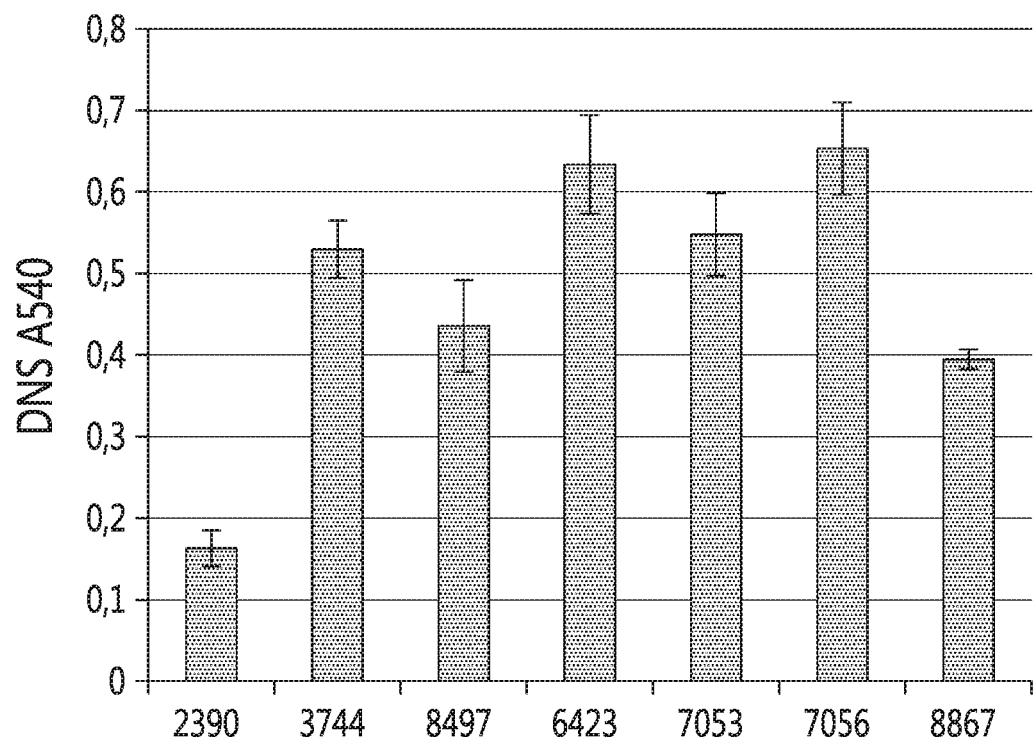

Amino acid mutations of the mutant glucoamylases presented in FIG. 9.

| Strain | Amino acid substitution(s) |
| --- | --- |
| M2390 | Not determined - wild-type S. cerevisiae |
| M3744 | None |
| M8497 | G36N |
| M6423 | L8S; F101L; K277E |
| M7053 | L8S; F101L; K277E; F487I |
| M7056 | L8S; F12I; F101L; K277E |
| M8867 (MP738) | L8S; F12I; G36N; F101L; K277E; F487I |

Figure 10A:
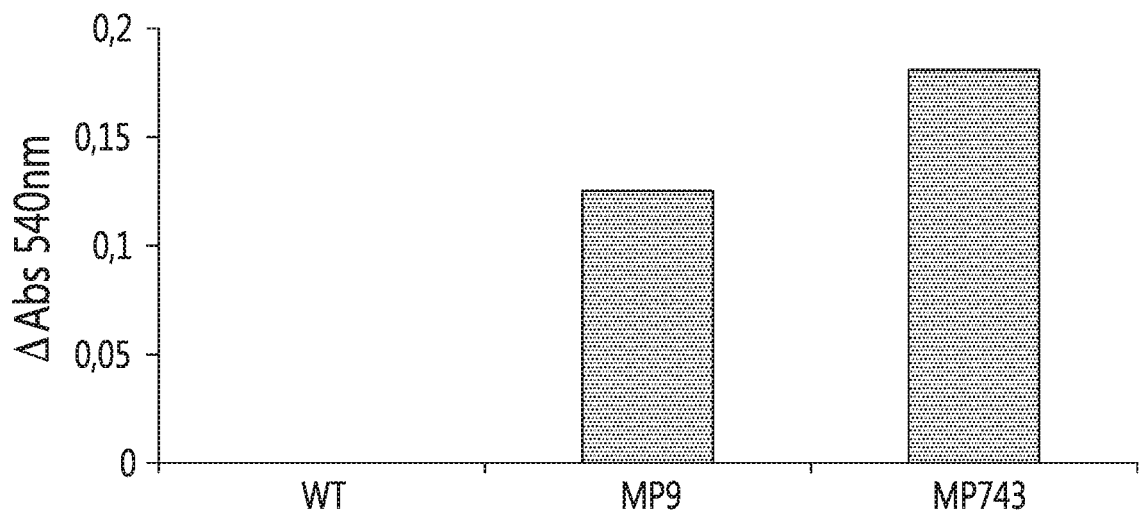
Figure 10B:
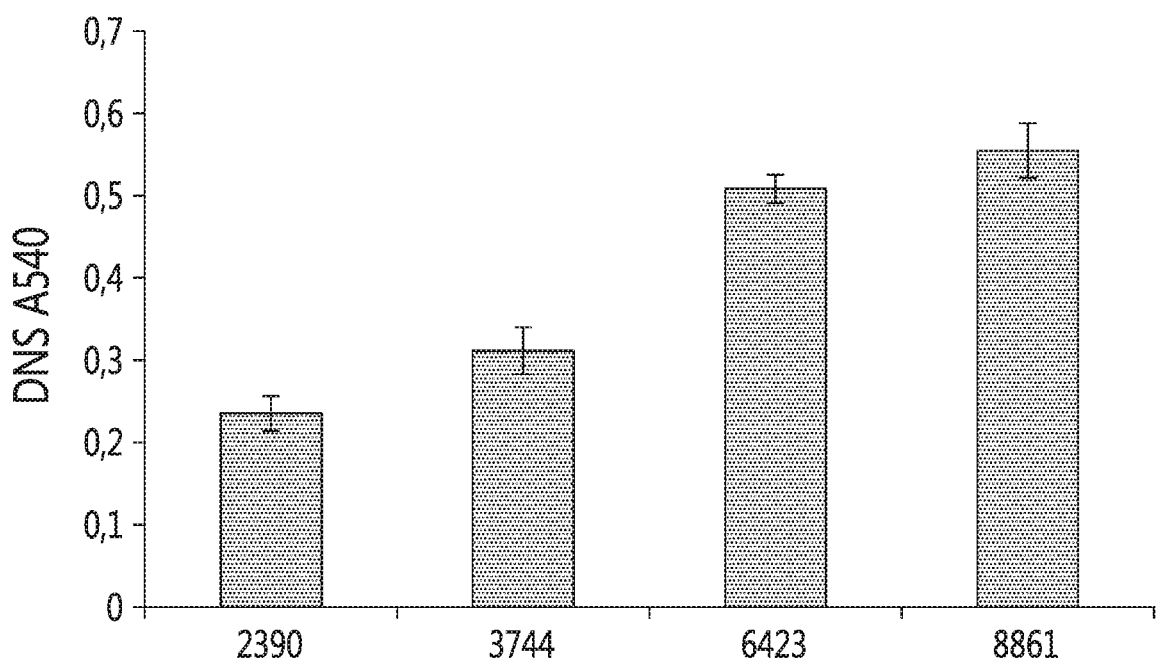
Figure 10C:
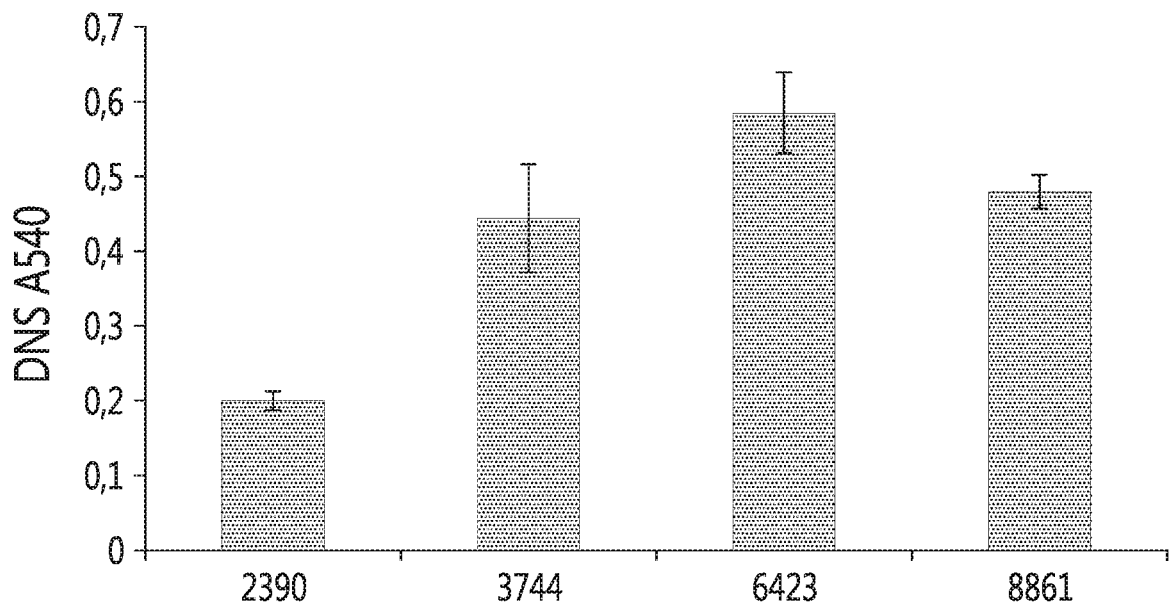

FIGS. 10A to C illustrate results of the secreted starch-degrading activity of wild-type or transgenic S. cerevisiae strains expressing the wild-type S. fibuligera glucoamylase gene (MP9) or a mutated S. fibuligera glucoamylase gene. Results are shown as amylase activity (as measured by optical density at 540 nm) in view of the different strains grown in gelatinized starch (A and B) or raw starch (C). Two copies of the wild-type of mutant glucoamylase gene are included in each strain. The amino acid mutations (when using the numbering and the amino acid sequence of the wild-type S. fibuligera glucoamylase gene (SEQ ID NO: 1)) identified in each of the mutants presented in this figure as follows:

TABLE E

Figure 11A:
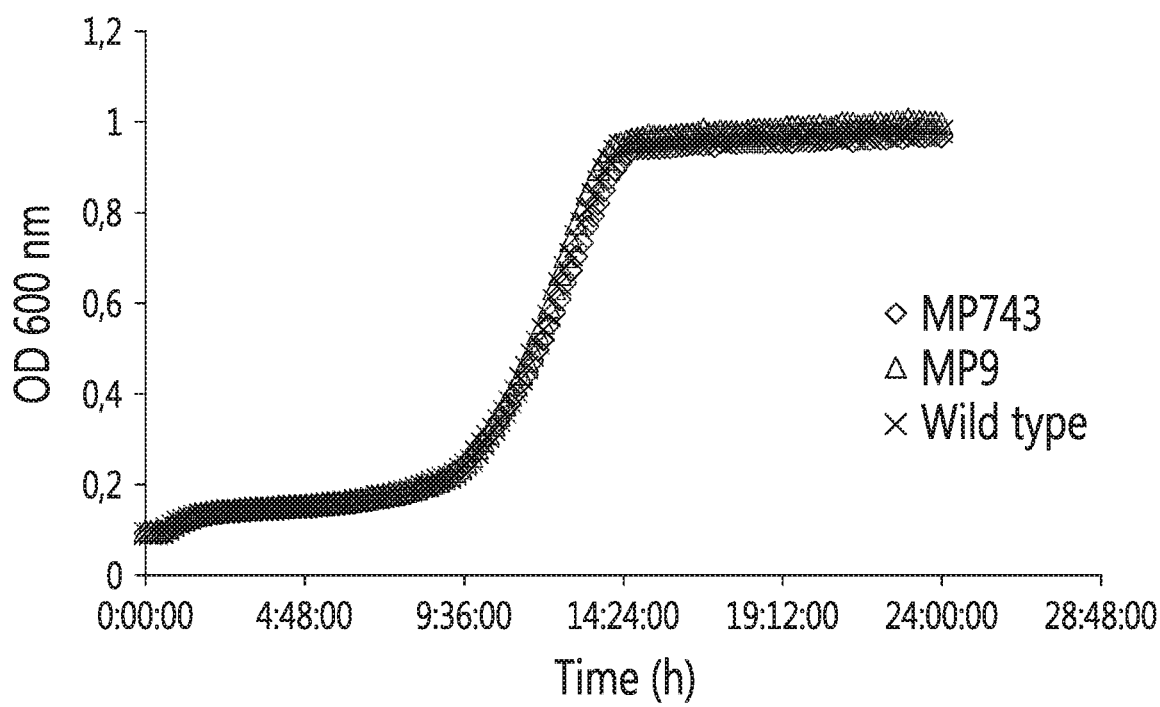
Figure 11B:
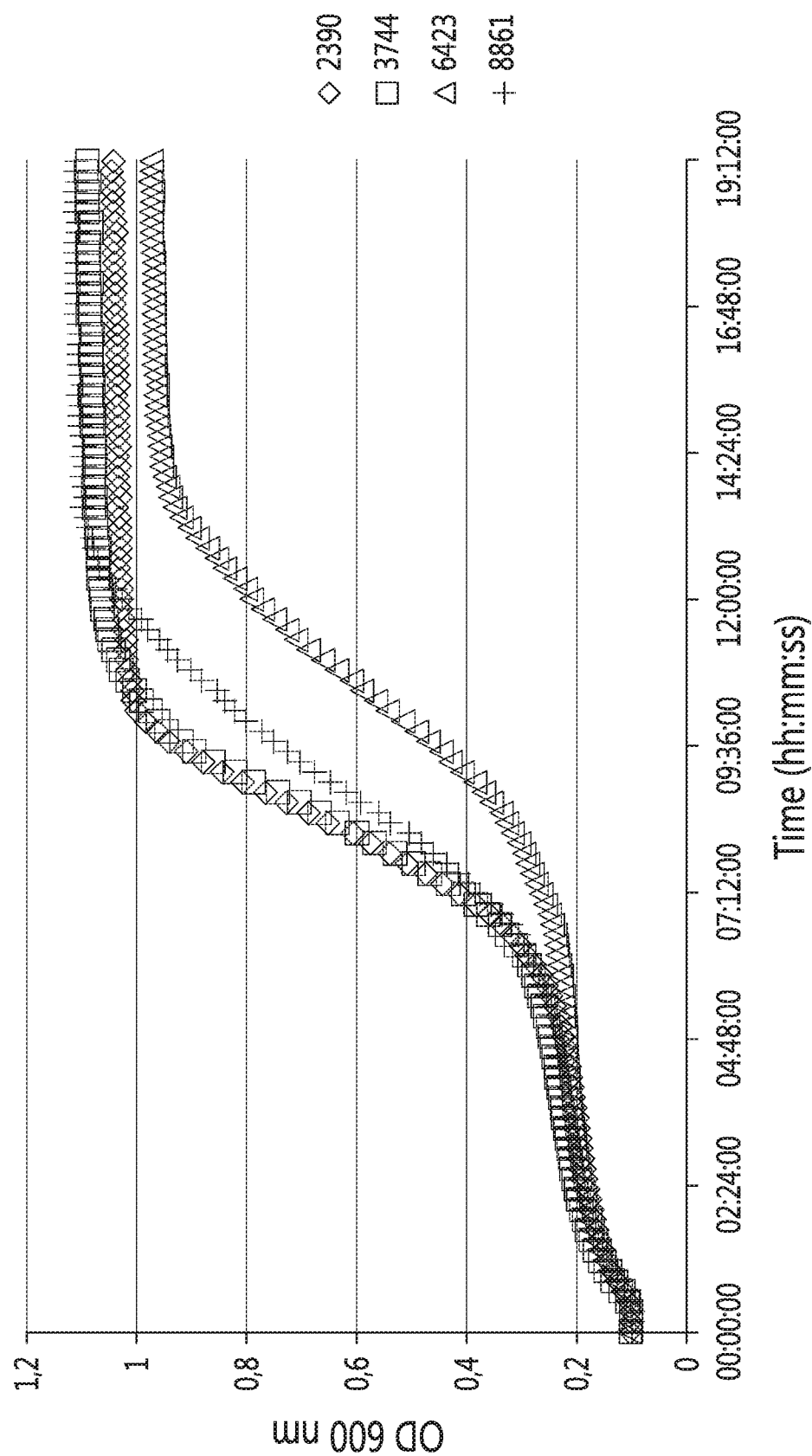

Amino acid mutations of the mutant glucoamylases presented in FIGS. 10 and 11.

| Strain | Amino acid substitution(s) |
| --- | --- |
| M2390 (WT) | Not determined - wild-type S. cerevisiae |
| MP3744 (MP9) | None |
| M6423 | L8S; F101L; K277E |
| MP8498 (MP743) | A40N |
| M8861 (MP732) | L8S; G36N; F101L; K277E |

FIGS. 11A and B compare the growth curve (on YPD media at 38° C.) of different strains of S. cerevisiae genetically-engineered to express S. fibuligera glucoamylase gene with the growth curve of a wild-type S. cerevisiae. Results are shown as the optical density at 600 nm (OD(600 nm)) in function of time of incubation (hours). The different strains used are described in Table E. (A) Results are shown for genetically-engineered MP3744 (Δ) and MP8498 (◊) as well as wild-type (X) strains. (B) Results are shown for genetically-engineered MP3744 (□), MP6423 (A) and MP8861 (+) as well as wild-type (◊) strains. The amino acid mutations (when using the numbering and the amino acid sequence of the wild-type S. fibuligera glucoamylase gene (SEQ ID NO: 1)) identified in each of the mutants presented in this figure are described in Table E.

Figure 12:
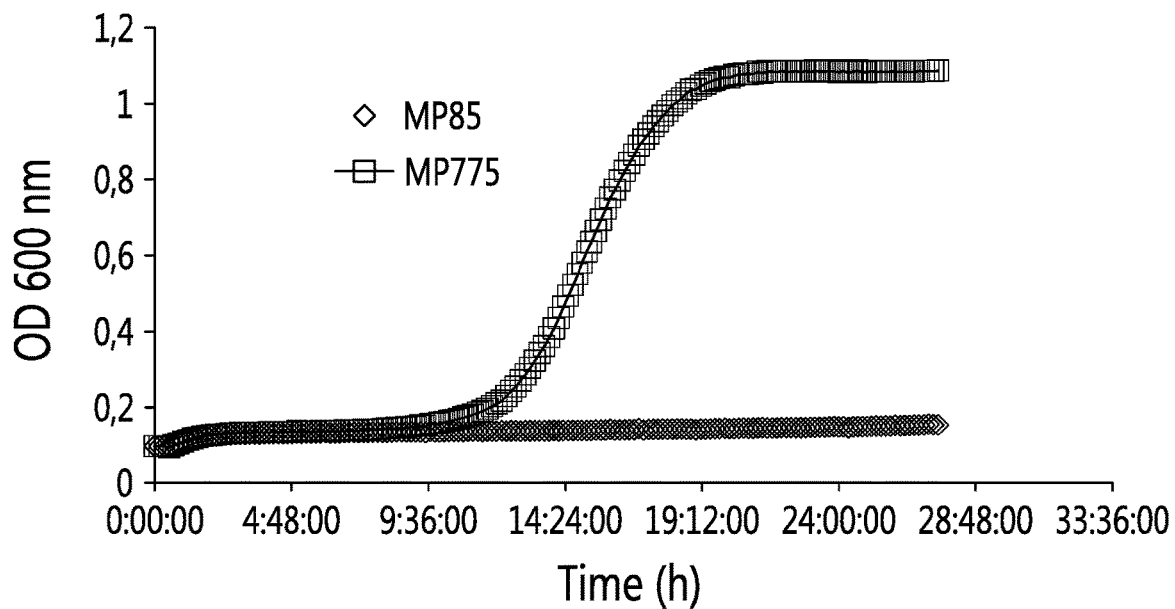

FIG. 12 compares the growth curve of S. cerevisiae wild-type or genetically-engineered to express a wild type B. amyloliquefaciens alpha-amylase gene (MP85 ◊) and a mutated B. amyloliquefaciens alpha-amylase gene (MP775 □). Growth rates were determined at 38° C. on YPD. Results are shown as the optical density at 600 nm (OD(600 nm)) in function of time of incubation (hours). The amino acid mutations (when using the numbering and the amino acid sequence of the wild-type B. amyloliquefaciens alpha-amylase gene (SEQ ID NO: 6)) identified of the mutant presented in this figure are as follows:

TABLE F

Amino acid mutations of the mutant glucoamylases presented in FIG. 12.

| Strain | Amino acid substitution(s) |
| --- | --- |
| M9900 (MP85) | None |
| M10074 (MP775) | K34N |

Figure 13:
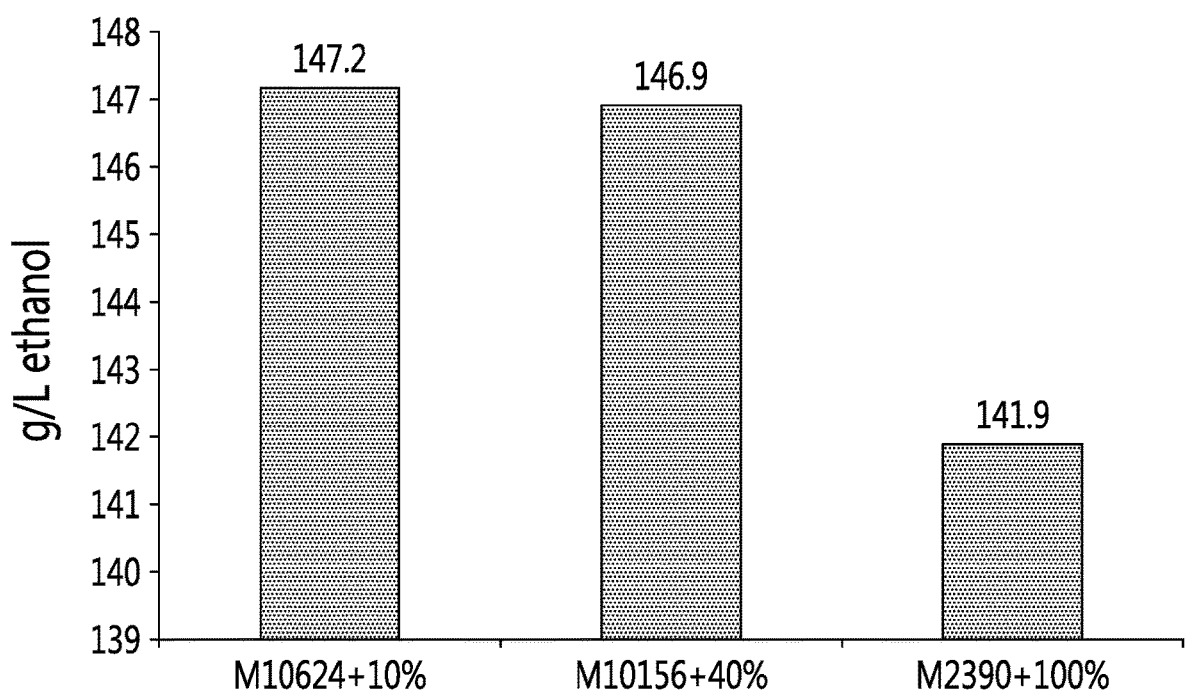

FIG. 13 compares the ethanol production of S. cerevisiae wild-type (M2390), genetically engineered to express a mutated glucoamylase (M10156) or genetically engineered to express a mutated glucoamylase and a mutated alpha-amylase (M10624). The fermentation was conducted in 34% corn flour and 500 ppm of urea at a temperature between 30-32° C. for 88 hours. Results are shown as ethanol yield (g/L) in function of the S. cerevisiae strain used.

TABLE G

Transgenes expressed by the strains presented in FIG. 13.

| Strain | Glucoamylase | Alpha-amylase |
| --- | --- | --- |
| M2390 | None | None |
| M10156 | A40N | None |
| M10624 | A40N | K34N |

DETAILED DESCRIPTION

In accordance with the present disclosure, there are provided nucleic acid molecules which are less susceptible to induce a reduction in the host cell robustness when expressed in such host cell placed at high temperatures. In an embodiment, these nucleic acid molecules, when introduced and expressed into a host cell, do not induce a sensitivity or a loss in robustness in the host cell. The nucleic acid molecules can include a promoter whose activity is promoted during anaerobia (partial or complete). The nucleic acid molecules can comprise a recombinant protein to be expressed by the host cell and which includes one or more mutations (e.g., one of more amino acid substitutions). The present disclosure also provides host cells comprising the nucleic acid molecules, the recombinant proteins encoded by such nucleic acid molecules as well as methods of using same for the production of a product. The present disclosure further comprises a method for making the nucleic acid molecules encoding the heterologous protein as well as the recombinant host cells comprising same.

Recombinant Yeast Strains Exhibiting Robustness

The present disclosure provides recombinant yeast strains (including and expressing an heterologous nucleic acid molecule) and having substantially similar or better robustness when compared to a corresponding yeast strain lacking the heterologous nucleic acid molecule. In the context of the present disclosure, the term "robustness" refers to the recombinant yeast's ability to tolerate or to lack sensibility to perturbations associated with a stress, such as, for example, an increase in incubation/fermentation temperature and/or the expression of a recombinant heterologous protein. In the context of the present disclosure, robustness can be determined by measuring the cellular growth, the cellular growth rate or the cellular growth curve. When exposed to a stressor, the growth of a more robust recombinant yeast strain will be less affected (and in some embodiments not affected) than the growth of a less robust strain. For example, when exposed to a stressor, the cellular growth, the cellular growth rate and/or the cellular growth curve of a more robust strain will less restrained (or, in some embodiments, not restrained) when compared to the cellular growth, the cellular growth rate and/or the cellular growth curve of a less robust strain exposed to the same stressor. As disclosed herein, the robustness of the recombinant yeast cell remains substantially the same in the presence of the heterologous nucleic acid molecule because of the characteristics of the heterologous nucleic acid molecule. More specifically, the heterologous nucleic acid molecule can use a promoter capable of increasing, when compared to a corresponding recombinant yeast host cell in aerobic conditions, the expression of the heterologous protein when the recombinant host cell is in at least partial anaerobia. Alternatively or in combination, the nucleic acid molecule can be designed so as to allow the expression an heterologous protein which comprises at least one amino acid mutation (e.g., substitution), when compared to a corresponding native heterologous protein, which maintains the robustness of the recombinant yeast host cell at high temperatures.

In the context of the present disclosure, "high temperatures" or "a high temperature" refers to a temperature above the recombinant yeast's optimal growth temperature. In the embodiment in which the yeast used as a host cell is from the *Saccharomyces* genus (which has an optimal temperature between 30° C. and 35° C.), a high temperature can be above 35° C. (for example between 35° C. and 40° C.) and, in some embodiments, the high temperature is about 38° C. In the embodiment in which the yeast used as a host cell is from the *Kluyveromyces* genus (which has an optimal temperature between 35° C. and 40° C.), a high temperature can be above 40° C. (for example between 40° C. and 45° C.) and, in some embodiments, the high temperature is at about 42° C. In the embodiment in which the yeast used as a host cell is from the *Candida* genus (which has an optimal temperature between 30° C. and 35° C.), a high temperature can be above 35° C. (for example between 35° C. and 40° C.) and, in some embodiments, the high temperature is at about 38° C. In the embodiment in which the yeast used as a host cells is from the *Pichia* genus (which has an optimal temperature between 25° C. and 35° C.), a high temperature can be above 35° C. (for example between 35° C. and 40° C.) and, in some embodiments, the high temperature is at about 38° C. In the embodiment in which the yeast used as a host cell is from the *Schizosaccharomyces* genus (which has an optimal temperature between 25° C. and 35° C.), a high temperature can be above 35° C. (for example between 35° C. and 40° C.) and, in some embodiments, the high temperature is at about 38° C. In the embodiment in which the yeast used as a host cell is from the *Hansenula* genus (which has an optimal temperature between 45° C. and 50° C.), a high temperature can be above 50° C. (for example between 50° C. and 55° C.) and, in some embodiments, the high temperature is at about 53° C. In the embodiment in which the yeast used as a host cell is from the *Schizosaccharomyces* genus (which has an optimal temperature between 25° C. and 35° C.), a high temperature can be above 35° C. (for example between 35° C. and 40° C.) and, in some embodiments, the high temperature is at about 38° C. In the embodiment in which the yeast used as a host cell is from the *Hansenula* genus (which has an optimal temperature between 45° C. and 50° C.), a high temperature can be above 50° C. (for example between 50° C. and 55° C.) and, in some embodiments, the high temperature is at about 53° C. In the embodiment in which the yeast used as a host cell is from the *Kloeckera* genus (which has an optimal temperature between 30° C. and 35° C.), a high temperature can be above 35° C. (for example between 35° C. and 40° C.) and, in some embodiments, the high temperature is at about 38° C. In the embodiment in which the yeast used as a host cell is from the *Schwanniomyces* genus (which has an optimal temperature between 35° C. and 40° C.), a high temperature can be above 40° C. (for example between 40° C. and 45° C.) and, in some embodiments, the high temperature is at about 43° C. In the embodiment in which the yeast used as a host cell is from the *Yarrowia* genus (which has an optimal temperature between 30° C. and 35° C.), a high temperature can be above 35° C. (for example between 35° C. and 40° C.) and, in some embodiments, the high temperature is at about 38° C.

Due to its recombinant nature, the recombinant yeast strains having robustness comprise a "heterologous" nucleic acid molecule for expressing a "heterologous" protein. The term "heterologous" when used in reference to a nucleic acid molecule (such as a promoter or a coding sequence) or a polypeptide (such as an enzyme) refers to a nucleic acid molecule or a protein is not natively found in the host organism or cell. "Heterologous" also includes a native coding region, or portion thereof, that is removed from the source organism and subsequently reintroduced into the source organism in a form that is different from the corresponding native gene, e.g., not in its natural location in the organism's genome. The heterologous nucleic acid molecule is purposively introduced into the host cell. A "heterologous" nucleic acid molecule or protein may be derived from any source, e.g., eukaryotes, prokaryotes, viruses, etc. In an embodiment, the heterologous nucleic acid molecule may be derived from an eukaryote (such as, for example, another yeast) or a prokaryote (such as, for example, a bacteria). The term "heterologous" as used herein also refers to an element (nucleic acid or protein) that is derived from a source other than the endogenous source. Thus, for example, a heterologous element could be derived from a different strain of host cell, or from an organism of a different taxonomic group (e.g., different kingdom, phylum, class, order, family genus, or species, or any subgroup within one of these classifications). The term "heterologous" is also used synonymously herein with the term "exogenous".

In the context of the present disclosure, the heterologous nucleic acid molecule can be integrated in the genome of the yeast host cell. The term "integrated" as used herein refers to genetic elements that are placed, through molecular biology techniques, into the genome of a host cell. For example, genetic elements can be placed into the chromosomes of the host cell as opposed to in a vector such as a plasmid carried by the host cell. Methods for integrating genetic elements into the genome of a host cell are well known in the art and include homologous recombination. The heterologous nucleic acid molecule can be present in one or more copies in the yeast host cell's genome.

Alternatively, the heterologous nucleic acid molecule can be independently replicating from the yeast's genome. In such embodiment, the nucleic acid molecule can be stable and self-replicating.

The heterologous nucleic acid molecule can be introduced in the yeast host cell using a vector. A "vector," e.g., a "plasmid", "cosmid" or "YAC" (yeast artificial chromosome) refers to an extra chromosomal element and is usually in the form of a circular double-stranded DNA molecule. Such vectors may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

In the heterologous nucleic acid molecule, the promoter and the nucleic acid molecule coding for the heterologous protein are operatively linked to one another. In the context of the present disclosure, the expressions "operatively linked" or "operatively associated" refers to fact that the promoter is physically associated to the nucleotide acid molecule coding for the heterologous protein in a manner that allows, under certain conditions, for expression of the heterologous protein from the nucleic acid molecule. In an embodiment, the promoter can be located upstream (5') of the nucleic acid sequence coding for the heterologous protein. In still another embodiment, the promoter can be located downstream (3') of the nucleic acid sequence coding for the heterologous protein. In the context of the present disclosure, one or more than one promoter can be included in the heterologous nucleic acid molecule. When more than one promoter is included in the heterologous nucleic acid molecule, each of the promoters is operatively linked to the nucleic acid sequence coding for the heterologous protein. The promoters can be located, in view of the nucleic acid molecule coding for the heterologous protein, upstream, downstream as well as both upstream and downstream.

"Promoter" refers to a DNA fragment capable of controlling the expression of a coding sequence (such as a nucleic acid molecule coding for an heterologous protein) or functional RNA. The term "expression," as used herein, refers to the transcription and stable accumulation of sense (mRNA) from the heterologous nucleic acid molecule described herein. Expression may also refer to translation of mRNA into a polypeptide. Promoters may be derived in their entirety from a native gene, or be composed of different elements derived from different promoters found in nature, or even comprise synthetic DNA segments. It is understood by those skilled in the art that different promoters may direct the expression at different stages of development, or in response to different environmental or physiological conditions. Promoters which cause a gene to be expressed in most cells at most times at a substantially similar level are commonly referred to as "constitutive promoters". It is further recognized that since in most cases the exact boundaries of regulatory sequences have not been completely defined, DNA fragments of different lengths may have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease S1), as well as protein binding domains (consensus sequences) responsible for the binding of the polymerase.

The promoter that can be included in the heterologous nucleic acid molecule allows or favors the expression of the heterologous protein in partial or total anaerobic conditions (e.g., anaerobic-regulated promoter). Therefore, the promoter used favors the expression of the heterologous protein in an environment in which the oxygen level is reduced (e.g., anaerobic conditions) when compared to the oxygen level in ambient air (e.g., aerobic conditions in which oxygen is usually present at about 21% volume in ambient air). The promoter can allow for the expression of the heterologous protein when the recombinant yeast host cell is placed in aerobic conditions, however, under the control of the promoter, the level of expression of the heterologous protein is lower in recombinant yeast host cells placed in aerobic conditions when compared to the level of expression of the same recombinant yeast host cell placed in (partial or total) anaerobic conditions. As such, the promoter allows for the preferential expression of the heterologous protein when the recombinant yeast host cell is placed in conditions of at least partial anaerobia. As used in the context of the present disclosure, the term "anaerobic conditions" refers to conditions in which the oxygen level (by volume) is lower than 21% (for example lower than or equal to about 20, 19, 18, 17, 16, 15, 14, 13, 12, 11, 10, 9, 8, 7, 6, 5, 4, 3, 2, 1 or 0%).

The heterologous nucleic acid molecule can comprise more than one promoter. In such instance, each of the promoters is covalently linked to the nucleic acid molecule encoding the heterologous and is an anaerobic-regulated promoter. The promoter that can be operatively linked to the nucleic acid molecule encoding for the heterologous protein can include, but is not limited to the promoter of the tdh1 gene (tdh1p, see, for example the nucleic acid sequence of SEQ ID NO: 9), the promoter of the pau5 gene (pau5p, see, for example, the nucleic acid sequence of SEQ ID NO: 10), the promoter of the anb1 gene (anb1p, see, for example, the nucleic acid sequence of SEQ ID NO: 11), the promoter of the hor7 gene (hor7p, see, for example, the nucleic acid sequence of SEQ ID NO: 12), the promoter of the adh1 gene (adh1p, see, for example, the nucleic acid sequence of SEQ ID NO: 13), the promoter of the tdh2 gene (tdh2p, see, for example, the nucleic acid sequence of SEQ ID NO: 14), the promoter of the tdh3 gene (tdh3p, see, for example, the nucleic acid sequence of SEQ ID NO: 15), the promoter of the gpd1 gene (gpd1p, see, for example, the nucleic acid sequence of SEQ ID NO: 16), the promoter of the cdc19 gene (cdc19p, see, for example, the nucleic acid sequence of SEQ ID NO: 17), the promoter of the eno2 gene (eno2p, see, for example, the nucleic acid sequence of SEQ ID NO: 18), the promoter of the pdc1 gene (pdc1p, see, for example, the nucleic acid sequence of SEQ ID NO: 19), the promoter of the hxt3 gene (hxt3p, see, for example, the nucleic acid sequence of SEQ ID NO: 20), the promoter of the tpi1 gene (tpi1p, see for example, the nucleic acid sequence of SEQ ID NO: 21), the anaerobic-regulated promoter of the genes listed in Kwast et al., 2002, ter Lind et al., 1999 and Tai et al., 2002. The combination of promoters that can be included in the heterologous nucleic acid molecule can include, but is not limited to, the combination of any two or more promoters of the tdh1 gene (tdh1p), the promoter of the pau5 gene (pau5p), the promoter of the anb1 gene (anb1p), the promoter of the hor7 gene (hor7p), the promoter of the adh1 gene (adh1p), the promoter of the tdh2 gene (tdh2p), the promoter of the tdh3 gene (tdh3p), the promoter of the gpd1 gene (gpd1p), the promoter of the cdc19 gene (cdc19p), the promoter of the eno2 gene (eno2p), the promoter of the pdc1 gene (pdc1p), the promoter of the hxt3 gene (hxt3p), the promoter of the tpi1 gene (tpi1p), the anaerobic-regulated promoter of the genes listed in Kwast et al., 2002, ter Lind et al., 1999 and Tai et al., 2002. In an embodiment, the combination of promoters that are included in the heterologous nucleic acid molecule comprises or consists of the promoter of the tdh1 gene (tdh1p) and the promoter of the pau5 gene (pau5p).

The promoter can be heterologous to the nucleic acid molecule encoding the heterologous protein. The promoter can be heterologous or derived from a strain being from the same genus or species as the recombinant yeast host cell. In an embodiment, the promoter is derived from the same genus or species of the yeast host cell and the heterologous protein is derived from different genus that the yeast host cell.

The recombinant yeast host cell can be used for the production of various heterologous proteins. In an embodiment, the recombinant yeast host cell can be used for the production of an enzyme, and especially an enzyme involved in the cleavage or hydrolysis of its substrate (e.g., a lytic enzyme and, in some embodiments, a saccharolytic enzyme). In still another embodiment, the enzyme can be a glycoside hydrolase. In the context of the present disclosure, the term "glycoside hydrolase" refers to an enzyme involved in carbohydrate digestion, metabolism and/or hydrolysis, including amylases, cellulases, hemicellulases, cellulolytic and amylolytic accessory enzymes, inulinases, levanases, trehalases, pectinases, and pentose sugar utilizing enzymes. In another embodiment, the enzyme can be a protease. In the context of the present disclosure, the term "protease" refers to an enzyme involved in protein digestion, metabolism and/or hydrolysis. In yet another embodiment, the enzyme can be an esterase. In the context of the present disclosure, the term "esterase" refers to an enzyme involved in the hydrolysis of an ester from an acid or an alcohol, including phosphatases such as phytases.

The heterologous protein can be an "amylolytic enzyme", an enzyme involved in amylase digestion, metabolism and/or hydrolysis. The term "amylase" refers to an enzyme that breaks starch down into sugar. All amylases are glycoside hydrolases and act on α-1,4-glycosidic bonds. Some amylases, such as γ-amylase (glucoamylase), also act on α-1,6-glycosidic bonds. Amylase enzymes include α-amylase (EC 3.2.1.1), β-amylase (EC 3.2.1.2), and γ-amylase (EC 3.2.1.3). The α-amylases are calcium metalloenzymes, unable to function in the absence of calcium. By acting at random locations along the starch chain, α-amylase breaks down long-chain carbohydrates, ultimately yielding maltotriose and maltose from amylose, or maltose, glucose and "limit dextrin" from amylopectin. Because it can act anywhere on the substrate, α-amylase tends to be faster-acting than β-amylase. In an embodiment, the heterologous protein is derived from a α-amylase such as, for example, from the α-amylase of *Bacillus amyloliquefacens*. Another form of amylase, β-amylase is also synthesized by bacteria, fungi, and plants. Working from the non-reducing end, β-amylase catalyzes the hydrolysis of the second α-1,4 glycosidic bond, cleaving off two glucose units (maltose) at a time. Many microbes produce amylase to degrade extracellular starches. In addition to cleaving the last α(1-4) glycosidic linkages at the nonreducing end of amylose and amylopectin, yielding glucose, γ-amylase will cleave α(1-6) glycosidic linkages. In an embodiment, the heterologous protein is derived from a γ-amylase, such as, for example, the glucoamylase of *Saccharomycoces filbuligera* (e.g., encoded by the glu 0111 gene). Another amylolytic enzyme is α-glucosidase that acts on maltose and other short malto-oligosaccharides produced by α-, β-, and γ-amylases, converting them to glucose. Another amylolytic enzyme is pullulanase. Pullulanase is a specific kind of glucanase, an amylolytic exoenzyme, that degrades pullulan. Pullulan is regarded as a chain of maltotriose units linked by alpha-1, 6-glycosidic bonds. Pullulanase (EC 3.2.1.41) is also known as pullulan-6-glucanohydrolase (debranching enzyme). Another amylolytic enzyme, isopullulanase, hydrolyses pullulan to isopanose (6-alpha-maltosylglucose). Isopullulanase (EC 3.2.1.57) is also known as pullulan 4-glucanohydrolase. An "amylase" can be any enzyme involved in amylase digestion, metabolism and/or hydrolysis, including α-amylase, β-amylase, glucoamylase, pullulanase, isopullulanase, and alpha-glucosidase.

The heterologous protein can be a "cellulolytic enzyme", an enzyme involved in cellulose digestion, metabolism and/or hydrolysis. The term "cellulase" refers to a class of enzymes that catalyze cellulolysis (i.e. the hydrolysis) of cellulose. Several different kinds of cellulases are known, which differ structurally and mechanistically. There are general types of cellulases based on the type of reaction catalyzed: endocellulase breaks internal bonds to disrupt the crystalline structure of cellulose and expose individual cellulose polysaccharide chains; exocellulase cleaves 2-4 units from the ends of the exposed chains produced by endocellulase, resulting in the tetrasaccharides or disaccharide such as cellobiose. There are two main types of exocellulases (or cellobiohydrolases, abbreviate CBH)—one type working processively from the reducing end, and one type working processively from the non-reducing end of cellulose; cellobiase or beta-glucosidase hydrolyses the exocellulase product into individual monosaccharides; oxidative cellulases that depolymerize cellulose by radical reactions, as for instance cellobiose dehydrogenase (acceptor); cellulose phosphorylases that depolymerize cellulose using phosphates instead of water. In the most familiar case of cellulase activity, the enzyme complex breaks down cellulose to beta-glucose. A "cellulase" can be any enzyme involved in cellulose digestion, metabolism and/or hydrolysis, including an endoglucanase, glucosidase, cellobiohydrolase, xylanase, glucanase, xylosidase, xylan esterase, arabinofuranosidase, galactosidase, cellobiose phosphorylase, cellodextrin phosphorylase, mannanase, mannosidase, xyloglucanase, endoxylanase, glucuronidase, acetylxylanesterase, arabinofuranohydrolase, swollenin, glucuronyl esterase, expansin, pectinase, and feruoyl esterase protein.

The heterologous protein can have "hemicellulolytic activity", an enzyme involved in hemicellulose digestion, metabolism and/or hydrolysis. The term "hemicellulase" refers to a class of enzymes that catalyze the hydrolysis of cellulose. Several different kinds of enzymes are known to have hemicellulolytic activity including, but not limited to, xylanases and mannanases.

The heterologous protein can have "xylanolytic activity", an enzyme having the is ability to hydrolyze glycosidic linkages in oligopentoses and polypentoses. The term "xylanase" is the name given to a class of enzymes which degrade the linear polysaccharide beta-1,4-xylan into xylose, thus breaking down hemicellulose, one of the major components of plant cell walls. Xylanases include those enzymes that correspond to Enzyme Commission Number 3.2.1.8. The heterologous protein can also be a "xylose metabolizing enzyme", an enzyme involved in xylose digestion, metabolism and/or hydrolysis, including a xylose isomerase, xylulokinase, xylose reductase, xylose dehydrogenase, xylitol dehydrogenase, xylonate dehydratase, xylose transketolase, and a xylose transaldolase protein. A "pentose sugar utilizing enzyme" can be any enzyme involved in pentose sugar digestion, metabolism and/or hydrolysis, including xylanase, arabinase, arabinoxylanase, arabinosidase, arabinofuranosidase, arabinoxylanase, arabinosidase, and arabinofuranosidase, arabinose isomerase, ribulose-5-phosphate 4-epimerase, xylose isomerase, xylulokinase, xylose reductase, xylose dehydrogenase, xylitol dehydrogenase, xylonate dehydratase, xylose transketolase, and/or xylose transaldolase.

The heterologous protein can have "mannanic activity", an enzyme having the is ability to hydrolyze the terminal, non-reducing β-D-mannose residues in β-D-mannosides. Mannanases are capable of breaking down hemicellulose, one of the major components of plant cell walls. Xylanases include those enzymes that correspond to Enzyme Commission Number 3.2.2.25.

The heterologous protein can be a "pectinase", an enzyme, such as pectolyase, pectozyme and polygalacturonase, commonly referred to in brewing as pectic enzymes. These enzymes break down pectin, a polysaccharide substrate that is found in the cell walls of plants.

The heterologous protein can have "treholytic activity, an enzyme catalyzing the conversion of threhalose to glucose. Trehalase (EC 3.2.1.28) can be classified based on their optimal pH as neutral (optimal pH of about 7.0) or acid trehalase (optimal pH of about 4.5).

The heterologous protein can have "phytolytic activity", an enzyme catalyzing the conversion of phytic acid into inorganic phosphorus. Phytases (EC 3.2.3) can be belong to the histidine acid phosphatases, β-propeller phytases, purple acid phosphatases or protein tyrosine phosphatase-like phytases family.

The heterologous protein can have "proteolytic activity", an enzyme involved in protein digestion, metabolism and/or hydrolysis, including serine proteases, threonine proteases, cysteine proteases, aspartate proteases, glutamic acid proteases and metalloproteases.

As indicated above, the heterologous protein is purposefully modified from its native amino acid sequence to introduce at least one amino acid substitution (when compared to the native protein) and such amino acid substitution maintains or increases the robustness of the yeast strain expressing the modified heterologous protein (when compared to the robustness of a corresponding yeast strain expressing the native non-modified protein).

In an embodiment, the heterologous protein is modified to introduce an additional (putative) glycosylation site to maintain or increase its robustness at high temperatures. In some embodiments, the heterologous protein is modified to substitute an amino acid which is not glycosylated which an amino acid which can be glycosylated. The term "glycosylation" refers to the chemical reaction in which a carbohydrate is attached to a functional group of an amino acid (in some embodiments, located on the side chain of the amino acid). One example of an amino acid which can be glycosylated is an amino acid having an amide functional group (such as, for example asparagine). In certain embodiments, asparagine can be glycosylated by the attachment of a glycan to the available nitrogen atom of the amide functional group (located either in the amino acid residue's side chain or amino group). In such embodiment, the glycosylation is referred to as an N-glycosylation and the glycosylated amino acid as an N-glycosylated amino acid. Another example of an amino acid residue which can be glycosylated is an amino acid having a hydroxyl oxygen in its side chain (such as, for example, serine, threonine, tyrosine, hydroxylysine or hydroxyproline). In such embodiment, the glycosylation is referred to as an O-glycosylation and the glycosylated amino acid residue as an O-glycosylated amino acid. A further example of an amino acid residue which can be glycosylated is an amino acid residue having an aromatic side chain and the glycosylated atom is a carbon atom (such as, for example, tryptophan). In such embodiment, the glycosylation (mannosylation for example) is referred to as a C-glycosylation and the glycosylated amino acid residue as a C-glycosylated amino acid residue. In the context of the present disclosure one or more substitution can be made to the native protein to include one or more glycosylation sites on the heterologous protein.

The additional glycosylation site can be located anywhere in the heterologous protein provided that the introduction of the glycosylation site does not substantially alter the biological activity (in some embodiments the enzymatic activity) of the heterologous protein and that it located at a position so as to protect hydrophobic regions of the heterologous protein during synthesis or folding. Identification of glycosylation sites. In some embodiments, potential N-linked glycosylation sites can be identified by amino acid sequence analysis coupled with homology modelling of the target protein. Disordered regions of the protein are identified by homology modelling and/or secondary structure prediction, and a disordered region of interest is identified. These regions can be located in the N- or C-terminal regions of the protein, or other intermediate regions. The amino acid sequence of the region is analyzed for potential point mutations introducing an asparagine, serine, or threonine which results in the N-linked glycosylation motif NX[S/T], where X is any amino acid except proline. In addition to point mutations, an insertion of the consensus sequence NX[S/T], where X is any amino acid except proline, can also be used to maintain flanking amino acid sequences while still introducing a glycosylation site motif.

In some embodiments, the putative glycosylation site is introduced in the N-terminal region of the heterologous protein. This embodiment is particularly advantageous when the heterologous protein is an amylase. In the context of the present disclosure, the term "N-terminal region" refers to the portion of the heterologous protein which is located in the vicinity of the N-terminus of the heterologous protein. In some embodiments, the N-terminal region spans from the first (when starting from the first encoded amino acid residue of the heterologous protein) to the $100^{th}$, $90^{th}$, $80^{th}$, $70^{th}$, $60^{th}$, $50^{th}$ or $40^{th}$ upstream amino acid residues of the heterologous protein. In the context of the present disclosure, the N-terminal region includes the signal peptide of a heterologous protein. In alternative or complementary embodiments, the putative glycosylation site is introduced in the C-terminal region of the heterologous protein. In the context of the present disclosure, the term "C-terminal region" refers to the portion of the heterologous protein which is located in the vicinity of the C-terminus of the heterologous protein. In some embodiments, the C-terminal region spans from the last (when started from the last encoded amino acid residue of the heterologous protein) to the last $100^{th}$, $90^{th}$, $80^{th}$, $70^{th}$, $60^{th}$, $50^{th}$ or $40^{th}$ amino acid residues of the heterologous protein.

In the embodiments in which the heterologous protein exhibits amylase activity (such as, for example, when the heterologous is a glucoamylase of SEQ ID NO: 1), substitutions with an asparagine, serine or threonine residues which would result in an N-linked glycosylation site motif NX[S/T] can be added. In such embodiment, the N-terminal region was limited to amino acids preceding the first natively occurring N-linked glycosylation motif (e.g. for example, when the heterologous protein is a glucoamylase (glu 0111), the first natively occurring N-linked glycosylation motif is N43 in SEQ ID NO: 1), or the beginning of the first alpha-helix (e.g., for example, when the heterologous protein is a glucoamylase (glu 0111), the beginning of the first alpha helix is F44 of SEQ ID NO: 1) determined by homology modelling/secondary structure predictions. In one example, the additional glycosylation site can be added by substituting an amino acid residue corresponding to position 36 and/or 40 of SEQ ID NO: 1 with an asparagine, serine and/or threonine residue. In still another example, the heterologous protein has an arginine residue corresponding to position 36 and/or 40 of SEQ ID NO: 1 or 2. In yet a further embodiment, the heterologous protein has the amino acid sequence of SEQ ID NO: 3 or 4. In a further embodiment, the heterologous protein does not have the amino acid sequence of the 6423 mutant (e.g., comprising the amino acid substitutions L8S; F101L; K277E when compared to the amino acid sequence of SEQ ID NO: 1).

In the embodiments in which the heterologous protein is an α-amylase (such as, for example, in the embodiment in which the native protein is the α-amylase of *Bacillus amyloliquefaciens*), the additional glycosylation site can be added by substituting an amino acid residue corresponding to positions 26, 27, 34, 35, 36 and/or 37 of SEQ ID NO: 6 with an arginine, serine and/or threonine residue. In still another example, the heterologous protein has an arginine residue corresponding to positions 26, 34, 36 and/or 37 of SEQ ID NO: 6. In yet another embodiment, the heterologous protein has a serine residue corresponding to positions 27 and/or 35 of SEQ ID NO: 6. In yet a further embodiment, the heterologous protein has the amino acid sequence of SEQ ID NO: 7.

The heterologous protein can also be modified to introduce additional substitutions when compared to the native protein and maintains or increases the robustness of the recombinant yeast cell. Such additional substitutions do not necessarily result in an additional glycosylation site and can be introduced for their ability to maintain or increase the robustness of the recombinant yeast cell. One or more substitutions can be made to the native protein to maintain or increase to robustness of recombinant yeast expressing the first heterologous protein.

In the embodiments in which the heterologous protein is a glucoamylase (such as, for example, in the embodiment in which the native protein is the glucoamylase of *Saccharomycopsis filbuligera* encoded by the glu 0111 gene as shown in SEQ ID NO: 1), the additional substitution(s) can be located at position(s) corresponding to 8, 12, 40, 101, 277 and/or 487 of SEQ ID NO: 1. The additional substitution can be any amino acid residues that is different from the amino acid residue located at position(s) 8, 12, 40, 101, 277 and/or 487 of SEQ ID NO: 1. For example, the heterologous protein can have the amino acid sequence of SEQ ID NO: 2. In an embodiment, the amino acid residue located at position 8 of the heterologous protein of SEQ ID NO: 2 is any amino acid residue except leucine and, in an embodiment, is an amino acid residue having a polar and uncharged side chain, such as, for example, a serine, a threonine, an asparagine, a glutamine a tyrosine or a cysteine residue. In still another embodiment, the amino acid residue located at position 8 of the heterologous protein of SEQ ID NO: 2 is a serine residue. In an embodiment, the amino acid residue located at position 12 of the heterologous protein of SEQ ID NO: 2 is any amino acid residue except phenylalanine and, in an embodiment, is an amino acid residue having an hydrophobic side chain, such as, for example, an isoleucine an alanine, a leucine, a phenylalanine, a valine, a proline or a glycine residue. In a further embodiment, the amino acid residue located at position 12 of the heterologous protein of SEQ ID NO: 2 is an isoleucine residue. In still another embodiment, the amino acid residue located at position 40 of the heterologous protein of SEQ ID NO: 2 is any amino acid residue except alanine and, in an embodiment, is an amino acid residue having a having a polar and charged side chain, such as, for example, a glutamic acid, a lysine, an arginine, an histidine, an aspartic acid or a glutamic acid residue. In still a further embodiment, the amino acid residue at position 40 of SEQ ID NO: 2 is an aspartic acid residue. In a further embodiment, the amino acid residue located at position 101 of the heterologous protein of SEQ ID NO: 2 is any amino acid residue except phenylalanine and, in an embodiment, is an amino acid residue having an hydrophobic side chain, such as, for example, an isoleucine an alanine, a leucine, a phenylalanine, a valine, a proline or a glycine residue. In a further embodiment, the amino acid residue located at position 101 of the heterologous protein of SEQ ID NO: 2 is a leucine residue. In a further embodiment, the amino acid residue located at position 277 of the heterologous protein of SEQ ID NO: 2 is any amino acid residue except lysine and, in an embodiment, is an amino acid residue having a polar and charged side chain, such as, for example, a glutamic acid, a lysine, an arginine, an histidine, an aspartic acid or a glutamic acid residue. In still another embodiment, the amino acid residue located at position 277 of the heterologous protein of SEQ ID NO: 2 is a glutamic acid residue. In a further embodiment, the amino acid residue located at position 487 of the heterologous protein of SEQ ID NO: 2 is any amino acid residue except phenylalanine and, in an embodiment, is an amino acid residue having an hydrophobic side chain, such as, for example, an isoleucine an alanine, a leucine, a phenylalanine, a valine, a proline or a glycine residue. In still another embodiment, the amino acid residue located at position 487 of the heterologous protein of SEQ ID NO: 2 is an isoleucine residue.

In the context of the present disclosure, the heterologous protein can be further modified to include a tethering region (so as to allow the localization of the secreted heterologous protein at the external surface of the yeast host cell) and/or fused to another entity (to create a fusion protein).

In the context of the present disclosure, the host cell can be a yeast. Suitable yeast host cells can be, for example, from the genus *Saccharomyces, Kluyveromyces, Arxula, Debaryomyces, Candida, Pichia, Phaffia, Schizosaccharomyces, Hansenula, Kloeckera, Schwanniomyces* or *Yarrowia*. Suitable yeast species can include, for example, *S. cerevisiae, S. bulderi, S. barnetti, S. exiguus, S. uvarum, S. diastaticus, K. lactis, K. marxianus* or *K. fragilis*. In some embodiments, the yeast is selected from the group consisting of *Saccharomyces cerevisiae, Schizzosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus, Schizosaccharomyces pombe* and *Schwanniomyces occidentalis*. In one particular embodiment, the yeast is *Saccharomyces cerevisiae*. In some embodiments, the host cell can be an oleaginous yeast cell. For example, the oleaginous yeast cell can be from the genus *Blakeslea, Candida, Cryptococcus, Cunninghamella, Lipomyces, Mortierella, Mucor, Phycomyces, Pythium, Rhodosporidum, Rhodotorula, Trichosporon* or *Yarrowia*. In some alternative embodiments, the host cell can be an oleaginous microalgae host cell (e.g., for example, from the genus *Thraustochytrium* or *Schizochytrium*).

In some embodiments, the host cell, in the absence of the heterologous nucleic acid molecule, is a thermotolerant host cell. Thermotolerant host cells can be particularly useful in simultaneous saccharification and fermentation processes by allowing externally produced cellulases and ethanol-producing host cells to perform optimally in similar temperature ranges. In some embodiments, the thermotolerant host cell can grow at temperatures above about 30° C., about 31° C., about 32° C., about 33° C., about 34° C., about 35° C., about 36° C., about 37° C., about 38° C., about 39° C., about 40° C., about 41° C. or about 42° C. In additional embodiments, the thermotolerant host cell express the heterologous protein at temperatures above about 30° C., about 31° C., about 32° C., about 33° C., about 34° C., about 35° C., about 36° C., about 37° C., about 38° C., about 39° C., about 40° C., about 41° C., about 42° C., or about 50° C. In yet another embodiment, the thermotolerant host cell can grow at temperatures from about 30° C. to 60° C., about 30° C. to 55° C., about 30° C. to 50° C., about 40° C. to 60° C., about 40° C. to 55° C. or about 40° C. to 50° C. In some embodiments, the thermotolerant host cell can produce the heterologous protein at temperatures from about 30° C. to 60° C., about 30° C. to 55° C., about 30° C. to 50° C., about 40° C. to 60° C., about 40° C. to 55° C. or about 40° C. to 50° C.

Thermotolerant host cells can include, for example, *Issatchenkia orientalis, Pichia mississippiensis, Pichia mexicana, Pichia farinosa, Clavispora opuntiae, Clavispora lusitaniae, Candida mexicana, Hansenula polymorpha* or *Kluyveromyces* sp. host cells.

As described herein, the host cells are genetically engineered (transduced or transformed or transfected) with the heterologous nucleic acid molecule encoding the heterologous protein. The nucleic acid molecule can be introduced in the host cell on a vector, which may be, for example, a cloning vector or an expression vector comprising a sequence encoding a heterologous protein. The host cells can comprise one or more heterologous nucleic acid molecule(s) each being either present as integrated copies or independently-replicating copies.

The host cell can also comprise additional heterologous nucleic acid molecules which facilitates the production of ethanol from lignocellulosic biomass. For example, the host cell described in WO 2011/153516 (expressing one of more saccharalytic enzymes) or in WO 2012/138942 (comprising a deletion in an enzyme involved in glycerol production) can be used in the context of the present disclosure. In still another example, the heterologous protein described in WO 2011/153516 can be further modified to restore the robustness of the recombinant yeast host cell expressing them.

The transformed host cells or cell cultures, as described above, can be further analyzed for hydrolysis of cellulose, or starch, or pentose sugar utilization (e.g., by a sugar detection assay), for a particular type of saccharolytic enzyme activity (e.g., by measuring the individual endoglucanase, glucosidase, cellobiohydrolase, xylanase, glucanase, xylosidase, xylan esterase, arabinofuranosidase, galactosidase, cellobiose phosphorylase, cellodextrin phosphorylase, mannanase, mannosidase, xyloglucanase, endoxylanase, glucuronidase, acetylxylanesterase, arabinofuranohydrolase, swollenin, glucuronyl esterase, expansin, pectinase, feruoyl esterase, alpha-amylase, beta-amylase, glucoamylase, pullulanase, isopullulanase, alpha-glucosidase, beta-glucosidase, galactosidase, arabinase, arabinoxylanase, arabinosidase, arabinofuranosidase, arabinoxylanase, arabinosidase, and arabinofuranosidase, arabinose isomerase, ribulose-5-phosphate 4-epimerase, xylose isomerase, xylulokinase, xylose reductase, xylose dehydrogenase, xylitol dehydrogenase, xylonate dehydratase, xylose transketolase, and/or xylose transaldolase) or for total cellulase activity. Endoglucanase activity can be determined, for example, by measuring an increase of reducing ends in an endoglucanase specific CMC or hydroxyethylcellulose (HEC) substrate. Cellobiohydrolase activity can be measured, for example, by using insoluble cellulosic substrates such as the amorphous substrate phosphoric acid swollen cellulose (PASC) or microcrystalline cellulose (Avicel) and determining the extent of the substrate's hydrolysis. β-glucosidase activity can be measured by a variety of assays, e.g., using cellobiose. Assays for activity of other saccharolytic enzyme types are known in the art and are exemplified below.

A total saccharolytic enzyme activity, which can include the activity of endoglucanase, glucosidase, cellobiohydrolase, xylanase, glucanase, xylosidase, xylan esterase, arabinofuranosidase, galactosidase, cellobiose phosphorylase, cellodextrin phosphorylase, mannanase, mannosidase, xyloglucanase, endoxylanase, glucuronidase, acetylxylanesterase, arabinofuranohydrolase, swollenin, glucuronyl esterase, expansin, pectinase, feruoyl esterase protein, alpha-amylase, beta-amylase, glucoamylase, alpha-glucosidase, beta-glucosidase, galactosidase, arabinase, arabinoxylanase, arabinosidase, arabinofuranosidase, arabinoxylanase, arabinosidase, pullulanase, isopullulanase, arabinose isomerase, ribulose-5-phosphate 4-epimerase, xylose isomerase, xylulokinase, xylose reductase, xylose dehydrogenase, xylitol dehydrogenase, xylonate dehydratase, xylose transketolase, and xylose transaldolase can hydrolyze biomass feedstocks synergistically. For example, total cellulase activity can thus be measured using insoluble substrates including pure cellulosic substrates such as Whatman No. 1 filter paper, cotton linter, microcrystalline cellulose, bacterial cellulose, algal cellulose, and cellulose-containing substrates such as dyed cellulose, alpha-cellulose or pretreated lignocellulose. Specific activity of cellulases can also be detected by methods known to one of ordinary skill in the art, such as by the Avicel assay (described supra) that would be normalized by protein (cellulase) concentration measured for the sample. Total saccharolytic activity could be also measured using complex substrate containing starch, cellulose and hemicellulose such as corn mash by measuring released monomeric sugars.

One aspect of the present disclosure is thus related to the efficient production of lytic enzymes to aid in the digestion and utilization of starch, cellulose, and pentose sugars, and generation of products such as ethanol. A "saccharolytic enzyme" can be any enzyme involved in carbohydrate digestion, metabolism and/or hydrolysis, including amylases, cellulases, hemicellulases, cellulolytic and amylolytic accessory enzymes, inulinases, levanases, and pentose sugar hydrolasing enzymes. A "cellulase" can be any enzyme involved in cellulase digestion, metabolism and/or hydrolysis, including an endoglucanase, glucosidase, cellobiohydrolase, xylanase, glucanase, xylosidase, xylan esterase, arabinofuranosidase, galactosidase, cellobiose phosphorylase, cellodextrin phosphorylase, mannanase, mannosidase, xyloglucanase, endoxylanase, glucuronidase, acetylxylanesterase, arabinofuranohydrolase, swollenin, glucuronyl esterase, expansin, pectinase, and feruoyl esterase protein. An "amylase" can be any enzyme involved in amylase digestion and/or metabolism, including alpha-amylase, beta-amylase, glucoamylase, pullulanase, isopullulanase, and alpha-glucosidase. A pentose sugar hydrolyzing enzyme can be any enzyme involved in pentose sugar digestion, and/or metabolism, including xylanase, arabinase, arabinoxylanase, arabinosidase, arabinofuranosidase, arabinoxylanase, arabinosidase, and arabinofuranosidase, arabinose isomerase, ribulose-5-phosphate 4-epimerase, xylose isomerase, xylulokinase, xylose reductase, xylose dehydrogenase, xylitol dehydrogenase, xylonate dehydratase, xylose transketolase, and/or xylose transaldolase. A "protease" can be any enzyme involved in protein digestion and/or metabolisms. An "esterase" can be any enzyme (such as phytases) involved in the hydrolysis of an ester from an acid or an alcohol.

In additional embodiments, the recombinant host cells or cell cultures can be assayed for their ability to produce ethanol. Ethanol production can be measured by techniques known to one or ordinary skill in the art, e.g., by a standard HPLC refractive index method.

Modified Lytic Enzymes and Tools for their Production

The present disclosure further provides the modified heterologous proteins (such as the lytic enzymes described above) as well as corresponding fragments and/or variants that are expressed in a recombinant yeast host cell.

In an embodiment, the isolated heterologous protein (as well as their corresponding fragments and variants) can be provided in a purified form, at least in a partially purified form. For example, the isolated heterologous protein can be provided as a cell supernatant. In certain embodiments, the isolated heterologous proteins (as well as their corresponding fragments and variants) are provided in an isolated form, e.g., purified to homogeneity. In certain embodiments, high molecular weight material can be recovered from the yeast cell supernatant either by acetone precipitation or by buffering the samples with disposable de-salting cartridges. The isolated heterologous proteins can also be recovered and purified from recombinant yeast cell cultures by methods including spheroplast preparation and lysis, cell disruption using glass beads, and cell disruption using liquid nitrogen for example. Additional protein purification methods include ammonium sulfate or ethanol precipitation, acid extraction, anion or cation exchange chromatography, phosphocellulose chromatography, hydrophobic interaction chromatography, affinity chromatography, hydroxyl apatite chromatography, gel filtration, and lectin chromatography. Protein refolding steps can be used, as necessary, in completing configuration of the mature protein. Finally, high performance liquid chromatography (HPLC) can be employed for final purification steps.

The isolated heterologous proteins (as well as their corresponding fragments and variants) can be analyzed. Protein analysis methods include methods such as the traditional Lowry method, the BCA assay, absorbance at 280 nm, or the protein assay method according to BioRad's manufacturers protocol. Using such methods, the protein content of the modified lytic enzymes can be estimated. Additionally, to accurately measure protein concentration a isolated heterologous protein can be expressed with a tag, for example a His-tag or HA-tag and purified by standard methods using, for example, antibodies against the tag, a standard nickel resin purification technique or similar approach.

The isolated heterologous protein variants have at least 70%, 80%, 85%, 90%, 95%, 96%, 97%, 98% or 99% identity to the isolated heterologous proteins described herein. A variant comprises at least one amino acid difference when compared to the amino acid sequence of the modified lytic enzyme. Further, recombinant yeast expressing one or more isolated heterologous protein exhibits a robustness which is better or similar to corresponding yeast which does not express the one or more modified isolated heterologous protein variant. The term "percent identity", as known in the art, is a relationship between two or more polypeptide sequences or two or more polynucleotide sequences, as determined by comparing the sequences. The level of identity can be determined conventionally using known computer programs. Methods for determining percent identity, as discussed in more detail below in relation to polynucleotide identity, are also relevant for evaluating polypeptide sequence identity.

"Identity" can be readily calculated by known methods, including but not limited to those described in: Computational Molecular Biology (Lesk, A. M., ed.) Oxford University Press, NY (1988); Biocomputing: Informatics and Genome Projects (Smith, D. W., ed.) Academic Press, NY (1993); Computer Analysis of Sequence Data, Part I (Griffin, A. M., and Griffin, H. G., eds.) Humana Press, NJ (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PEN ALT Y=10). Default parameters for pairwise alignments using the Clustal method were KTUPLB 1, GAP PENALTY=3, WINDOW=5 and DIAGONALS SAVED=5.

The variants described herein may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide or (v) one in which a fragment of the polypeptide is soluble, i.e., not membrane bound, yet still binds ligands to the membrane bound receptor.

A "variant" of the isolated heterologous protein can be a conservative variant, or an allelic variant. As used herein, a conservative variant refers to alterations in the amino acid sequence that do not adversely affect the biological functions of the isolated heterologous protein. A substitution, insertion or deletion is said to adversely affect the protein when the altered sequence prevents or disrupts a biological function associated with the isolated heterologous protein. For example, the overall charge, structure or hydrophobic-hydrophilic properties of the protein can be altered without adversely affecting a biological activity. Accordingly, the amino acid sequence can be altered, for example to render the peptide more hydrophobic or hydrophilic, without adversely affecting the biological activities of the isolated heterologous protein.

The present disclosure further provides fragments of the isolated heterologous protein. The isolated heterologous protein "fragments" have at least at least 10, 20, 30, 40, 50, 60, 70, 80, 90, 100, 200, 300, 400, or 500 or more consecutive amino acids of the isolated heterologous protein. A fragment comprises at least one less amino acid residue when compared to the amino acid sequence of the isolated heterologous protein. Further, a recombinant yeast expressing one or more isolated heterologous protein fragment exhibits a robustness which is better or similar to a corresponding yeast which does not express the one or more isolated heterologous protein fragment. In some embodiments, fragments of the isolated heterologous protein can be employed for producing the corresponding full-length modified lytic enzyme by peptide synthesis. Therefore, the fragments can be employed as intermediates for producing the full-length proteins.

The present disclosure also provides nucleic acid molecules (also referred to as a heterologous nucleic acid molecule) encoding the isolated heterologous proteins, variants and fragments described herein. The nucleic acid molecule may be DNA (such as complementary DNA, synthetic DNA or genomic DNA) or RNA (which includes synthetic RNA) and can be provided in a single stranded (in either the sense or the antisense strand) or a double stranded form.

The contemplated nucleic acid molecules can include alterations in the coding regions, non-coding regions, or both. Examples are nucleic acid molecule variants containing alterations which produce silent substitutions, additions, or deletions, but do not alter the properties or activities of the encoded isolated heterologous proteins nor the robustness of the recombinant host cell comprising same. In certain embodiments, nucleotide variants are produced by silent substitutions due to the degeneracy of the genetic code.

In some embodiments, the nucleic acid molecules are codon-optimized with respect to the intended recipient yeast host cell. As used herein the term "codon-optimized coding region" means a nucleic acid coding region that has been adapted for expression in the cells of a given organism by replacing at least one, or more than one, codons with one or more codons that are more frequently used in the genes of that organism. In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism. The CAI of codon optimized sequences described herein corresponds to between about 0.8 and 1.0, between about 0.8 and 0.9, or about 1.0.

A codon optimized sequence may be further modified for expression in a particular organism, depending on that recipient's biological constraints. For example, large runs of "As" or "Ts" (e.g., runs greater than 4, 5, 6, 7, 8, 9, or 10 consecutive bases) can be removed from the sequences if these are known to effect transcription negatively. Furthermore, specific restriction enzyme sites may be removed for molecular cloning purposes. Additionally, the nucleic acid molecules can be checked for direct repeats, inverted repeats and mirror repeats with lengths of ten bases or longer, which can be modified manually by replacing codons with "second best" codons, i.e., codons that occur at the second highest frequency within the particular organism for which the sequence is being optimized.

The present disclosure also provides nucleic acid molecules that are hybridizable to the complement nucleic acid molecules described herein. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified, e.g., in Sambrook, J., Fritsch, E. F. and Maniatis, T. MOLECULAR CLONING: A LABORATORY MANUAL, Second Edition, Cold Spring Harbor Laboratory Press, Cold Spring Harbor (1989), particularly Chapter 11 and Table 11.1 therein. The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. For more stringent conditions, washes are performed at higher temperatures in which the washes are identical to those above except for the temperature of the final two 30 min washes in 0.2×SSC, 0.5% SDS are increased to 60° C. Another set of highly stringent conditions uses two final washes in 0.1×SSC, 0.1% SDS at 65° C. An additional set of highly stringent conditions are defined by hybridization at 0.1×SSC, 0.1% SDS, 65° C. and washed with 2×SSC, 0.1% SDS followed by 0.1×SSC, 0.1% SDS.

Hybridization requires that the two nucleic acid molecules contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived. For hybridizations with shorter nucleic acids, i.e., oligonucleotides, the position of mismatches becomes more important, and the length of the oligonucleotide determines its specificity. In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The nucleic acid molecules described herein encode isolated heterologous proteins that are at least about 70% to 75% identical to the amino acid sequence of the isolated heterologous protein, at least about 80%, 85%, or 90% identical to the amino acid sequence of the isolated heterologous protein, or at least about 95%, 96%, 97%, 98%, 99%, or 100% identical to the amino acid sequence of the isolated heterologous protein. Suitable nucleic acid fragments are at least about 70%, 75%, or 80% identical to the nucleic acid sequences reported herein, at least about 80%, 85%, or 90% identical to the nucleic acid sequences reported herein, or at least about 95%, 96%, 97%, 98%, 99%, or 100% identical to the nucleic acid sequences reported herein. Suitable nucleic acid fragments not only have the above identities/similarities but typically encode a protein having at least 50 amino acids, at least 100 amino acids, at least 150 amino acids, at least 200 amino acids, or at least 250 amino acids.

The nucleic acid molecules described herein comprises a coding region for the isolated heterologous proteins as well as its variants and fragments. A DNA or RNA "coding region" is a DNA or RNA molecule which is transcribed and/or translated into a polypeptide in a cell in vitro or in vivo when placed under the control of appropriate regulatory sequences. "Suitable regulatory regions" refer to nucleic acid regions located upstream (5' non-coding sequences), within, or downstream (3' non-coding sequences) of a coding region, and which influence the transcription, RNA processing or stability, or translation of the associated coding region. Regulatory regions may include promoters, translation leader sequences, RNA processing site, effector binding site and stem-loop structure. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region. In an embodiment, the coding region can be referred to as an open reading frame. "Open reading frame" is abbreviated ORF and means a length of nucleic acid, either DNA, cDNA or RNA, that comprises a translation start signal or initiation codon, such as an ATG or AUG, and a termination codon and can be potentially translated into a polypeptide sequence.

The nucleic acid molecules described herein can comprise transcriptional and/or translational control regions. "Transcriptional and translational control regions" are DNA regulatory regions, such as promoters, enhancers, terminators, and the like, that provide for the expression of a coding region in a host cell. In eukaryotic cells, polyadenylation signals are control regions.

In another aspect, the present disclosure relates to vectors which include nucleic acid molecules described herein, host cells which are genetically engineered with the vectors described herein as well as the production of the heterologous proteins by recombinant techniques. Host cells can be genetically engineered (transduced, transformed or transfected) with the vectors which may be, for example, a cloning vector, an integration vector or an expression vector. The vector may be, for example, in the form of a plasmid, a cosmid, an artificial chromosome, a viral particle, a phage, etc. The genetically engineered host cells can be cultured in conventional nutrient media modified as appropriate for activating promoters, selecting transformants or amplifying the genes described herein. The culture conditions, such as temperature, pH and the like, are those previously used with the host cell selected for expression, and will be apparent to the ordinarily skilled artisan. The vectors may contain one or more selectable marker genes to provide a phenotypic trait for selection of transformed host cells such as, for example, URA3, HIS3, LEU2, TRP1, LYS2 or ADE2, dihydrofolate reductase, neomycin (G418) resistance or zeocin resistance for eukaryotic cell culture, or tetracycline or ampicillin resistance in E. coli. The vectors may also contain a ribosome binding site for translation initiation and/or a transcription terminator. Exemplary terminators include, but are not limited to, the terminator of the adh3 gene (e.g., adh3t see, for example, SEQ ID NO: 54), the terminator of the idp1 gene (e.g., idp1t, see, for example, SEQ ID NO: 55), the terminator of the dit1 gene (e.g., dit1t, see, for example, SEQ ID NO: 56) as well as the terminator of the pma1 gene (e.g., pma1t, see, for example, SEQ ID NO: 57). The vector may also include appropriate sequences for amplifying expression.

Process for Making Ethanol Using Recombinant Yeast Host Cells

In another aspect, the present disclosure is directed to the use of recombinant yeast host cells and/or the isolated heterologous proteins to produce ethanol or other products from a biomass feedstock comprising starch, lignocellulosic matter, hexose and pentose sugars. Such methods can be accomplished, for example, by contacting a biomass feedstock with a recombinant yeast host cell and/or a heterologous protein (such as a recombinant lytic enzyme) expressed by the recombinant yeast host cell. Fermentation products include, but are not limited to products such as ethanol, butanol, acetate, amino acids and vitamins.

Numerous biomass feedstocks can be fermented by the recombinant yeast host cell and/or treated by the modified lytic enzyme. In some embodiments, substrates for can be divided into two categories, soluble and insoluble, based on their solubility in water. Soluble substrates include alphadextrins, cellodextrins or derivatives, carboxymethyl cellulose (CMC), or hydroxyethyl cellulose (HEC). Insoluble substrates include insoluble starch (raw or gelatinized), crystalline cellulose, microcrystalline cellulose (Avicel™), amorphous cellulose, such as phosphoric acid swollen cellulose (PASC), dyed or fluorescent cellulose, and lignocellulosic biomass. These substrates are generally highly ordered cellulosic material and thus only sparingly soluble. It will be appreciated that suitable lignocellulosic material may be any feedstock that contains soluble and/or insoluble cellulose, where the insoluble cellulose may be in a crystalline or non-crystalline form. In various embodiments, the lignocellulosic biomass comprises, for example, wood, corn, corn stover, sawdust, bark, leaves, agricultural and forestry residues, grasses such as switchgrass, ruminant digestion products, municipal wastes, paper mill effluent, recycled paper-based products (such as, for example, newspaper, cardboard) or combinations thereof.

In some embodiments, the present disclosure provides a process for hydrolyzing a biomass feedstock, for example a biomass feedstock as described above, by contacting the biomass feedstock with a recombinant host cell and/or a modified lytic enzyme. In some embodiments, the necessity of adding "external" modified lytic enzymes to the fermentation medium is reduced or annulled by the process described herein.

The process comprises combining a substrate to be hydrolyzed with a source of a modified lytic enzyme. In an embodiment, the substrate to be hydrolyzed is a lignocellulosic biomass and, in some embodiments, it comprises starch (in a gelatinized or raw form). The modified lytic enzyme can be provided in the form of a recombinant yeast host cell which expresses the modified lytic enzyme. This embodiment is advantageous because it can reduce the need to supplement the fermentation medium with external or purified enzymes while allowing the fermentation of the lignocellulosic biomass into a fermentation product (such as ethanol). Alternatively (or in combination), the modified lytic enzyme can be provided in at least a partially purified form. In such embodiment, it may be necessary to further provide a yeast cell capable of fermenting the lignocellulosic biomass into a fermentation product. In some embodiments, the process can be used to ferment the substrate to make ethanol.

In some embodiments of the process, when the substrate is starch and is provided in a gelatinized form, the first heterologous protein and/or the isolated glucoamylase can have the amino acid sequence of SEQ ID NO: 3. Alternatively, when the substrate is starch and is provided in a raw form, the first heterologous protein and/or the glucoamylase can have the amino acid sequence of SEQ ID NO: 4. In still yet another embodiment, when the substrate is starch, the first heterologous protein and/or the glucoamylase can have the amino acid sequence of SEQ ID NO: 7.

The production of ethanol can be performed at temperatures of at least about 25° C., about 28° C., about 30° C., about 31° C., about 32° C., about 33° C., about 34° C., about 35° C., about 36° C., about 37° C., about 38° C., about 39° C., about 40° C., about 41° C., about 42° C., or about 50° C. In some embodiments, when a thermotolerant yeast cell is used in the process, the process can be conducted at temperatures above about 30° C., about 31° C., about 32° C., about 33° C., about 34° C., about 35° C., about 36° C., about 37° C., about 38° C., about 39° C., about 40° C., about 41° C., about 42° C., or about 50° C. In some embodiments, the thermotolerant yeast cell can produce ethanol from cellulose at temperatures from about 30° C. to 60° C., about 30° C. to 55° C., about 30° C. to 50° C., about 40° C. to 60° C., about 40° C. to 55° C. or about 40° C. to 50° C.

In some embodiments, the process can be used to produce ethanol at a particular rate. For example, in some embodiments, ethanol is produced at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, or at least about 500 mg per hour per liter.

Ethanol production can be measured using any method known in the art. For example, the quantity of ethanol in fermentation samples can be assessed using HPLC analysis. Many ethanol assay kits are commercially available that use, for example, alcohol oxidase enzyme based assays.

Process for Making Recombinant Yeast Host Cells and Isolated Heterologous Proteins The present disclosure also provides a process for making robust recombinant yeast host cells capable of and, under the appropriate conditions, expressing an heterologous protein (such as, for example, a lytic enzyme). The process is particularly useful for increasing the robustness of a recombinant yeast host cell which, upon the introduction of an heterologous nucleic acid molecule encoding for the heterologous protein, has lost some robustness during its growth at high temperatures.

The first step of this process does include providing a first recombinant yeast host cell which exhibits a reduction in growth robustness at high temperatures. The first recombinant yeast host cell comprises a first heterologous nucleic acid molecule which comprises a first nucleic acid molecule coding for a first heterologous protein. The first heterologous nucleic acid molecule can comprise regulatory elements for the expression of the first heterologous protein. In some embodiments, the first heterologous protein is secreted from the recombinant yeast host cell and, in yet a further embodiment, the first heterologous protein is a lytic enzyme (as described above, such as, for example, a glucoamylase or an α-amylase). The first recombinant yeast host cell exhibits a reduced growth (which includes a reduced growth rate) when compared to a corresponding first yeast host cell which does not comprises the first heterologous nucleic acid molecule. In some embodiments, the corresponding first yeast host cell can express the first heterologous protein using a different nucleic acid molecule than the first heterologous nucleic acid molecule. In another embodiment, the corresponding first yeast host cell is not recombinant and does not comprise any heterologous nucleic acid molecule. The first recombinant yeast host cell is also capable of secreting a higher amount of the first heterologous protein when compared to the corresponding first yeast host cell, when both yeast cells are cultured in similar conditions.

Once the first recombinant yeast host cell has been provided, its first heterologous nucleic acid molecule is modified to generate a second heterologous nucleic acid molecule. In an embodiment, the first heterologous nucleic acid molecule can be modified to introduce an anaerobic-regulated promoter operatively linked to the first heterologous nucleic acid molecule coding for the first heterologous protein. In another embodiment, the first heterologous nucleic acid molecule can be modified to include at least one amino acid substitution (for example to include a further putative glycosylation site) in the first heterologous protein. In still a further embodiment, the first nucleic acid molecule can be modified to include both the anaerobic-regulated promoter as well as the at least one amino acid substitution in the first heterologous protein.

The second heterologous nucleic acid molecule can also be obtained by replacing the promoter of the first heterologous nucleic acid molecule by one or more than one of the anaerobic-regulated protein as described herein. The second heterologous nucleic acid molecule can be obtained by inserting in the first heterologous nucleic acid molecule one or more than one of the anaerobic-regulated protein as described herein. The promoters that are being included in the second heterologous nucleic acid molecule are operatively linked to the nucleic acid molecule coding for the heterologous protein. In some embodiments, the one or more than one anaerobic promoters that are being introduced to the first heterologous nucleic acid molecule are positioned upstream (e.g., 5') of the nucleic acid molecule coding for the heterologous protein.

The second heterologous nucleic acid molecule can be obtained by modifying the nucleic acid sequence of the first heterologous nucleic acid molecule, especially the nucleic acid sequence of the first nucleic acid molecule coding for the first heterologous protein. In the context of the present disclosure, the modified first nucleic acid molecule is referred to as a second nucleic acid molecule and encodes a second heterologous protein. The modification in the nucleic acid sequence of the first heterologous nucleic acid molecule is located in the first nucleic acid molecule and introduces one or more amino acid substitutions in the first heterologous protein. The amino acid substitution(s) can result in the addition of a putative glycosylation site in the second heterologous protein. The added putative glycosylation site can be located in the N-terminal region of the heterologous protein (either prior to the first glycosylation site of the first heterologous protein or prior to the first alpha-helix region of the first heterologous protein). The added putative glycosylation site is preferably a N-glycosylation site and can be obtained by substituting an amino acid by an amino acid having a hydroxyl oxygen in its side chain (such as, for example, serine, threonine, tyrosine, hydroxylysine or hydroxyproline) or by arginine. As shown herein, the introduction of such modifications can restore, and in some embodiments, maintain the yeast robustness when grown at high temperature.

The process optionally includes a step of comparing the robustness of the first recombinant yeast host cell comprising the first heterologous nucleic acid molecule with the robustness of the second recombinant yeast host cell comprising the second heterologous nucleic acid molecule. This determination is preferably being made at high temperatures. At high temperatures, the robustness of the second recombinant yeast host cell should be increased when compared to the robustness of the first recombinant yeast host cell. If it is determined that the second recombinant yeast host cell is not more robust, at high temperatures, than the first recombinant yeast host cell, the first recombinant yeast host cell can be resubmitted to the process and other modifications than the ones introduced into the second recombinant yeast host cell can be introduced.

The process can also include a step of comparing the amount and/or activity (e.g., enzymatic activity) of the first and second heterologous proteins expressed by the first and second recombinant yeast host cell. The amount and/or of the first and second heterologous proteins should substantially be similar. If it is determined that the amount and/or activity of the second heterologous protein lower than the amount and/or activity of the first heterologous protein, the first recombinant yeast host cell can be resubmitted to the process and other modifications than the ones introduced into the second recombinant yeast host cell can be introduced.

In some embodiments, it may be beneficial to introduce additional modifications to the second heterologous nucleic acid molecule to further increase the robustness of the second recombinant yeast host cell to high temperatures. Such additional modifications can be, for example, introduced randomly in the second heterologous nucleic acid molecule and screened for their ability to further improve the robustness of the yeast host cell at high temperatures.

For example, the process can further comprise generating, from the second recombinant yeast host cell, a first generation of mutant recombinant yeast host cells. Each of the mutant recombinant yeast host cells of this first generation bears one or more modifications (when compared to the nucleic acid sequence of the second heterologous nucleic acid molecule) in the heterologous nucleic acid molecule they bear. This at least one modification is preferably located in the nucleic acid molecule coding for the heterologous protein. In some embodiments, these modifications introduce at least one amino acid substitution in the heterologous protein. In the first generation of mutant recombinant yeast host cells, it is possible that the same modification be introduced into more than one mutants.

In one embodiment, the first generation of mutant recombinant yeast host cells can be obtained by generating a plurality of mutated heterologous nucleic acid molecules outside the cells (for example using a PCR-based approach) and introducing one or more mutated heterologous nucleic acid molecules in the mutant recombinant yeast host cells. In a further embodiment, only a single copy of a mutant heterologous nucleic acid molecule is introduced per mutant recombinant yeast host cells. In yet another embodiment, the single copy of the mutant heterologous nucleic acid molecule is integrated into the genome of the mutant recombinant yeast host cell. As shown in the Examples below, it is possible to use a yeast strain modified to allow for the integration of a single copy of the mutant heterologous nucleic acid molecule at a single fcy1 site.

Once the first generation of mutant recombinant yeast host cells has been generated, it must be determined if they encode a "functional" mutated heterologous protein which exhibits the biological activity of the second heterologous protein. It is expected that using a random mutagenesis approach will generate mutated heterologous protein which no longer exhibits the biological activity of the second heterologous protein. In the context of the process described herein, the term "biological activity" refers to the activity of the second heterologous protein. When the second heterologous protein is an enzyme, its biological activity refers to its enzymatic activity. In order to determine which mutants are functional, the process can comprise a step of selecting, from the first generation, mutant recombinant yeast host cells capable of expressing a mutated heterologous protein having the biological activity of the second heterologous protein. Mutants of the first generation will be selected on the basis that they are capable of expressing a mutated heterologous protein having the same or an improved biological activity when compared to the second heterologous protein. In the embodiment in which the second heterologous protein encodes an amylase, the selection can be done using starch selection plates combined with the use of iodine vapor.

The "functional" mutants of the first generation are then being further characterized and the amino acid sequence of the mutated heterologous protein they express can be determined. This determination can be made, for example, by determining the sequence of the mutated heterologous nucleic acid molecule (in total or in part) and ascertaining the amino acid sequence of the mutated heterologous protein (in total or in part). This determination allows for the selection of two or more functional mutants which each express a mutated heterologous protein having different amino acid sequences.

Once the two or more functional mutants have been selected, the amino acid modifications of the mutated heterologous proteins encoded by the mutant heterologous nucleic acid molecules are combined within in single heterologous nucleic acid molecule (referred to as the third heterologous nucleic acid molecule) which is then reintroduced into a host cell to generate the third recombinant yeast host cell. The third recombinant yeast host cell will thus include a third heterologous nucleic acid molecule encoding a third heterologous protein bearing the modifications (e.g., amino acid substitutions) of the selected mutant recombinant yeast host cell from the first generation.

The third recombinant yeast host cell is then used to generate a second generation of mutant recombinant yeast host cells and screened for further functional mutant recombinant yeast host cells. As such, the process further comprise generating, from the third recombinant yeast host cell, a second generation of mutant recombinant yeast host cells. Each of the mutant recombinant yeast host cell of this second generation bears one or more modifications (when compared to the nucleic acid sequence of the third heterologous nucleic acid molecule) in the heterologous nucleic acid molecule they bear. This at least one modification is preferably located in the nucleic acid molecule coding for the heterologous protein. In some embodiments, these modifications introduce at least one an amino acid substitution in the heterologous protein. In the second generation of mutant recombinant yeast host cells, it is possible that the same modification be introduced into more than one mutants. As indicated above, the second generation of mutant recombinant yeast host cells can be obtained by generating a plurality of mutated heterologous nucleic acid molecules outside the cells (for example using a PCR-based approach) and introducing one or more mutated heterologous nucleic acid molecules in the mutant recombinant yeast host cells. In a further embodiment, only a single copy of a mutant heterologous nucleic acid molecule is introduced per mutant recombinant yeast host cells. In yet another embodiment, the single copy of the mutant heterologous nucleic acid molecule is integrated into the genome of the mutant recombinant yeast host cell. As shown in the Examples below, it is possible to use a yeast strain modified to allow for the integration of a single copy of the mutant heterologous nucleic acid molecule at a single fcy1 site.

Once the second generation of mutant recombinant yeast host cells has been generated, it must be determined if they encode a "functional" mutated heterologous protein which exhibits the biological activity of the third heterologous protein. It is expected that using a random mutagenesis approach will generate mutated heterologous protein which no longer exhibits the biological activity of the third heterologous protein. In the context of the process described herein, the term "biological activity" refers to the activity of the second heterologous protein. When the third heterologous protein is an enzyme, its biological activity refers to its enzymatic activity. In order to determine which mutants are functional, the process can comprise a step of selecting, from the second generation, mutant recombinant yeast host cells capable of expressing a mutated heterologous protein having the biological activity of the third heterologous protein. Mutants of the second generation will be selected on the basis that they are capable of expressing a mutated heterologous protein having the same or an improved biological activity when compared to the third heterologous protein. In the embodiment in which the third heterologous protein encodes an amylase, the selection can be done using starch selection plates combined with the use of iodine vapor.

The "functional" mutants of the second generation are then being further characterized and the amino acid sequence of the mutated heterologous protein they express can be determined. This determination can be made, for example, by determining the sequence of the mutated heterologous nucleic acid molecule (in total or in part) and ascertaining the amino acid sequence of the mutated heterologous protein (in total or in part). This determination allows for the selection of two or more functional mutants which each express a mutated heterologous protein having different amino acid sequences.

Once the two or more functional mutants have been selected from the second generation, the amino acid modifications of the mutated heterologous proteins encoded by the mutant heterologous nucleic acid molecules are combined within in single heterologous nucleic acid molecule (referred to as the fourth heterologous nucleic acid molecule) which is then reintroduced into a host cell to generate the fourth recombinant yeast host cell. The fourth recombinant yeast host cell will thus include a fourth heterologous nucleic acid molecule encoding a fourth heterologous protein bearing the modifications (e.g., amino acid substitutions) of the mutant recombinant yeast host cell selected from the second generation.

The process can also include generating and selecting mutant recombinant yeast host cell from a third, fourth and even a fifth generation of recombinant yeast host cell.

The present invention will be more readily understood by referring to the following examples which are given to illustrate the invention rather than to limit its scope.

Example I—Material and Methods

Strain Construction. The glucoamylase gene, glu0111-CO (SEQ ID NO:1), was designed by creating a synthetic DNA sequence (codon optimized for Saccharomyces cerevisiae) based on the amino acid sequence of the wild type glucoamylase gene glu0111 from Saccharomycopsis fibuligera (Gen Bank Accession No. CAC83969). The synthesized glu0111-CO gene was first assembled into a S. cerevisiae expression plasmid using standard yeast recombination-based, PCR cloning practices as was previously described in WO2011/153516 and WO2012/138942.

In particular, strains expressing the glu0111-CO under control of the constitutive promoter, tef2p, were constructed using directed integration in which two copies of the glu0111-CO were integrated into the FYC1 loci of the diploid S. cerevisiae host strain via homologous recombination with non-coding FCY1 flanking sequences. These PCR products were engineered with overlapping ends to promote homologous recombination in vivo. A 2-micron plasmid with a hygromycin resistance marker (hph) was co-transformed with the PCR products to enable selection against untransformed cells. The transformed cells were first cultivated overnight in YPD+hygromycin (300 µg/mL) broth and then plated on a medium containing 5-fluorocytosine to select against FCY1 and simultaneous assembly and integration of the glu0111-CO cassettes into the chromosome.

Similarly, strains expressing the glu0111-CO under control of the anaerobic-controlled TDH1 promoter, were constructed using the same methodology, but instead of the adh3 terminator, the native S. cerevisiae idp1 terminator sequence was used.

Strains expressing four copies of the glu0111-CO gene were constructed using the same methodology, however the constructs were inverted to create a convergent orientation to promote stability and prevent sequence homology that could result in recombination of the glu0111-CO sequences.

TABLE G

Primers used to construct two copy and four copy strains 2 copy glu011-CO cassette regulated by TEF2p/ADH3t

| DNA Fragment | SEQ ID NO: | Primer # | Primer Sequence |
|---|---|---|---|
| FCY5' Flank | 22 | X28001 | CTGACTCGTTGGTGGGGTCCACACCATAGA |
|  | 23 | X27580 | TAGCTATGAAATTTTTAACTCTTC |
| FCY 3' Flank | 24 | X27581 | AGCACGCAGCACGCTGTATTTACGTATTTAATTTT |
|  | 25 | X27582 | AGCCAGCTTTTTGAAGAGTTAAAAATTTCATAGCT-AGGGCGCCATAACCAAGGTATCTAT |

TABLE G-continued

| Primers used to construct two copy and four copy strains | | | |
|---|---|---|---|
| TEF2p | 26 | X28015 | AACAGCGGTCAAGAAAACGGTCAATCTGATCATG-TTTAGTTAATTATAGTTCGTTGACCG |
| | 27 | X20072 | AATATACGGTCAACGAACTATAATTAACTAAACAT-GATCAGATTGACCGTTTTCTTGACC |
| glu011-CO | 28 | X20071 | AGACTTTCATAAAAAGTTTGGGTGCGTAACACGC-TATCACAATAATTCGATCAACTTGTT |
| | 29 | X31384 | GCTAATAGAGCCAGAAACAAGTTGATCGAATTAT-TGTGATAGCGTGTTACGCACCCAAAC |
| ADH3t | 30 | X31385 | AATTAAATACGTAAATACAGCGTGCTGCGTGCTA-TGAGGAAGAAATCCAAATCCTAATGA |
| | 31 | X26468 | AATTAAATACGTAAATACAGCGTGCTGCGTGCTA-TGAGGAAGAAATCCAAATCCTAATGA |

| 2 copy glu011-CO cassette regulated by the TDH1p/IDP1t | | | |
|---|---|---|---|
| DNA Fragment | SEQ ID NO: | Primer # | Primer Sequence |
| FCY5' Flank | 22 | X28001 | CTGACTCGTTGGTGGGGTCCACACCATAGA |
| | 23 | X27580 | TAGCTATGAAATTTTTAACTCTTC |
| FCY 3' Flank | 24 | X27581 | AGCACGCAGCACGCTGTATTTACGTATTTAATTTT |
| | 25 | X27582 | AGCCAGCTTTTTGAAGAGTTAAAAATTTCATAGCT-AGGGCGCCATAACCAAGGTATCTAT |
| TDH1p | 32 | X27405 | CCAGCTTTTTGAAGAGTTAAAAATTTCATAGCTAA-GAAACGAATGTATATGCTCATTTAC |
| | 33 | X28699 | AAACAGCGGTCAAGAAAACGGTCAATCTGATCAT-TTTGTTTTGTGTGTAAATTTAGTGAA |
| glu011-CO | 34 | X24018 | ACAGTACTTCACTAAATTTACACACAAAACAAAAT-GATCAGATTGACCGTTTTCTTGACC |
| | 35 | X27282 | GAAAAAAAAGTGGTAGATTGGGCTACGTAAATT-CGATCACAATAATTCGATCAACTTG |
| IDP1t | 36 | X27283 | GAGCCAGAAACAAGTTGATCGAATTATTGTGATC-GAATTTACGTAGCCCAATCTAC |
| | 37 | X25154 | TATATAAAATTAAATACGTAAATACAGCGTGCTGC-GTGCTCAAATGACGTCAAAAGAAGT |

| 4 copy glu0111-CO cassette regulated by the TEF2p/ADH3t and HXT7p/PMA1t | | | |
|---|---|---|---|
| DNA Fragment | SEQ ID NO: | Primer # | Primer Sequence |
| FCY5' Flank | 22 | X28001 | CTGACTCGTTGGTGGGGTCCACACCATAGA |
| | 23 | X27580 | TAGCTATGAAATTTTTAACTCTTC |
| FCY 3' Flank | 24 | X27581 | AGCACGCAGCACGCTGTATTTACGTATTTAATTTT |
| | 25 | X27582 | AGCCAGCTTTTTGAAGAGTTAAAAATTTCATAGCT-AGGGCGCCATAACCAAGGTATCTAT |
| TEF2p | 26 | X28015 | AACAGCGGTCAAGAAAACGGTCAATCTGATCATG-TTTAGTTAATTATAGTTCGTTGACCG |
| | 27 | X20072 | AATATACGGTCAACGAACTATAATTAACTAAACAT-GATCAGATTGACCGTTTTCTTGACC |
| glu011-CO | 28 | X20071 | AGACTTTCATAAAAAGTTTGGGTGCGTAACACGC-TATCACAATAATTCGATCAACTTGTT |
| | 29 | X31384 | GCTAATAGAGCCAGAAACAAGTTGATCGAATTAT-TGTGATAGCGTGTTACGCACCCAAAC |
| ADH3t | 30 | X31385 | AATTAAATACGTAAATACAGCGTGCTGCGTGCTA-TGAGGAAGAAATCCAAATCCTAATGA |
| | 31 | X25481 | AATTTTTAATATATATAATGCACACACACTAATTT-ATGAGGAAGAAATCCAAATCCTAAT |
| PMA1t | 38 | X28017 | GCTTGAAGGTCATTAGGATTTGGATTTCTTCCTC-ATAAATTAGTGTGTGTGCATTATATA |
| | 39 | X24678 | TCCTGTTGAAGTAGCATTTAATCAT |
| glu011-CO | 40 | X20066 | CAAAAATTATGATTAAATGCTACTTCAACAGGAT-TACAATAATTCGATCAACTTGTTTCT |

TABLE G-continued

Primers used to construct two copy and four copy strains

|  | | Primer # | Primer Sequence |
|---|---|---|---|
| | 41 | X19705 | AAAACAAAAAGTTTTTTTAATTTTAATCAAAAAAT-GATCAGATTGACCGTTTTCTTGAC |
| HXT7p | 42 | X27998 | CAAAAACAGCGGTCAAGAAAACGGTCAATCTGA-TCATTTTTTGATTAAAATTAAAAAAAC |
| | 43 | X25201 | AATTAAATACGTAAATACAGCGTGCTGCGTGCTC-CAGAAAGGCAACGCAAAATTTTTTTT |

4 copy glu0111-CO cassette regulated by the PAU5p/DIT1t and TDH1p/IDP1t

| DNA Fragment | SEQ ID NO: | Primer # | Primer Sequence |
|---|---|---|---|
| FCY5' Flank | 22 | X28001 | CTGACTCGTTGGTGGGGTCCACACCATAGA |
| | 23 | X27580 | TAGCTATGAAATTTTTAACTCTTC |
| FCY 3' Flank | 24 | X27581 | AGCACGCAGCACGCTGTATTTACGTATTTAATTTT |
| | 25 | X27582 | GTAGTGCTGTCTGAACAGAATAAATGCGTTCTTGG |
| PAU5p | 44 | X27379 | GAGCCAGCTTTTTGAAGAGTTAAAAATTTCATAGCT-AATACGAATCAGATACTGTTCGG |
| | 45 | X28186 | CAAAAACAGCGGTCGAGAAAACGGTCAATCTGATC-ATTGTATTTGTTGTTTTTTGGGTTG |
| glu011-CO | 46 | X25892 | ATGATCAGATTGACCGTTTTCTCG |
| | 47 | X27996 | AACAAAAAGGTAGACCAATGTAGCGCTCTTACTTTA-TCACAATAATTCGATCAACTTGTT |
| DIT1 | 48 | X27458 | CTAATAGAGCCAGAAACAAGTTGATCGAATTATTGT-GATAAAGTAAGAGCGCTACATTGG |
| | 49 | X27812 | CATAGGCTCATATAATACTTCTTTTGACGTCATTTGA-AGTGAGTTCTATTCACGCAATCG |
| IDP1t | 50 | X27811 | TCTTCTTTGATACTACCGATTGCGTGAATAGAACTCA-CTTCAAATGACGTCAAAAGAAGT |
| | 51 | X27995 | GCTAATAGAGCCAGAAACAAGTTGATCGAATTATTGT-GATCGAATTTACGTAGCCCAATC |
| glu011-CO | 35 | X27282 | GAAAAAAAAAGTGGTAGATTGGGCTACGTAAATTCGA-TCACAATAATTCGATCAACTTG |
| | 46 | X25892 | ATGATCAGATTGACCGTTTTCTCG |
| TDH1p | 52 | X28187 | GCAAAAACAGCGGTCGAGAAAACGGTCAATCTGAT-CATTTTGTTTTGTGTAAATTTAG |
| | 53 | X28152 | TATATAAAATTAAATACGTAAATACAGCGTGCTGCG-TGCTAGAAACGAATGTATATGCTC |

The maps of the various engineered cassettes are shown in FIGS. 5B to 5E.

Starch Assay Characterizations.

For evaluation of strains expressing secreted amylases and glucoamylases, a plate-based starch assay was performed. Strains of interest were grown 24-72 h in YPD. The cultures were then centrifuged at 3000 rpm to separate the cells from the culture supernatant containing the secreted enzymes. The supernatant was then added to a 1% cornstarch solution in a 50 mM sodium acetate buffer (pH 5.0). For the gelatinized starch assay, the corn starch solution was heated at 99° C. for 5 mins. For raw starch assays, the heating step was not included. The assay was conducted using a 4:1 starch solution:supernatant ratio and incubated at 35° C. for 1-4 h. The reducing sugars were measured using the Dinitrosalicylic Acid Reagent Solution (DNS) method, using a 2:1 DNS:starch assay ratio and boiled at 100° C. for 5 mins. The absorbance was measured at 540 nm.

Plate Reader (Growth) Assays.

Growth assays were performed using a BioTek plate reader to kinetically monitor OD 600 nm. Cells were cultured overnight in YPD and diluted approximately 1:1000 in fresh media to achieve a starting OD of 0.01. High temperature growth assays were performed at 38° C. for 24-48 h in an anaerobic chamber.

Example II—Anaerobic Promoters for Increasing High Temperature Robustness

Some of the material and methods used in this example were presented in Example I.

*Saccharomyces cerevisiae* bearing a codon optimized version of the *Saccharomycopsis fibuligera* glu0111 glucoamylase gene (e.g., SEQ ID NO: 5, see WO2011/153516) was integrated into an industrial yeast host and the effects of various promoter types on growth, glucoamylase production and activity have been determined.

Figure 1:
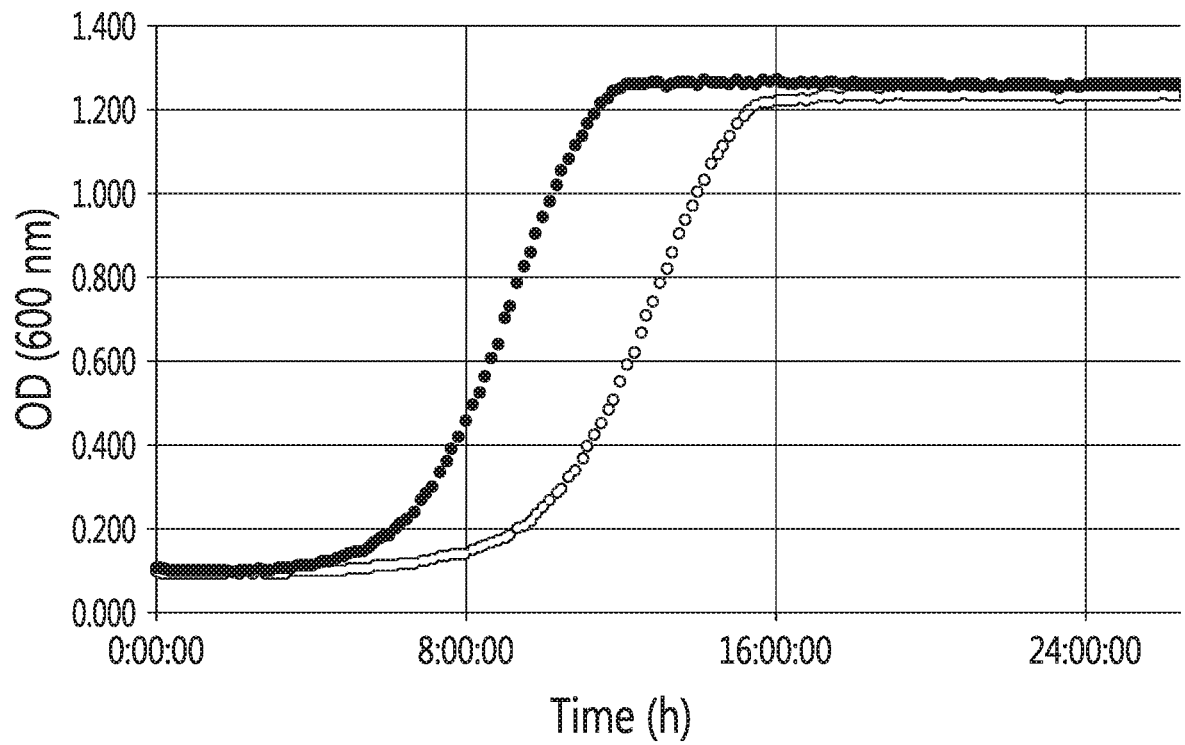
FIG. 1 illustrates growth curves of a strain of S. cerevisiae genetically-engineered to express a S. fibuligera glucoamylase under the control of a constitutive promoter (tef2p or ○) or an anaerobic-regulated promoter (tdh1p or ●) under anaerobic conditions. Results are shown as the optical density at 600 nm (OD(600 nm)) in function of time of incubation (hours). The incubation was conducted in a YPD media at 38° C. The S. cerevisiae strain using the tdh1 promoter exhibited improved growth when compared to the S. cerevisiae strain using the tef2 promoter.

Firstly, a strong constitutive promoter (e.g., a constitutive promoter of the tef2 gene (herein referred to as "tef2p")) was compared to an anaerobic-regulated promoter (e.g., an anaerobic-regulated promoter from the tdh1 gene, herein referred as "tdh1p") to drive the expression of the *Saccharomycopsis fibuligera* glu0111 glucoamylase gene in *S. cerevisiae*. As shown in FIG. 1, at high temperatures, the use of the constitutive promoter tef2p caused a decrease in the growth rate (also referred to as a decrease in robustness) of the transgenic yeast strains when compared to those using the anaerobic-regulated tdh1p promoter. Results obtained with other constitutive promoters (cwp2p, ssa1p, eno1p, pgk1p) indicated that a similar decrease in growth at high temperatures is observed (data not shown).

Figure 2:
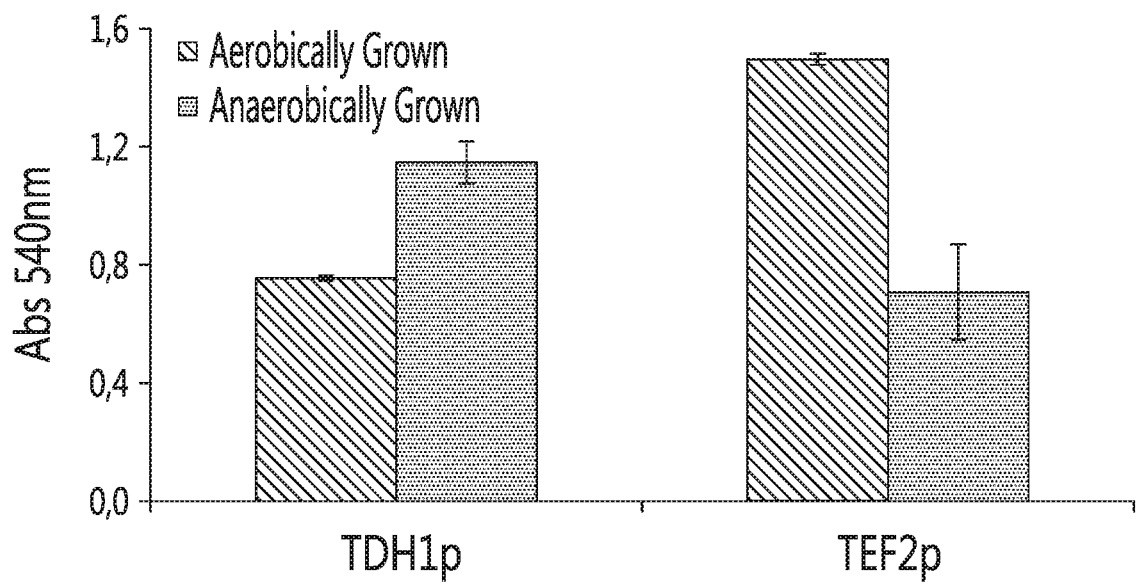
FIG. 2 illustrates the secreted starch-degrading activity of two strains of S. cerevisiae genetically-engineered to express a S. fibuligera glucoamylase under the control of a constitutive promoter (tef2p) or an anaerobic-regulated promoter (tdh1p). Results are shown as amylase activity (as measured as the absorbance at 540 nm (Abs540 nm)) in function of strains and fermentation conditions (diagonal hatch bars=aerobically grown, black bars=anaerobically grown). Under anaerobic conditions, the S. cerevisiae strain using the tdh1 promoter produced more glucoamylase than the strain using the tef2 promoter.

The secreted starch-degrading activity of both strains has then been determined in aerobic and anaerobic conditions. As shown on FIG. 2, in anaerobic conditions, the use of the anaerobic-regulated tdh1p promoter resulted in higher starch degrading activity than the constitutive tef2p promoter.

Figure 3:
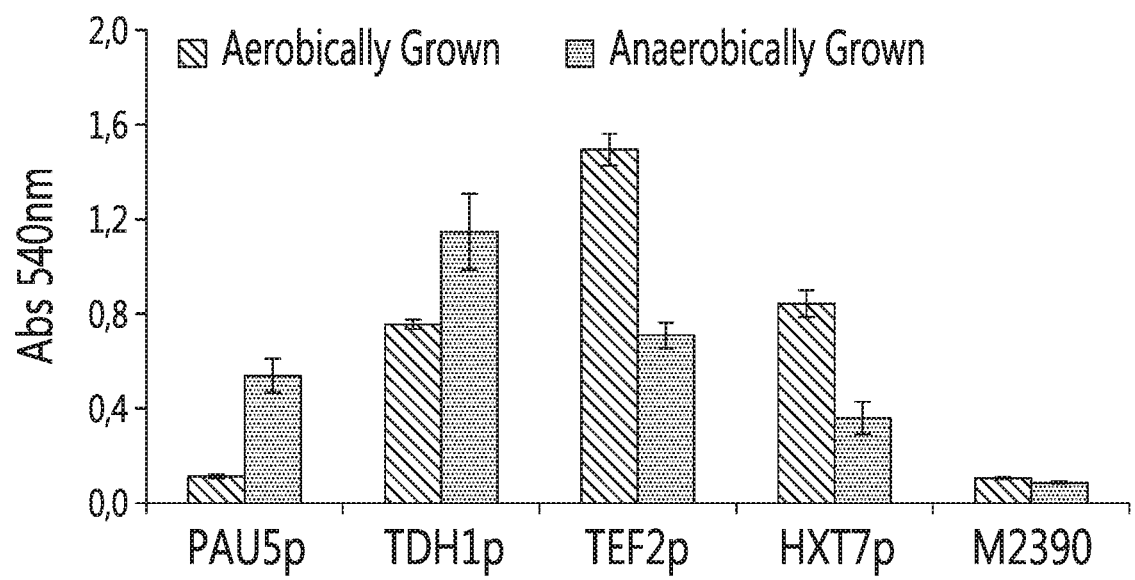
FIG. 3 illustrates the secreted starch-degrading activity of strains of S. cerevisiae genetically-engineered to express a S. fibuligera glucoamylase under the control of a constitutive promoter (tef2p), an anaerobic-regulated promoter (tdh1p or pau5p) or a glucose-regulated promoter (hxt7p). For comparison, the secreted starch-degrading activity of a wild-type (non-transgenic) S. cerevisiae (M2390) is included. Results are shown as the amylase activity (as measured as the absorbance at 540 nm (Abs540 nm)) in function of strains and fermentation conditions (diagonal hatch bars= aerobically grown, black bars=anaerobically grown).

Secondly, additional promoters (the *S. cerevisiae* anaerobic-regulated promoter of the pau5 gene (e.g., "pau5p") or the *S. cerevisiae* glucose-regulated promoter of the htx7 gene (e.g., "htx7p")) have been screened for their ability to allow the secretion of the *Saccharomycopsis fibuligera* glu0111 glucoamylase gene in transgenic *S. cerevisiae*. As shown on FIG. 3, under anaerobic conditions, the use of the anaerobic-regulated tdh1p promoter resulted in higher starch degrading activity than the other promoters tested.

Figure 4B:
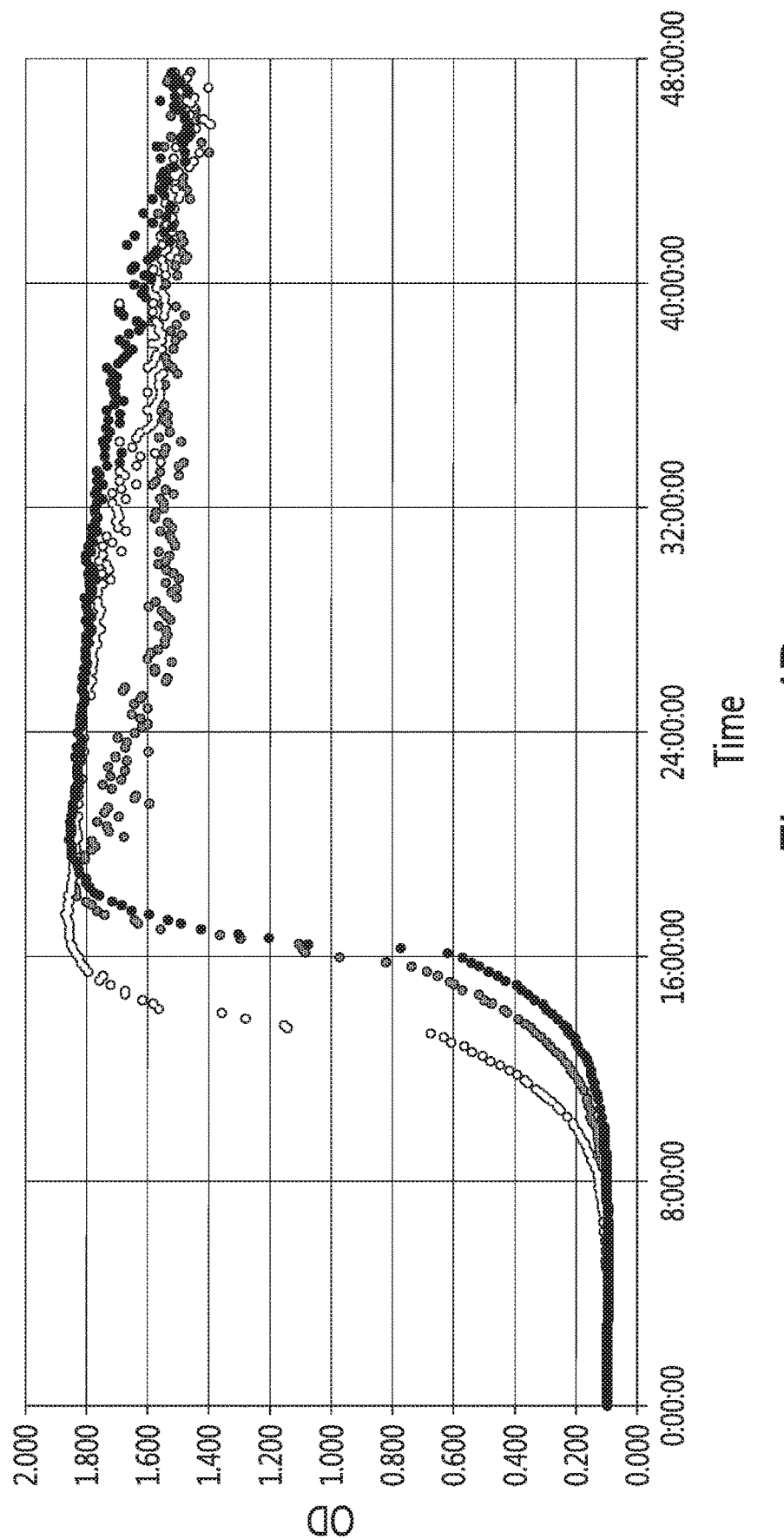
Figure 5A:
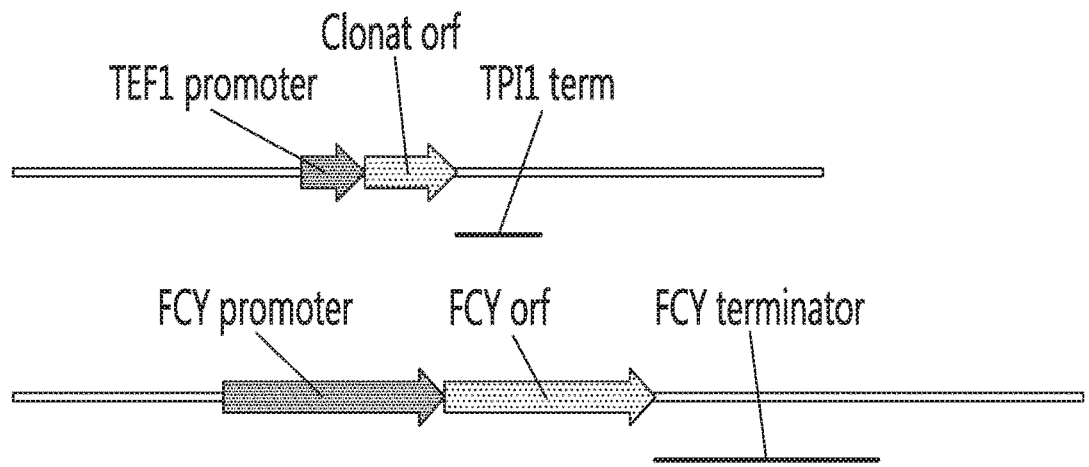
Figure 5B:
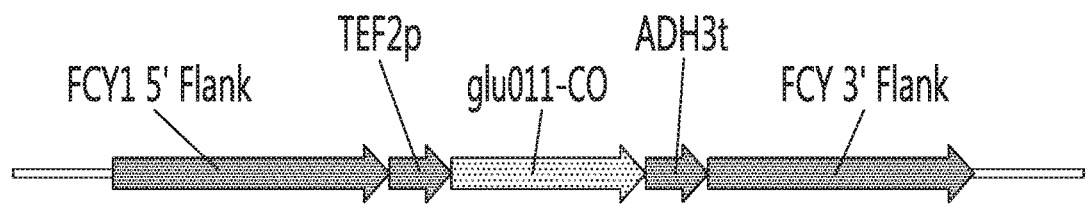
Figure 5C:
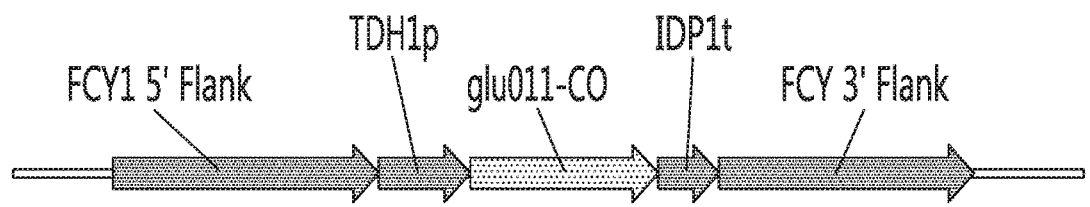
Figure 5D:
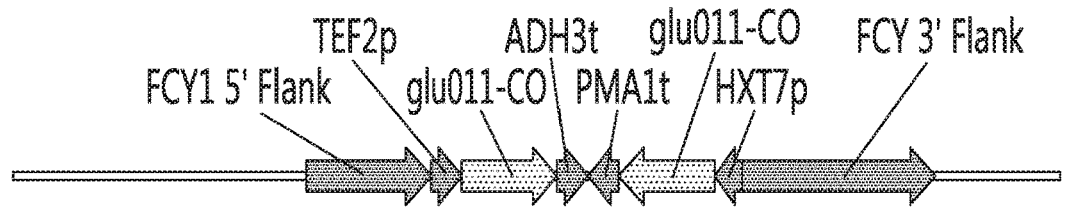
Figure 5E:
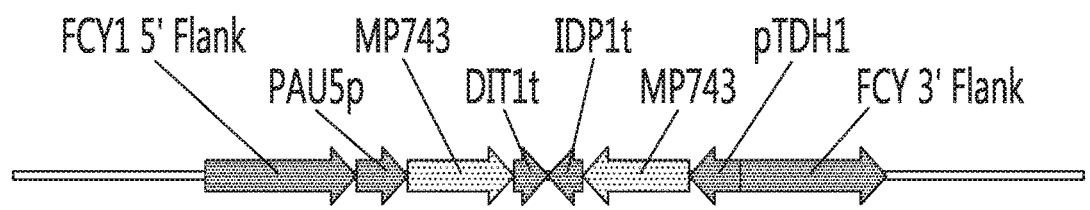

Thirdly, promoters have been combined (tef2p and hxt7p or pau5p and tdh1p) and their effect on glucoamylase production in transgenic *S. cerevisiae* has been determined. As shown on FIG. 4, under anaerobic conditions, the combination of the pau5p and the tdh1p promoters increased glucoamylase protein production (FIG. 4A) while maintaining robustness at high temperature (FIG. 4B).

Example III—Temperature Resistant Glucoamylase Mutants

Some of the material and methods used in this example were presented in Example I.
Iterative Combinatorial Mutagenesis.

This process involved multiple rounds of random mutagenesis via error-prone PCR in which individual mutations were screened and evaluated separately before combining to evaluate additive effects. Error-prone PCR was conducted using the commercially available Clontech Diversify™ PCR Random Mutagenesis Kit. Conditions were selected to target approximately 2.7 mutations per 1 Kb (Volume by buffer condition: PCR-grade water 38 µL; 10× Titanium™ Taq buffer 5 µL; 8 mM MnSO$_4$ 3 µL; 2 mM dGTP 1 µL; 50× Diversify™ dNTP mix 1 µL; primer mix 1 µL; template DNA 1 µL; Titanium™ Taq polymerase 1 µL).

Error-prone reactions were setup to amplify only the open reading frame of wild-type *S. fibuligera* glu0111 gene (SEQ ID NO: 5). Simultaneously, reactions were setup using conventional Taq polymerase to amplify the regulatory elements (the promoter of the tef2 gene (tef2p, SEQ ID NO: 8) and the terminator of the adh3 gene (adh3t, SEQ ID NO: 54). These elements were transformed into the fcy1 site of *S. cerevisiae* strain M4251, a strain that was engineered to have only one fcy1 site in order to integrate only one mutated construct per cell. The second copy of the fcy1 allele was previously marked with a Clonat™ antibiotic marker (nourseothricin) to prevent a secondary integration, therefore only one mutated version of the glu0111 gene would be integrated and evaluated (see FIG. 5A). PCR products were transformed into M4251 host cells using yeast-mediated ligation.

Once the random mutants were transformed, colonies were selected on YPD plates containing starch (0.5% corn starch), Clonat™ (100 µg/mL), and 5-fluorocytosine (100 µg/mL of 5-FC) which selects for the deletion of the fcy1 gene and maintenance of the Clonat™ gene. After 24 h of growth at 35° C., the selective plates were incubated in the presence of approximately 0.5 g dried iodine flakes. The iodine vapor stains the amylose components of the starch creating a temporary blue color. However, the iodine vapor avoids any cross-contamination between colonies and allows the visualization of colonies that have successfully secreted a functional glucoamylase which creates a clearing zone (FIG. 6). The clearing zones allow for easy distinction between transformants which have received functional mutants versus those which have non-functional mutations. Only functional mutants were picked for further analysis using gelatinized starch assays to measure secreted starch-degrading activity.

After two successive rounds of error-prone PCR, top mutants were screened individually and sequenced to identify point mutations in their open reading frames (see FIG. 7 and Table B).

Some of the mutations were then combined into a single open-reading frame to design high-secreting glucoamylase mutants. However, the combinations of these mutations deteriorated growth of the transgenic strains at high temperatures (see results obtained for strain M6423 when compared to strain M2390 as shown on FIG. 8).

In order to mitigate this loss of temperature robustness, a glycosylation site was introduced near the N-terminal region (by directly mutating residue 40 to an asparagine residue). The introduction of this additional glycosylation site not only provided a slight boost in secreted activity (see results obtained for strain M9694 and M10052 when compared to strain M8841 on FIG. 4), but also restored high temperature growth (see results obtained for strain M8861 when compared to strain M6423 shown on FIG. 11).

It was observed that the mutations in MP738 affected activity on raw starch substrates (FIG. 10). Protein analysis identified that two mutations were located within the putative starch binding domain (e.g., the asparagine substitution (G36N) which introduced a glycosylation site NX[S/T] and the mutation F487I, which has been shown via homology modeling to be within 20 Å of G36N) that could explain this reduction in activity on raw starch.

To mitigate this loss in activity, an N-terminal glycosylation site was integrated in the wild-type *S. fibuligera* glucoamylase (SEQ ID NO: 1). Potential mutations were identified by sequence analysis of the N-terminal region of the protein. Single mutations substituting an asparagine, serine or threonine which would result in an N-linked glycosylation site motif NX[S/T] were included. The targeted region was limited to amino acids preceding the first natively occurring N-linked glycosylation motif, or the beginning of the first alpha-helix determined by homology modelling/secondary structure prediction servers if no other glycosylation sites existed. After this determination, all possible mutants were constructed and then evaluated for activity and cell robustness effects. Several yeast strains bearing the amino acid residue at location 40 was replaced with an asparagine residue were designed.

This directed mutation improved secreted activity (FIGS. 10A to C) without affecting high temperature growth (FIGS. 11A and B).

Example IV—Temperature Resistant Alpha-Amylase Mutants

Some of the material and methods used in this example were presented in Example I.

The addition of a glycosylation site was also successful in restoring significant growth defects with heterologous expression of MP85 α-amylase (FIG. 12) as well, indicating that this may be applicable across multiple saccharolytic enzymes.

Example V—Ethanol Fermentation

Some of the material and methods used in this example were presented in Example I.

A fermentation was performed with *S. cerevisiae* stains M10624, M10156 or M2390 using 34% total solids (TS) with the addition 500 ppm urea. Commercial raw starch enzyme was added during the fermentation (0.427 μl/g TS commercial raw starch enzyme for M2390; 0.171 μl/g TS for M10156 and 0.043 μl/g TS for MM8841). An inoculum of 0.3 g/L dry cell weight was used. The fermentation lasted 88 h. During the fermentation, the temperature was held at 32° C. for 24 h then lowered to 30° C. for the remainder of the fermentation. Samples were analyzed by HPLC for ethanol concentration. As shown on FIG. 13, under these experimental conditions, strains M10624 and M10156 generated a similar ethanol yield.

While the invention has been described in connection with specific embodiments thereof, it will be understood that the scope of the claims should not be limited by the preferred embodiments set forth in the examples, but should be given the broadest interpretation consistent with the description as a whole.

REFERENCES

Gasser B, Saloheimo M, Rinas U, Dragosits M, Rodriguez-Carmona E, Baumann K, Giuliani M, Parrilli E, Branduardi P, Lang C, Porro D, Ferrer P, Tutino M L, Mattanovich D, Villaverde A. Protein folding and conformational stress in microbial cells producing recombinant proteins: a host comparative overview. Microb Cell Fact. 2008 Apr. 4; 7:11.

Idiris A, Tohda H, Kumagai H, Takegawa K. Engineering of protein secretion in yeast: strategies and impact on protein production. Appl Microbiol Biotechnol. 2010 March; 86(2):403-17.

Kwast K E, Lai L C, Menda N, James D T 3rd, Aref S, Burke P V. Genomic analyses of anaerobically induced genes in *Saccharomyces cerevisiae*: functional roles of Rox1 and other factors in mediating the anoxic response. J Bacteriol. 2002 Jan; 184(1):250-65.

Martinez J L, Liu L, Petranovic D, Nielsen J. Pharmaceutical protein production by yeast: towards production of human blood proteins by microbial fermentation. Curr Opin Biotechnol. 2012 December; 23(6):965-71.

Mattanovich D, Gasser B, Hohenblum H, Sauer M. Stress in recombinant protein producing yeasts. J Biotechnol. 2004 Sep. 30; 113(1-3):121-35.

Tai S L, Boer V M, Daran-Lapujade P, Walsh M C, de Winde J H, Daran J M, Pronk J T. Two-dimensional transcriptome analysis in chemostat cultures. Combinatoriaeffects of oxygen availability and macronutrient limitation in Saccharomycecerevisiae. J Biol Chem. 2005 Jan. 7; 280 (1):437-47.

ter Linde J J, Liang H, Davis R W, Steensma H Y, van Dijken J P, Pronk J T. Genome-wide transcriptional analysis of aerobic and anaerobic chemostat cultures of *Saccharomyces cerevisiae*. J Bacteriol. 1999 December; 181(24): 7409-13.

What is claimed is:

1. A recombinant yeast host cell comprising an heterologous nucleic acid molecule having a first promoter operatively linked to a first nucleic acid molecule coding for a first heterologous protein, wherein:
   the first heterologous protein is a glucoamylase which comprises an amino acid sequence having at least 90% identity to the amino acid sequence of SEQ ID NO: 1 and has an amino acid substitution at one or more of positions 8, 12, 40, 101, 277 and 487 of SEQ ID NO: 1.

2. The recombinant yeast host cell of claim 1, wherein the first promoter is capable of increasing a level of expression of the first heterologous protein when the recombinant yeast host cell is in anaerobic conditions, compared to the level of expression of the first heterologous protein when the recombinant yeast host cell is placed in aerobic conditions.

3. The recombinant yeast host cell of claim 2, wherein the heterologous nucleic acid molecule further comprises a second promoter capable of increasing the expression of the first heterologous protein when the recombinant yeast host cell is in anaerobic conditions and wherein the second promoter is operatively linked to the first nucleic acid molecule.

4. The recombinant yeast host cell of claim 3, wherein the first promoter and the second promoter are selected from the group consisting of glyceraldehydes 3-phosphate dehydrogenase (GAPDH) isozyme 1 promoter (tdh1p), seripauperin 5 promoter (pau5p), hyperosmolarity-responsive 7 promoter (hor7p), alcohol dehydrogenase 1 promoter (adh1p), glyceraldehyde-3-phosphate dehydrogenase (GAPDH) isozyme 2 promoter (tdh2p), glyceraldehyde-3-phosphate dehydrogenase (GAPDH) isozyme 3 promoter (tdh3p), glycerol-3-phosphate dehydrogenase promoter (gpd1p), cell division cycle pyruvate kinase promoter (cdc19p), enolase 2 promoter (eno2p), pyruvate decarboxylase 1 promoter (pdc1p), hexose transporter 3 promoter (hxt3p) and triose phosphate isomerase 1 promoter (tpi1p).

5. The recombinant yeast host cell of claim 4, wherein the first promoter and the second promoter are pau5p and tdh1p.

6. The recombinant yeast host cell of claim 1, wherein the amino acid substitution introduces a putative glycosylation site in the first heterologous protein.

7. The recombinant yeast host cell of claim 6, wherein the amino acid substitution is located in an N-terminal region of the first heterologous protein.

8. The recombinant yeast host cell of claim 6, wherein the amino acid substitution which comprises the putative glycosylation site comprises an asparagine residue.

9. The recombinant yeast host cell of claim 1 being from the genus *Saccharomyces*.

10. The recombinant yeast host cell of claim 9 being from the species *Saccharomyces cerevisiae*.

11. The recombinant yeast host cell of claim 2, wherein the first promoter and the second promoter consist of pauSp and tdhlp and wherein the first heterologous protein has the amino acid sequence of SEQ ID NO: 4.

12. The recombinant yeast host cell of claim 1, wherein the first heterologous protein comprises the amino add sequence set forth in SEQ ID NO: 2, SEQ ID NO: 3 or SEQ ID NO: 4.

13. An isolated glucoamylase having the amino acid sequence of SEQ ID NO: 2, SEQ ID NO: 3 or SEQ ID:4.

14. A recombinant yeast host cell comprising a first heterologous protein which comprises an amino acid sequence having at least 90% identity to the amino acid sequence of SEQ ID NO: 4, wherein amino acid position 40 of SEQ ID NO: 4 is asparagine.

15. An isolated glucoamylase comprising an amino acid sequence having at least 90% identity to the amino acid sequence of SEQ ID NO: 4, wherein the isolated glucoamylase has an asparagine residue at amino acid position 40 of SEQ ID NO: 4.

16. A process for hydrolyzing a lignocellulosic biomass, said process comprising combining the lignocellulosic biomass with the recombinant yeast host cell of claim 1 under conditions so as to allow cleavage of the lignocellulosic biomass by the first heterologous protein when expressed by the recombinant yeast host cell.

* * * * *

UNITED STATES PATENT AND TRADEMARK OFFICE
CERTIFICATE OF CORRECTION

PATENT NO. : 11,332,728 B2
APPLICATION NO. : 15/757325
DATED : May 17, 2022
INVENTOR(S) : Charles F. Rice et al.

It is certified that error appears in the above-identified patent and that said Letters Patent is hereby corrected as shown below:

In the Claims

Column 85, Claim 1, Line 11:
"acid molecule coding fora first" should read: --acid molecule coding for a first--;

Column 85, Claim 4, Line 34:
"group consisting of glyceraldehydes 3-phosphate" should read: --group consisting of glyceraldehyde-3-phosphate--;

Column 86, Claim 11, Line 22:
"second promoter consist of pauSp" should read: --second promoter consist of pau5p--;

Column 86, Claim 11, Line 23:
"and tdhlp and wherein" should read: --and tdh1p and wherein--.

Signed and Sealed this
Twentieth Day of February, 2024

Katherine Kelly Vidal
*Director of the United States Patent and Trademark Office*